US007468184B2

(12) United States Patent
Sato et al.

(10) Patent No.: US 7,468,184 B2
(45) Date of Patent: Dec. 23, 2008

(54) THERAPEUTIC AGENT FOR CACHEXIA

(75) Inventors: Koh Sato, Shizuoka (JP); Toshiaki Tsunenari, Shizuoka (JP); Kimie Ishii, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 176 days.

(21) Appl. No.: 10/337,981

(22) Filed: Jan. 8, 2003

(65) Prior Publication Data

US 2003/0138424 A1 Jul. 24, 2003

Related U.S. Application Data

(62) Division of application No. 09/423,800, filed as application No. PCT/JP98/02116 on May 13, 1998, now abandoned.

(30) Foreign Application Priority Data

| May 15, 1997 | (JP) | ................................. 9-125505 |
| Jul. 18, 1997 | (JP) | ................................. 9-194445 |

(51) Int. Cl.
*A61K 39/395* (2006.01)

(52) U.S. Cl. .............. 424/145.1; 424/133.1; 424/138.1; 424/145.1; 424/155.1

(58) Field of Classification Search ................. 424/9.1, 424/130.1, 184.1, 133.1, 138.1, 141.1, 142.1, 424/155.1
See application file for complete search history.

(56) References Cited

U.S. PATENT DOCUMENTS

| 4,771,124 | A | 9/1988 | Rosenblatt et al. ........... 530/324 |
| 5,001,223 | A | 3/1991 | Rosenblatt et al. ........... 530/324 |
| 5,217,896 | A | 6/1993 | Kramer et al. .......... 435/240.27 |
| 5,626,845 | A * | 5/1997 | Yoneda et al. ............ 424/145.1 |
| 5,849,695 | A | 12/1998 | Cohen et al. ................... 514/12 |
| 5,993,817 | A | 11/1999 | Yoneda et al. ............ 424/158.1 |

FOREIGN PATENT DOCUMENTS

| EP | 0 293 130 | 11/1988 |
| EP | 0293 158 | 11/1988 |
| EP | 0 449 405 | 10/1991 |
| EP | 0 811 383 | 12/1997 |
| EP | 0 878 201 A1 | 11/1998 |
| EP | 0 962 467 A1 | 12/1999 |
| EP | 0962467 A1 * | 12/1999 |
| EP | 1 004 313 A1 | 5/2000 |
| EP | 1 090 643 A1 | 4/2001 |
| JP | 2-207099 | 8/1990 |
| JP | 4-502408 | 5/1992 |
| JP | 4-228089 | 8/1992 |
| JP | 7-165790 | 6/1995 |
| JP | 7-316195 | 12/1995 |
| JP | 11-80025 | 3/1999 |
| JP | 11-222440 | 8/1999 |
| JP | 2000-080100 | 3/2000 |
| WO | WO 89/11297 | 11/1989 |
| WO | WO 89/11298 | 11/1989 |
| WO | WO 90/07861 | 7/1990 |
| WO | WO 91/16928 | 11/1991 |
| WO | WO 92/00753 | 1/1992 |
| WO | WO 92/17602 | 10/1992 |
| WO | WO 92/19759 | 11/1992 |
| WO | WO 93/13133 | 7/1993 |
| WO | WO 94/11523 | 5/1994 |
| WO | WO 96/03437 | 2/1996 |
| WO | WO 96/39184 | 2/1996 |
| WO | WO 96/22790 | 8/1996 |
| WO | WO 9622790 A1 * | 8/1996 |
| WO | WO 96/26737 | 9/1996 |
| WO | WO 96/33735 | 10/1996 |
| WO | WO 98/13388 | 4/1998 |
| WO | WO 9813388 A1 * | 4/1998 |
| WO | WO 98/51329 | 11/1998 |
| WO | WO 99/57139 | 11/1999 |
| WO | WO 00/00219 | 1/2000 |

OTHER PUBLICATIONS

Paul ( Fundamental Immunology, 3rd Edition, 1993. pp. 292-295, under the heading "Fv Structure and Diversity in Three Dimensions").*
Rudikoff et al (Proc. Natl. Acad. Sci. USA, 79:1979-1983, Mar. 1982).*
Bendig (Methods: A Companion to Methods in Enzymology 1995; 8:83-93).*
Hashimoto et al. (Clin. Cancer Res. 2007; 12: 292-298).*
Rodenburg et al. (Hybridoma 1998; 17: 1-8).*
U.S. Appl. No. 09/269,332, filed Mar. 25, 1999, Sato et al.
Abou-Samra et al., Expression Cloning of a Common Receptor for Parathyroid Hormone and Parathyroid Hormone-Related Peptide from Rat Osteoblast-Like Cells: A Single Receptor Stimulates Intracellular Accumulation of Both cAMP and Inositol Trisphosphates and Increases Intracellular Free Calcium, *Proceedings of the National Academy of Sciences*, 89:2732-2736 (1992).
Baba, PTH/PTHrP, *Clinical Calcium*, 5:97-101 (1995) (English Translation).
Beck, S.A., et al., Lipolytic Factors Associated with Murine and Human Cancer Cachexia, *Journal of the National Cancer Institute*, 82:1922-1926 (1990).
Belyavsky et al., PCR-Based cDNA Library Construction: General cDNA Libraries at the Level of a Few Cells, *Nucleic Acids Research*, 17:2919-2933 (1989).
Benet et al, "Pharmacokinetics: The Dynamics of Drug Absorption, Distribution, and Elimination," In: *The Pharmacological Basis of Therapeutics*, 8th edition, pp. 3-32 (1990).

(Continued)

*Primary Examiner*—Brandon J Fetterolf
(74) *Attorney, Agent, or Firm*—Oblon, Spivak, McClelland, Maier & Neustadt, P.C.

(57) ABSTRACT

The invention relates to a therapeutic agent for cachexia comprising, as an active ingredient, a substance capable of inhibiting the binding between a parathyroid hormone related protein (PTHrP) and a receptor thereof.

10 Claims, 19 Drawing Sheets

OTHER PUBLICATIONS

Burtis, Parathyroid Hormone-Related Protein: Structure: Function, and Measurement, *Clinical Chemistry*, 38:2171-2183 (1992).

Carter et al. Humanization of an Anti-p185$^{HER2}$ Antibody for Human Cancer Therapy, *Proceedings of the National Academy of Sciences*, 89:4285-4289 (1992).

Chirgwin et al., Isolation of Biologically Active Ribonucleic Acid From Sources Enriched in Ribonuclease, *Biochemistry*, 18:5294-5299 (1979).

Chomczynsk et al., Single-Step Method of RNA Isolation By Acid Guanidinum Thiocyanate-Phenol-Chloroform Extraction, *Analytical Biochemistry*, 162:156-159 (1987).

Chothia, Canonical Structures for the Hypervariable Regions of Immunoglobulins, *Journal of Molecular Biology*, 196:901-917 (1987).

Co et al., Chimeric and Humanized Antibodies with Specificity for the CD33 Antigen, *The Journal of Immunology*, 148:1149-1154 (1992).

Co et al., Humanized Antibodies for Antiviral Therapy, *Proceedings of the National Academy of Science*, 88:2869-2873 (1991).

Coleman et al., Biochemical Mechanisms of Parathyroid Hormone Action, *The Parathyroids, Basic and Clinical Concepts*, 239-258 (1994).

Cuisinier et al., Mechanisms That Generate Human Immunoglobulin Diversity Operate From the 8$^{th}$ Week of Gestation in Fetal Liver, *European Journal of Immunology*, 23:110-118 (1993).

Dariavach et al., Human Immunoglobulin $C_\lambda 6$ Gene Encodes the kern$^+$Oz $\lambda$ Chain and $C_\lambda 4$ and $C_\lambda 5$ are Pseudogenes, *Proceedings of the National Academy of Sciences*, 84:9078 (1987).

Deftos et al., Utilization of a Potentially Universal Downstream Primer in the Rapid Identification and Charaterization of V$\lambda$ Genes From Two New Human V$\lambda$ Families, *Scandinavian Journal of Immunology*, 39:95-103 (1994).

de St. Groth, et al., Production of Monoclonal Antibodies: Strategy and Tactics, *Journal of Immunological Methods*, 35:1-21 (1980).

Dworkin, et al., Dietary Intake in Patients with Acquired Immunodeficiency Syndrome (AIDS), Patients with AIDS-Related Complex, and Serologically Positive Human Immunodeficiency Virus Patients: Correlations with Nutritional Status, *Journal of Parenteral and Enteral Nutrition*, 14:605-609 (1990).

Farmer et al., Speculations on the Design of Nonpeptidic Peptidomimetics, *TIPS*, 4:362-365 (1982).

Frohman et al., Rapid Production of Full-Length cDNAs From Rare Transcripts: Amplification Using a Single Gene-Specific Oligonucleotide Primer, *Proceedings of the National Academy of Sciences*, 85:8998-9002 (1988).

Galfrèet al., Rat x Rat Hybrid Myelomas and A Monoclonal Anti-Fd Portion of Mouse IgG, *Nature*, 277:131-133 (1979).

Gorman et al., Reshaping a Therapeutic CD4 Antibody, *Proceedings of the National Academy of Sciences*, 88:4181-4185 (1991).

Hammond, M., et al., Respiratory Muscle Strength in Congestive Heart Failure, *Chest*, 98:1091-1094 (1990).

Hardman, J.G. et al., (ed.), Goodman & Gilman's, "The Pharmacological Basis of Therapeutics", Section XIII, Hormones and Hormone Anatgonists, McGraw-Hill Co. (USA) 9$^{th}$ ed., at. 1528-1529, (1995).

Hardman, J.G., et al. (ed.), "Agents Affecting Calcification and Bone Turnover" in Goodman and Gilman's "The Pharmacological Basis of Therapeutics", McGraw-Hill Co. (USA) 9$^{th}$ ed., at 1523-1524 (1995).

Harris et al., Therapeutic Antibodies—The Coming of Age, *TIBTECH*, 11:42-44 (1993).

Ikeda, "Development of Novel Endocrinotherapy Targeting Cancer and Paraneoplastic Syndromes," Progress in Clinical Pharmacology, 16:155-161 (1995) (English Abstract).

Jones et al., Rapid PCR-Cloning of Full-Length Mouse Immunoglobulin Variable Regions, *Bio/Technology*, 9:88-89 (1991).

Jüppner et la., A G Protein-Linked Receptor for Parathyroid Hormone and Parathyroid Hormone-Related Peptide, *Science*, 254:1024-1026 (1991).

Kaji, H. et al., "Role of Dual Signal Transduction Systems in the Stimulation of Bone Resorption by Parathyroid Hormone-Related Peptide, The Direct Involvement of cAMP-Dependent Protein Kinase," *Horm. Metab. Res*. 25:421-424 (1993).

Kajimura, N., et al., Toxohormones Responsible for Cancer Cachexia Syndrome in Nude Mice Bearing Human Cancer Cell Lines, Cancer Chemother Pharmacol, 38:S48-S52 (1996).

Karlsson et al., Kinetic Analysis of Monoclonal Antibody-Antigen Interactions with a New Biosensor Based Analytical System, *Journal of Immunological* Methods, 145:229-240 (1991).

Kato, A., et al. "Incisor Change Induced by Excessive PTHrP in Rats," Abstracts of 16$^{th}$ Meeting of Japanese Society of Toxicologic Pathology, p. 17 (2000) (English Translation).

Kearney et al., A New Mouse Myeloma Cell Line That Has Lost Immunoglobulin Expression But Permits the Construction of Antibody-Secreting Hybrid Cell Lines, *The Journal of Immunology*, 123:1548-1550 (1979).

Kemp et al., Parathyroid Hormone-Related Protein of Malignancy: Active Synthetic Fragments, *Science* 238:1568-1570 (1987).

Kettleborough et al., Humanization of a Mouse Monoclonal Antibody by CDR-Grafting: The Importance of Framework Residues on Loop Conformation, *Protein Engineering*, 4:773-738 (1991).

Köhler et al., Derivation of Specific Antibody-Producing Tissue Culture and Tumor Lines by Cell Fusion, *European Journal of Immunology*, 6:511-519 (1976).

Kozak, At Least Six Nucleotides Preceding the AUG Initiator Condon Enhance Translation in Mammalian Cells, *Journal of Molecular Biology*, 196:947-950 (1987).

Kukreja et al., Tumor Resection and Antibodies to Parathyroid Hormone-Related Protein Cause Similar Changes on Bone Histomorphometry in Hypercalcemia of Cancer, Endocrinology 127(1):305-310 (1990).

Kukreja et al., Antibodies to Parathyroid Hormone-Related Protein Lower Serum Calcium in Athymic Mouse Models of Malignancy-Associated Hypercalcemia Due to Human Tumors, *The Journal of Clinical Investigation*, 82:1798-1802 (1988).

Liu, J.G., et al., "Developmental Role of PHTrP in Murine Molars," European Journal Oral Sciences 106 (suppl 1):143-146 (1998).

LoBuglio et al., Mouse/Human Chimeric Monoclonal Antibody in Man; Kinetics and Immune Response, *Proceedings of the National Academy of Sciences*, 86:4220-4224 (1989).

Lundgren et al., "Parathyroid Hormone (1-34) Receptor-Binding and Second-Messenger Response in Rat Incisor Odontoblasts", Calcif. Tissue Int., 62:255-259 (1998).

Maeda et al., Construction of Reshaped Human Antibodies with HIV-Neutralizing Activity, *Human Antibodies and Hybridomas*, 2:124-134 (1991).

Margulies et al., Somatic Cell Hybridization of Mouse Myeloma Cells, *Cell*, 8:405-415 (1976).

Marosi, C., et al., Fatal Encephalitis in a Patient with Chronic Graft-Versus Host Disease, *Bone Marrow Transplantation*, 6:53-57 (1990).

Mizushima et al., pEFBOS, A Powerful Mammalian Expression Vector, *Nucleic Acids Research*, 18:5322 (1990).

Morimoto, PTH/PTHrP, *Clinical Calcium* 5(12):50-54 (1995) (English Translation).

Moseley et al., Parathyroid Hormone-Related Protein Purified from A Human Lung Cancer Cell Line, *Proceedings of the National Academy of Sciences*, 84:5048-5052 (1987).

Mountain A. et al., "Engineering Antibodies for Therapy" In: Biotechnol *Genet Eng Rev*. 10:1-142 (1992).

Muller, J.M., et al., Uberwachung und Handhabung von Zentrainervosen und Intestinalen System zur Behandlung der Tumorkachexie, *Langenbecks Arch Chir Suppl II*, pp. 261-265, (1990) (English Abstract), Abstract only.

Mulligan et al, Synthesis of Rabbit β-globin in Cultured Monkey Kidney Cells Following Infection with a SV40 β-globin Recombinant Genome, *Nature*, 277:108-114 (1979).

Natsume et al., Binding Assay and Analysis of Kinetic Parameters by Bialcore Biosensor, *Experimental Medicine*, 13:85-91 (1995) (English Translation).

Ogata, E., "Parathyroid Hormone-Related Protein as a Potential Target of Therapy for Cancer-Associated Morbidity", *Cancer*, 88:2902-2911 (2000).

Ohtomo et al., Humanization of Mouse ONS-M21 Antibody with the Aid of Hybrid Variable Regions, *Molecular Immunology*, 32:407-416 (1995).

Olstad, O.K., et al., Expression and Characterization of a Recombinant Human Parathyroid Partial Agonist with Antagonistic Properties: Gly-hPTH(-1→+84), *Peptides*, 16:1031-1037 (1995).

Palmieri et al., "Muscle Calcium Accumulation in Muscular Dystrophy," *Intracell. Calcium Regul., Proc. Int. Symp.*, pp. 335-347 (1986).

Philbrick, et al, "Parathyroid Hormone-Related Protein is Required for Tooth Eruption", *Proc. Natl. Acad. Sci.* USA, 95:11846-11851 (1998).

Queen, C., et al., "A Humanized Antibody that Binds to the Interleukin 2 Receptor," *Proc. National Academy of Science USA*, 86:10029-10033 (1989).

Roe et al., A Photometric Method for the Determination of Insulin in Plasma and Urine, *Journal of Biological Chemistry*, 173:839-845 (1949).

Riechmann et al., Reshaping Human Antibodies for Therapy, *Nature*, 332:323-327 (1988).

Rosen et al., "The Effect of PTH Antagonist BIM-44002 on Serum Calcium and PTH Levels in Hypercalcemic Hyperparathyroid Patients", *Calcified Tissue international*, 61:455-459 (1997).

Roubini, E. et al., Synthesis of Fully Active Biotinylated Analogues of Parathyroid Hormone and Parathyroid Hormone-Related Protein as Tools for the Characterization of Parathyroid Hormone Receptors, *Biochemistry*, 31:4026-4033 (1992).

Sato et al., Passive Immunization with Anti-Parathyroid Hormone-related Monoclonal Antibody Markedly Prolongs Survival Time of Hypercalcemic Nude Mice Bearing Transplanted Human PTHrP-Producing Tumors, Journal of Bone and Mineral Research, 8:849-860 (1993).

Sato et al., Reshaping a Human Antibody to Inhibit the Interleukin 6-dependent Tumor Cell Growth, Cancer Research, 53:851-856 (1993).

Sato et al, A Highly Sensitive Bioassay for PTH Using ROS 17/2.8 Subclonal Cells, *Acta Endocrinologica*, 116:113-120 (1987).

Sato, Malignancy-associated Hypercalcemia: Pathogenesis and Treatment, *Journal of Tokyo Women's Medical College*, 58(9):939-946 (1988) (English Abstract).

Shingeno, C., PTH/PTHrP Receptor, Clinical Calcium, 5(3):79-83 (1995) (English Translation).

Shulman et al., A Better Cell Line for Making Hybridomas Secreting Specific Antibodies, *Nature*, 276:269-270 (1978).

Stewart et al., Clinical Review 16: Parathyroid Hormone-Related Proteins: Coming of Age in the 1990s, *Journal of Clinical Endocrinology and Metabolism*, 71:1410-1414 (1990).

Strewler, G.J., "The Physiology of Parathyroid Hormone-Related Protein," *The New England Journal of Medicine, Mechanisms of Disease* 342(3):177-185 (2000).

Sumiya et al., Hypercalcemia With Malignant Tumor, *Saishin Igaku*, 46(2):315-324 (1991).

Suva et al., A Parathyroid Hormone-Related Protein Implicated in Malignant Hypercalcemia: Cloning and Expression, *Science*, 237:893-896 (1987).

Takahashi et al., Structure of Human Immunoglobulin Gamma Genes: Implications for Evolution of a Gene Family, *Cell*, 29:671-679 (1982).

Takahashi et al., "Concentrations of Blood Parathyroid Hormone Related Protein (PTHrP) and Various Cytokines in Malignant Tumor Patients," *Record of the Japan Society of Clinical Biochemistry and Metabolism*, 35:107 (1998) (English Abstract).

Tanaka, R., Triple Paraneoplastic Syndrome of Hypercalcemia, Leukocytosis and Cachexia in Two Human Tumor Xerografts in Nude Mice, *Japanese Journal of Clinical Oncology*, 26:88-94 (1996).

Tempest et al., Reshaping A Human Monoclonal Antibody to Inhibit Human Respiraory Syncytial Virus Infection in vivo, *Bio/Technology*, 9:266-271 (1991).

Tenorio et al., "An Immunohistochemical Investigation of the Expression of Parathyroid Hormone Receptors in Rat Cementoblasts", *Archs Oral Biol.*, 41:299-305 (1996).

Tisdale, M.J., et al., Cancer Cachexia, *International Journal of Pancreatology*, 7:141-150 (1990).

Trowbridge, Interspecies Spleen-Myeloma Hybrid Producing Monoclonal Antibodies Against Mouse Lymphocyte Surface Glycoprotein, T200, *Journal of Experimental Medicine*, 148:313-323 (1978).

Verhoeyen et al., Reshaping Human Antibodies; Grafting an Antilysoyme Activity, *Science* 239:1534-1536 (1988).

Weissglas, M. et al., Hypercalcemia and Cosecretion of Interleukin-6 and Parathyroid Hormone Related Peptide by a Human Renal Cell Carcinoma Implanted into Nude Mice, The Journal of Urology 153:854-857 (1995).

Wong et al., Modulation of Antibody Affinity by an Engineered Amino Acid Substitution, *J. Immunol.* 154:(7):3351-8 (1995).

Yamamoto, S., et al., "Parathyroid Hormone-Related Peptide-(1-34) PTHrP-(134) Induces Vasopressin Release from the Rat Supraoptic Nucleus in Vitro through a Novel Receptor Distinct from a Type I or Type II PTH/PTHrP Receptor", Endocrinology, 138:2066-2072 (1997).

Yelton et al., Fusion of Mouse Myeloma and Spleen Cells, Lymphocyte Hybridomas, Second Workshop on "Functional Properties of Tumors of T and B Lymphocytes," Sponsored by the National Cancer Institute (NIH) 1-7 (1978).

Yoshida et al., "Study of Abnormal Calcium Level in Myotonic Dystrophy-Part II: with Respect to Nephrogenous Cyclic AMP and Immunoreactivity of Serum Parathyroid Hormone," The Japanese Endocrine Society Endocrine Journal, 64(7):539-547 (1988) (English Abstract).

Zbigniew Zylicz et al., Metabolic Response to Enteral Food in Different Phases of Cancer Cachexia in Rats, *Oncology*, 47:87-91 (1990).

Sabatini et al., "Increased Production of Tumor Necrosis Factor by Normal Immune Cells in a Model of the Humoral Hypercalcemia of Malignancy," *Laboratory Investigation*, 63(5), 676-682 (1990).

\* cited by examiner

NEUTRALIZING ACTIVITY OF HUMANIZED ANTI-PTHrP (1-34) ANTIBODY

NEUTRALIZING ACTIVITY OF HUMANIZED ANTI-PTHrP (1-34) ANTIBODY

SEQUENCE LISTING

<160> NUMBER OF SEQ ID NOS: 87

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
aaatagccct tgaccaggca                                        20

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
ctggttcggc ccacctctga aggttccaga atcgatag                    38

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
ggatcccggg ccagtggata gacagatg                               28

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
ggatcccggg tcagrggaag gtggraaca                              29

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
gttttcccag tcacgac                                           17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
caggaaacag ctatgac                                           17

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7

```
gtctaagctt ccaccatgaa acttcgggct c                              31
```

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8

```
tgttggatcc ctgcagagac agtgaccaga                                30
```

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9

```
gtctgaattc aagcttccac catggggttt gggctg                         36
```

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10

```
tttcccgggc ccttggtgga ggctgaggag acggtgacca g                   41
```

<210> SEQ ID NO 11
<211> LENGTH: 109
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11

```
gtctgaattc aagcttagta cttggccagc ccaaggccaa ccccacggtc accctgttcc     60
cgccctcctc tgaggagctc caagccaaca aggccacact agtgtgtct               109
```

<210> SEQ ID NO 12
<211> LENGTH: 110
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12

```
ggtttggtgg tctccactcc cgccttgacg gggctgccat ctgccttcca ggccactgtc     60
acagctcccg ggtagaagtc actgatcaga cacactagtg tggccttgtt              110
```

<210> SEQ ID NO 13
<211> LENGTH: 98
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
ggagtggaga ccaccaaacc ctccaaacag agcaacaaca agtacgcggc cagcagctac    60
ctgagcctga cgcccgagca gtggaagtcc cacagaag                            98

<210> SEQ ID NO 14
<211> LENGTH: 106
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
tgttgaattc ttactatgaa cattctgtag gggccactgt cttctccacg gtgctcccTt    60
catgcgtgac ctggcagctg tagcttctgt gggacttcca ctgctc                  106

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
gtctgaattc aagcttagta cttggccagc ccaaggccaa ccc                      43

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
tgttgaattc ttactatgaa                                                20

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
caacaagtac gcggccagca gctacctgag cctgacgcc                           39

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
gtagctgctg gccgcgtact tgttgttgct ctgtttgga                           39

<210> SEQ ID NO 19
<211> LENGTH: 46
<212> TYPE: DNA
<213> ORGANISM: Artificial Sequence

```
<220> FEATURE:
<223> OTHER INFORMATION: Description of Artificial Sequence: Synthetic
      DNA

<400> SEQUENCE: 19
gtctgaattc aagcttagtc ctaggtcgaa ctgtggctgc accatc                    46

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
tgttgaattc ttactaacac tctcccctgt tgaa                                 34

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
gtctaagctt ccaccatggc ctggactcct ctctt                                35

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
tgttgaattc agatctaact acttacctag gacagtgacc ttggtccc                  48

<210> SEQ ID NO 23
<211> LENGTH: 128
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
gtctaagctt ccaccatggg gtttgggctg agctgggttt tcctcgttgc tcttttaaga     60
ggtgtccagt gtcaggtgca gctggtggag tctgggggag gcgtggtcca gcctgggagg    120
tccctgag                                                             128

<210> SEQ ID NO 24
<211> LENGTH: 125
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
accattagta gtggtggtag ttacacctac tatccagaca gtgtgaaggg gcgattcacc     60
atctccagag acaattccaa gaacacgctg tatctgcaaa tgaacagcct gagagctgag    120
``` gacac                                                                125

<210> SEQ ID NO 25
<211> LENGTH: 132
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25
ctaccaccac tactaatggt tgccacccac tccagcccct tgcctggagc ctggcggacc    60
caagacatgc catagctact gaaggtgaat ccagaggctg cacaggagag tctcagggac   120
ctcccaggct gg                                                      132

<210> SEQ ID NO 26
<211> LENGTH: 110
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
tgttggatcc ctgaggagac ggtgaccagg gttccctggc cccagtaagc aaagtaagtc    60
atagtagtct gtctcgcaca gtaatacaca gccgtgtcct cagctctcag               110

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 27
gtctaagctt ccaccatggg gtttgggctg                                     30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
tgttggatcc ctgaggagac ggtgaccagg                                     30

<210> SEQ ID NO 29
<211> LENGTH: 133
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29
acaaagcttc caccatggcc tggactcctc tcttcttctt ctttgttctt cattgctcag    60
gttctttctc ccagcttgtg ctgactcaat cgccctctgc ctctgcctcc ctgggagcct   120
cggtcaagct cac                                                     133

<210> SEQ ID NO 30

<211> LENGTH: 118
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30
agcaagatgg aagccacagc acaggtgatg ggattcctga tcgcttctca ggctccagct     60
ctggggctga gcgctacctc accatctcca gcctccagtc tgaggatgag gctgacta     118

<210> SEQ ID NO 31
<211> LENGTH: 128
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
ctgtggcttc catcttgctt aagtttcatc aagtaccgag ggcccttctc tggctgctgc     60
tgatgccatt caatggtgta cgtactgtgc tgactactca aggtgcaggt gagcttgacc    120
gaggctcc                                                             128

<210> SEQ ID NO 32
<211> LENGTH: 114
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
cttggatccg ggctgaccta ggacggtcag tttggtccct ccgccgaaca ccctcacaaa     60
ttgttcctta attgtatcac ccacaccaca gtaatagtca gcctcatcct caga           114

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33
acaaagcttc caccatg                                                    17

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34
cttggatccg ggctgacct                                                  19

<210> SEQ ID NO 35
<211> LENGTH: 75
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35
cttggatccg ggctgaccta ggacggtcag tttggtccct ccgccgaaca cgtacacaaa    60
ttgttcctta attgt    75

<210> SEQ ID NO 36
<211> LENGTH: 43
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
aaaggatcct taagatccat caagtaccga gggggcttct ctg    43

<210> SEQ ID NO 37
<211> LENGTH: 46
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 37
acaaagctta gcgctacctc accatctcca gcctccagcc tgagga    46

<210> SEQ ID NO 38
<211> LENGTH: 111
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 38
cttggatccg ggctgaccta ggacggtcag tttggtccct ccgccgaaca cgtacacaaa    60
ttgttcctta attgtatcac ccacaccaca gatatagtca gcctcatcct c    111

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
cttctctggc tgctgctgat accattcaat ggtgtacgta ct    42

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
cgagggccct tctctggctg ctgctg    26

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
gagaagggcc ctargtacst gatgrawctt aagca                                      35

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
cacgaattca ctatcgattc tggaaccttc agagg                                      35

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43
ggcttggagc tcctcaga                                                         18

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 44
gacagtggtt caaagttttt                                                       20

<210> SEQ ID NO 45
<211> LENGTH: 118
<212> TYPE: PRT
<213> ORGANISM: Homo sapiens

<400> SEQUENCE: 45

Gln Leu Val Leu Thr Gln Ser Ser Ser Ala Ser Phe Ser Leu Gly Ala
 1               5                  10                  15

Ser Ala Lys Leu Thr Cys Thr Leu Ser Ser Gln His Ser Thr Tyr Thr
                20                  25                  30

Ile Glu Trp Tyr Gln Gln Pro Leu Lys Pro Lys Tyr Val Met
            35                  40                  45

Asp Leu Lys Gln Asp Gly Ser His Ser Thr Gly Asp Gly Ile Pro Asp
        50                  55                  60

Arg Phe Ser Gly Ser Ser Ser Gly Ala Asp Arg Tyr Leu Ser Ile Ser
 65                 70                  75                  80

Asn Ile Gln Pro Glu Asp Glu Ala Met Tyr Ile Cys Gly Val Gly Asp
                85                  90                  95

Thr Ile Lys Glu Gln Phe Val Tyr Val Phe Gly Gly Gly Thr Lys Val
            100                 105                 110

Thr Val Leu Gly Gln Pro
        115

```
<210> SEQ ID NO 46
<211> LENGTH: 118
<212> TYPE: PRT
<213> ORGANISM: Homo sapiens

<400> SEQUENCE: 46

Glu Val Gln Leu Val Glu Ser Gly Gly Asp Leu Val Lys Pro Gly Gly
  1               5                  10                  15

Ser Leu Lys Leu Ser Cys Ala Ala Ser Gly Phe Thr Phe Ser Ser Tyr
             20                  25                  30

Gly Met Ser Trp Ile Arg Gln Thr Pro Asp Lys Arg Leu Glu Trp Val
         35                  40                  45

Ala Thr Ile Ser Ser Gly Gly Ser Tyr Thr Tyr Tyr Pro Asp Ser Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Phe Tyr Cys
                 85                  90                  95

Ala Arg Gln Thr Thr Met Thr Tyr Phe Ala Tyr Trp Gly Gln Gly Thr
            100                 105                 110

Leu Val Thr Val Ser Ala
        115

<210> SEQ ID NO 47
<211> LENGTH: 116
<212> TYPE: PRT
<213> ORGANISM: Homo sapiens

<400> SEQUENCE: 47

Gln Leu Val Leu Thr Gln Ser Pro Ser Ala Ser Ala Ser Leu Gly Ala
  1               5                  10                  15

Ser Val Lys Leu Thr Cys Thr Leu Ser Ser Gln His Ser Thr Tyr Thr
             20                  25                  30

Ile Glu Trp His Gln Gln Pro Glu Lys Gly Pro Arg Tyr Leu Met
         35                  40                  45

Lys Leu Lys Gln Asp Gly Ser His Ser Thr Gly Asp Gly Ile Pro Asp
     50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Thr Ile Lys Glu Gln Phe Val Tyr Val Phe Gly Gly Gly Thr Lys Leu
            100                 105                 110

Thr Val Leu Gly
        115

<210> SEQ ID NO 48
<211> LENGTH: 118
<212> TYPE: PRT
<213> ORGANISM: Homo sapiens

<400> SEQUENCE: 48

Gln Leu Val Leu Thr Gln Ser Pro Ser Ala Ser Ala Ser Leu Gly Ala
  1               5                  10                  15

Ser Val Lys Leu Thr Cys Thr Leu Ser Ser Gln His Ser Thr Tyr Thr
             20                  25                  30

Ile Glu Trp Tyr Gln Gln Pro Glu Lys Gly Pro Lys Tyr Leu Met
         35                  40                  45
```

-continued

```
                35                  40                  45
Asp Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Thr Ile Lys Glu Gln Phe Val Tyr Val Phe Gly Gly Gly Thr Lys Leu
                100                 105                 110

Thr Val Leu Gly Gln Pro
        115

<210> SEQ ID NO 49
<211> LENGTH: 118
<212> TYPE: PRT
<213> ORGANISM: Homo sapiens

<400> SEQUENCE: 49

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Lys Tyr Val Met
             35                  40                  45

Asp Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Thr Ile Lys Glu Gln Phe Val Tyr Val Phe Gly Gly Gly Thr Lys Leu
                100                 105                 110

Thr Val Leu Gly Gln Pro
        115

<210> SEQ ID NO 50
<211> LENGTH: 118
<212> TYPE: PRT
<213> ORGANISM: Homo sapiens

<400> SEQUENCE: 50

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Arg Tyr Leu Met
             35                  40                  45

Asp Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Thr Ile Lys Glu Gln Phe Val Tyr Val Phe Gly Gly Gly Thr Lys Leu
                100                 105                 110

Thr Val Leu Gly Gln Pro
```

<210> SEQ ID NO 51
<211> LENGTH: 118
<212> TYPE: PRT
<213> ORGANISM: Homo sapiens

<400> SEQUENCE: 51

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Arg Tyr Val Met
        35                  40                  45

Asp Leu Lys Gln Asp Gly Ser His Ser Thr Gly Asp Gly Ile Pro Asp
    50                  55                  60

Arg Phe Ser Gly Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 52
<211> LENGTH: 118
<212> TYPE: PRT
<213> ORGANISM: Homo sapiens

<400> SEQUENCE: 52

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Lys Tyr Leu Met
        35                  40                  45

Asp Leu Lys Gln Asp Gly Ser His Ser Thr Gly Asp Gly Ile Pro Asp
    50                  55                  60

Arg Phe Ser Gly Ser Ser Gly Ala Glu Arg Tyr Leu Thr Ile Ser
65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 53
<211> LENGTH: 118
<212> TYPE: PRT
<213> ORGANISM: Homo sapiens

<400> SEQUENCE: 53

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

```
Ile Glu Trp Tyr Gln Gln Pro Glu Lys Gly Pro Arg Tyr Leu Met
        35                  40                  45

Asp Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 54
<211> LENGTH: 118
<212> TYPE: PRT
<213> ORGANISM: Homo sapiens

<400> SEQUENCE: 54

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Lys Tyr Val Met
        35                  40                  45

Asp Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 55
<211> LENGTH: 118
<212> TYPE: PRT
<213> ORGANISM: Homo sapiens

<400> SEQUENCE: 55

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Arg Tyr Val Met
        35                  40                  45

Asp Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110
```

```
Thr Val Leu Gly Gln Pro
        115

<210> SEQ ID NO 56
<211> LENGTH: 118
<212> TYPE: PRT
<213> ORGANISM: Homo sapiens

<400> SEQUENCE: 56

Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met Ser Trp Val Arg Gln Ala Pro Gly Lys Gly Leu Glu Trp Val
             35                  40                  45

Ala Thr Ile Ser Ser Gly Gly Ser Tyr Thr Tyr Tyr Pro Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gln Thr Thr Met Thr Tyr Phe Ala Tyr Trp Gly Gln Gly Thr
            100                 105                 110

Leu Val Thr Val Ser Ser
        115

<210> SEQ ID NO 57
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: sig_peptide
<222> LOCATION: (1)..(57)
<220> FEATURE:
<221> NAME/KEY: mat_peptide
<222> LOCATION: (58)..(411)

<400> SEQUENCE: 57 atg aac ttc ggg ctc agc ttg att ttc ctt gcc ctc att tta aaa ggt    48
Met Asn Phe Gly Leu Ser Leu Ile Phe Leu Ala Leu Ile Leu Lys Gly
            -15                 -10                  -5 gtc cag tgt gag gtg caa ctg gtg gag tct ggg gga gac tta gtg aag    96
Val Gln Cys Glu Val Gln Leu Val Glu Ser Gly Gly Asp Leu Val Lys
         -1   1               5                  10 cct gga ggg tcc ctg aaa ctc tcc tgt gca gcc tct gga ttc act ttc   144
Pro Gly Gly Ser Leu Lys Leu Ser Cys Ala Ala Ser Gly Phe Thr Phe
             15                  20                  25 agt agc tat ggc atg tct tgg att cgc cag act cca gac aag agg ctg   192
Ser Ser Tyr Gly Met Ser Trp Ile Arg Gln Thr Pro Asp Lys Arg Leu
         30                  35                  40                  45 gag tgg gtc gca acc att agt agt ggt ggt agt tac acc tac tat cca   240
Glu Trp Val Ala Thr Ile Ser Ser Gly Gly Ser Tyr Thr Tyr Tyr Pro
                 50                  55                  60 gac agt gtg aag ggg cga ttc acc atc tcc aga gac aat gcc aag aac   288
Asp Ser Val Lys Gly Arg Phe Thr Ile Ser Arg Asp Asn Ala Lys Asn
             65                  70                  75 acc cta tac ctg caa atg agc agt ctg aag tct gag gac aca gcc atg   336
Thr Leu Tyr Leu Gln Met Ser Ser Leu Lys Ser Glu Asp Thr Ala Met
```

```
            80                  85                  90
ttt tac tgt gca aga cag act act atg act tac ttt gct tac tgg ggc    384
Phe Tyr Cys Ala Arg Gln Thr Thr Met Thr Tyr Phe Ala Tyr Trp Gly
 95                 100                 105 caa ggg act ctg gtc act gtc tct gca                                411
Gln Gly Thr Leu Val Thr Val Ser Ala
110                 115

<210> SEQ ID NO 58
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: sig_peptide
<222> LOCATION: (1)..(57)
<220> FEATURE:
<221> NAME/KEY: mat_peptide
<222> LOCATION: (58)..(411)

<400> SEQUENCE: 58 atg ggg ttt ggg ctg agc tgg gtt ttc ctc gtt gct ctt tta aga ggt    48
Met Gly Phe Gly Leu Ser Trp Val Phe Leu Val Ala Leu Leu Arg Gly
            -15                 -10                  -5 gtc cag tgt cag gtg cag ctg gtg gag tct ggg gga ggc gtg gtc cag    96
Val Gln Cys Gln Val Gln Leu Val Glu Ser Gly Gly Gly Val Val Gln
     -1   1               5                  10 cct ggg agg tcc ctg aga ctc tcc tgt gca gcc tct gga ttc acc ttc    144
Pro Gly Arg Ser Leu Arg Leu Ser Cys Ala Ala Ser Gly Phe Thr Phe
 15                  20                  25 agt agc tat ggc atg tct tgg gtc cgc cag gct cca ggc aag ggg ctg    192
Ser Ser Tyr Gly Met Ser Trp Val Arg Gln Ala Pro Gly Lys Gly Leu
 30                  35                  40                  45 gag tgg gtg gca acc att agt agt ggt ggt agt tac acc tac tat cca    240
Glu Trp Val Ala Thr Ile Ser Ser Gly Gly Ser Tyr Thr Tyr Tyr Pro
                 50                  55                  60 gac agt gtg aag ggg cga ttc acc atc tcc aga gac aat tcc aag aac    288
Asp Ser Val Lys Gly Arg Phe Thr Ile Ser Arg Asp Asn Ser Lys Asn
             65                  70                  75 acg ctg tat ctg caa atg aac agc ctg aga gct gag gac acg gct gtg    336
Thr Leu Tyr Leu Gln Met Asn Ser Leu Arg Ala Glu Asp Thr Ala Val
         80                  85                  90 tat tac tgt gcg aga cag act act atg act tac ttt gct tac tgg ggc    384
Tyr Tyr Cys Ala Arg Gln Thr Thr Met Thr Tyr Phe Ala Tyr Trp Gly
 95                 100                 105 cag gga acc ctg gtc acc gtc tcc tca                                411
Gln Gly Thr Leu Val Thr Val Ser Ser
110                 115

<210> SEQ ID NO 59
<211> LENGTH: 11
<212> TYPE: PRT
<213> ORGANISM: Homo sapiens

<400> SEQUENCE: 59

Lys Ala Ser Gln Asp Val Asn Thr Ala Val Ala
 1               5                  10

<210> SEQ ID NO 60
<211> LENGTH: 7
<212> TYPE: PRT
<213> ORGANISM: Homo sapiens
```

<400> SEQUENCE: 60

Ser Ala Ser Asn Arg Tyr Thr
1               5

<210> SEQ ID NO 61
<211> LENGTH: 9
<212> TYPE: PRT
<213> ORGANISM: Homo sapiens

<400> SEQUENCE: 61

Gln Gln His Tyr Ser Thr Pro Phe Thr
1               5

<210> SEQ ID NO 62
<211> LENGTH: 5
<212> TYPE: PRT
<213> ORGANISM: Homo sapiens

<400> SEQUENCE: 62

Pro Tyr Trp Met Gln
1               5

<210> SEQ ID NO 63
<211> LENGTH: 16
<212> TYPE: PRT
<213> ORGANISM: Homo sapiens

<400> SEQUENCE: 63

Ser Ile Phe Gly Asp Gly Asp Thr Arg Tyr Ser Gln Lys Phe Lys Gly
1               5                   10                  15

<210> SEQ ID NO 64
<211> LENGTH: 11
<212> TYPE: PRT
<213> ORGANISM: Homo sapiens

<400> SEQUENCE: 64

Gly Leu Arg Arg Gly Gly Tyr Tyr Phe Asp Tyr
1               5                   10

<210> SEQ ID NO 65
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: sig_peptide
<222> LOCATION: (1)..(57)
<220> FEATURE:
<221> NAME/KEY: mat_peptide
<222> LOCATION: (58)..(411)

<400> SEQUENCE: 65 atg gcc tgg act cct ctc ttc ttc ttt gtt ctt cat tgc tca ggt        48
Met Ala Trp Thr Pro Leu Phe Phe Phe Val Leu His Cys Ser Gly
            -15                 -10                 -5 tct ttc tcc caa ctt gtg ctc act cag tca tct tca gcc tct ttc tcc    96
Ser Phe Ser Gln Leu Val Leu Thr Gln Ser Ser Ser Ala Ser Phe Ser
        -1   1               5                   10 ctg gga gcc tca gca aaa ctc acg tgc acc ttg agt agt cag cac agt   144
Leu Gly Ala Ser Ala Lys Leu Thr Cys Thr Leu Ser Ser Gln His Ser
        15                  20                  25

| | | |
|---|---|---|
| acg tac acc att gaa tgg tat cag caa cag cca ctc aag cct cct aag<br>Thr Tyr Thr Ile Glu Trp Tyr Gln Gln Gln Pro Leu Lys Pro Pro Lys<br>30                          35                    40                      45 | 192 |
| tat gtg atg gat ctt aag caa gat gga agc cac agc aca ggt gat ggg<br>Tyr Val Met Asp Leu Lys Gln Asp Gly Ser His Ser Thr Gly Asp Gly<br>                50                         55                      60 | 240 |
| att cct gat cgc ttc tct gga tcc agc tct ggt gct gat cgc tac ctt<br>Ile Pro Asp Arg Phe Ser Gly Ser Ser Ser Gly Ala Asp Arg Tyr Leu<br>                      65                         70                    75 | 288 |
| agc att tcc aac atc cag cca gaa gat gaa gca atg tac atc tgt ggt<br>Ser Ile Ser Asn Ile Gln Pro Glu Asp Glu Ala Met Tyr Ile Cys Gly<br>        80                         85                         90 | 336 |
| gtg ggt gat aca att aag gaa caa ttt gtg tat gtt ttc ggc ggt ggg<br>Val Gly Asp Thr Ile Lys Glu Gln Phe Val Tyr Val Phe Gly Gly Gly<br>    95                        100                    105 | 384 |
| acc aag gtc act gtc cta ggt cag ccc<br>Thr Lys Val Thr Val Leu Gly Gln Pro<br>110                115 | 411 |

<210> SEQ ID NO 66
<211> LENGTH: 405
<212> TYPE: DNA
<213> ORGANISM: Homo sapiens
<220> FEATURE:
<221> NAME/KEY: CDS
<222> LOCATION: (1)..(405)
<220> FEATURE:
<221> NAME/KEY: sig_peptide
<222> LOCATION: (1)..(57)
<220> FEATURE:
<221> NAME/KEY: mat_peptide
<222> LOCATION: (58)..(405)

<400> SEQUENCE: 66

| | | |
|---|---|---|
| atg gcc tgg act cct ctc ttc ttc ttc ttt gtt ctt cat tgc tca ggt<br>Met Ala Trp Thr Pro Leu Phe Phe Phe Phe Val Leu His Cys Ser Gly<br>                    -15                          -10                     -5 | 48 |
| tct ttc tcc cag ctt gtg ctg act caa tcg ccc tct gcc tct gcc tcc<br>Ser Phe Ser Gln Leu Val Leu Thr Gln Ser Pro Ser Ala Ser Ala Ser<br>    -1   1                  5                           10 | 96 |
| ctg gga gcc tcg gtc aag ctc acc tgc acc ttg agt agt cag cac agt<br>Leu Gly Ala Ser Val Lys Leu Thr Cys Thr Leu Ser Ser Gln His Ser<br>    15                        20                      25 | 144 |
| acg tac acc att gaa tgg cat cag cag cag cca gag aag ggc cct cgg<br>Thr Tyr Thr Ile Glu Trp His Gln Gln Gln Pro Glu Lys Gly Pro Arg<br>30                          35                    40                      45 | 192 |
| tac ttg atg aaa ctt aag caa gat gga agc cac agc aca ggt gat ggg<br>Tyr Leu Met Lys Leu Lys Gln Asp Gly Ser His Ser Thr Gly Asp Gly<br>                50                         55                      60 | 240 |
| att cct gat cgc ttc tca ggc tcc agc tct ggg gct gag cgc tac ctc<br>Ile Pro Asp Arg Phe Ser Gly Ser Ser Ser Gly Ala Glu Arg Tyr Leu<br>                      65                         70                    75 | 288 |
| acc atc tcc agc ctc cag tct gag gat gag gct gac tat tac tgt ggt<br>Thr Ile Ser Ser Leu Gln Ser Glu Asp Glu Ala Asp Tyr Tyr Cys Gly<br>        80                         85                         90 | 336 |
| gtg ggt gat aca att aag gaa caa ttt gtg tac gtg ttc ggc gga ggg<br>Val Gly Asp Thr Ile Lys Glu Gln Phe Val Tyr Val Phe Gly Gly Gly<br>    95                        100                    105 | 384 |
| acc aaa ctg acc gtc cta ggt<br>Thr Lys Leu Thr Val Leu Gly<br>110                115 | 405 |

<210> SEQ ID NO 67

<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: sig_peptide
<222> LOCATION: (1)..(57)
<220> FEATURE:
<221> NAME/KEY: mat_peptide
<222> LOCATION: (58)..(411)

<400> SEQUENCE: 67

```
atg gcc tgg act cct ctc ttc ttc ttt gtt ctt cat tgc tca ggt        48
Met Ala Trp Thr Pro Leu Phe Phe Phe Val Leu His Cys Ser Gly
            -15                 -10                 -5 tct ttc tcc cag ctt gtg ctg act caa tcg ccc tct gcc tct gcc tcc    96
Ser Phe Ser Gln Leu Val Leu Thr Gln Ser Pro Ser Ala Ser Ala Ser
     -1  1                   5                  10 ctg gga gcc tcg gtc aag ctc acc tgc acc ttg agt agt cag cac agt   144
Leu Gly Ala Ser Val Lys Leu Thr Cys Thr Leu Ser Ser Gln His Ser
         15                  20                  25 acg tac acc att gaa tgg tat cag cag cag cca gag aag ggc cct aag   192
Thr Tyr Thr Ile Glu Trp Tyr Gln Gln Gln Pro Glu Lys Gly Pro Lys
 30                  35                  40                  45 tac ctg atg gat ctt aag caa gat gga agc cac agc aca ggt gat ggg   240
Tyr Leu Met Asp Leu Lys Gln Asp Gly Ser His Ser Thr Gly Asp Gly
                 50                  55                  60 att cct gat cgc ttc tca ggc tcc agc tct ggg gct gag cgc tac ctc   288
Ile Pro Asp Arg Phe Ser Gly Ser Ser Ser Gly Ala Glu Arg Tyr Leu
             65                  70                  75 acc atc tcc agc ctc cag tct gag gat gag gct gac tat tac tgt ggt   336
Thr Ile Ser Ser Leu Gln Ser Glu Asp Glu Ala Asp Tyr Tyr Cys Gly
         80                  85                  90 gtg ggt gat aca att aag gaa caa ttt gtg tac gtg ttc ggc gga ggg   384
Val Gly Asp Thr Ile Lys Glu Gln Phe Val Tyr Val Phe Gly Gly Gly
     95                 100                 105 acc aaa ctg acc gtc cta ggc cag ccc                               411
Thr Lys Leu Thr Val Leu Gly Gln Pro
110                 115
```

<210> SEQ ID NO 68
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: sig_peptide
<222> LOCATION: (1)..(57)
<220> FEATURE:
<221> NAME/KEY: mat_peptide
<222> LOCATION: (58)..(411)

<400> SEQUENCE: 68

```
atg gcc tgg act cct ctc ttc ttc ttt gtt ctt cat tgc tca ggt        48
Met Ala Trp Thr Pro Leu Phe Phe Phe Val Leu His Cys Ser Gly
            -15                 -10                 -5 tct ttc tcc cag ctt gtg ctg act caa tcg ccc tct gcc tct gcc tcc    96
Ser Phe Ser Gln Leu Val Leu Thr Gln Ser Pro Ser Ala Ser Ala Ser
     -1  1                   5                  10 ctg gga gcc tcg gtc aag ctc acc tgc acc ttg agt agt cag cac agt   144
Leu Gly Ala Ser Val Lys Leu Thr Cys Thr Leu Ser Ser Gln His Ser
         15                  20                  25
```

| | | | | | | | | | | | | | | |
|---|---|---|---|---|---|---|---|---|---|---|---|---|---|---|
| acg | tac | acc | att | gaa | tgg | tat | cag | cag | cag | cca | gag | aag | ggc | cct | aag | 192
| Thr | Tyr | Thr | Ile | Glu | Trp | Tyr | Gln | Gln | Gln | Pro | Glu | Lys | Gly | Pro | Lys
|  |  | 30 |  |  | 35 |  |  |  | 40 |  |  |  | 45 |  |

```
acg tac acc att gaa tgg tat cag cag cag cca gag aag ggc cct aag      192
Thr Tyr Thr Ile Glu Trp Tyr Gln Gln Gln Pro Glu Lys Gly Pro Lys
            30              35                  40              45 tac gtg atg gat ctt aag caa gat gga agc cac agc aca ggt gat ggg      240
Tyr Val Met Asp Leu Lys Gln Asp Gly Ser His Ser Thr Gly Asp Gly
                    50                  55                  60 att cct gat cgc ttc tca ggc tcc agc tct ggg gct gag cgc tac ctc      288
Ile Pro Asp Arg Phe Ser Gly Ser Ser Ser Gly Ala Glu Arg Tyr Leu
                65                  70                  75 acc atc tcc agc ctc cag tct gag gat gag gct gac tat tac tgt ggt      336
Thr Ile Ser Ser Leu Gln Ser Glu Asp Glu Ala Asp Tyr Tyr Cys Gly
                80                  85                  90 gtg ggt gat aca att aag gaa caa ttt gtg tac gtg ttc ggc gga ggg      384
Val Gly Asp Thr Ile Lys Glu Gln Phe Val Tyr Val Phe Gly Gly Gly
        95                  100                 105 acc aaa ctg acc gtc cta ggc cag ccc                                  411
Thr Lys Leu Thr Val Leu Gly Gln Pro
110             115

<210> SEQ ID NO 69
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: sig_peptide
<222> LOCATION: (1)..(57)
<220> FEATURE:
<221> NAME/KEY: mat_peptide
<222> LOCATION: (58)..(411)

<400> SEQUENCE: 69 atg gcc tgg act cct ctc ttc ttc ttt gtt ctt cat tgc tca ggt           48
Met Ala Trp Thr Pro Leu Phe Phe Phe Val Leu His Cys Ser Gly
            -15                 -10                 -5 tct ttc tcc cag ctt gtg ctg act caa tcg ccc tct gcc tct gcc tcc      96
Ser Phe Ser Gln Leu Val Leu Thr Gln Ser Pro Ser Ala Ser Ala Ser
    -1  1                   5                   10 ctg gga gcc tcg gtc aag ctc acc tgc acc ttg agt agt cag cac agt     144
Leu Gly Ala Ser Val Lys Leu Thr Cys Thr Leu Ser Ser Gln His Ser
        15                  20                  25 acg tac acc att gaa tgg tat cag cag cag cca gag aag ggc cct agg     192
Thr Tyr Thr Ile Glu Trp Tyr Gln Gln Gln Pro Glu Lys Gly Pro Arg
            30                  35                  40              45 tac ctg atg gat ctt aag caa gat gga agc cac agc aca ggt gat ggg     240
Tyr Leu Met Asp Leu Lys Gln Asp Gly Ser His Ser Thr Gly Asp Gly
                    50                  55                  60 att cct gat cgc ttc tca ggc tcc agc tct ggg gct gag cgc tac ctc     288
Ile Pro Asp Arg Phe Ser Gly Ser Ser Ser Gly Ala Glu Arg Tyr Leu
                65                  70                  75 acc atc tcc agc ctc cag tct gag gat gag gct gac tat tac tgt ggt     336
Thr Ile Ser Ser Leu Gln Ser Glu Asp Glu Ala Asp Tyr Tyr Cys Gly
                80                  85                  90 gtg ggt gat aca att aag gaa caa ttt gtg tac gtg ttc ggc gga ggg     384
Val Gly Asp Thr Ile Lys Glu Gln Phe Val Tyr Val Phe Gly Gly Gly
        95                  100                 105 acc aaa ctg acc gtc cta ggc cag ccc                                 411
Thr Lys Leu Thr Val Leu Gly Gln Pro
110             115
```

<210> SEQ ID NO 70
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: sig_peptide
<222> LOCATION: (1)..(57)
<220> FEATURE:
<221> NAME/KEY: mat_peptide
<222> LOCATION: (58)..(411)

<400> SEQUENCE: 70

```
atg gcc tgg act cct ctc ttc ttc ttc ttt gtt ctt cat tgc tca ggt        48
Met Ala Trp Thr Pro Leu Phe Phe Phe Phe Val Leu His Cys Ser Gly
            -15                 -10                  -5 tct ttc tcc cag ctt gtg ctg act caa tcg ccc tct gcc tct gcc tcc        96
Ser Phe Ser Gln Leu Val Leu Thr Gln Ser Pro Ser Ala Ser Ala Ser
         -1   1               5                  10 ctg gga gcc tcg gtc aag ctc acc tgc acc ttg agt agt cag cac agt       144
Leu Gly Ala Ser Val Lys Leu Thr Cys Thr Leu Ser Ser Gln His Ser
 15                  20                  25 acg tac acc att gaa tgg tat cag cag cag cca gag aag ggc cct agg       192
Thr Tyr Thr Ile Glu Trp Tyr Gln Gln Gln Pro Glu Lys Gly Pro Arg
 30                  35                  40                  45 tac gtg atg gat ctt aag caa gat gga agc cac agc aca ggt gat ggg       240
Tyr Val Met Asp Leu Lys Gln Asp Gly Ser His Ser Thr Gly Asp Gly
                 50                  55                  60 att cct gat cgc ttc tca ggc tcc agc tct ggg gct gag cgc tac ctc       288
Ile Pro Asp Arg Phe Ser Gly Ser Ser Ser Gly Ala Glu Arg Tyr Leu
             65                  70                  75 acc atc tcc agc ctc cag tct gag gat gag gct gac tat tac tgt ggt       336
Thr Ile Ser Ser Leu Gln Ser Glu Asp Glu Ala Asp Tyr Tyr Cys Gly
         80                  85                  90 gtg ggt gat aca att aag gaa caa ttt gtg tac gtg ttc ggc gga ggg       384
Val Gly Asp Thr Ile Lys Glu Gln Phe Val Tyr Val Phe Gly Gly Gly
     95                 100                 105 acc aaa ctg acc gtc cta ggc cag ccc                                   411
Thr Lys Leu Thr Val Leu Gly Gln Pro
110                 115
```

<210> SEQ ID NO 71
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: sig_peptide
<222> LOCATION: (1)..(57)
<220> FEATURE:
<221> NAME/KEY: mat_peptide
<222> LOCATION: (58)..(411)

<400> SEQUENCE: 71

```
atg gcc tgg act cct ctc ttc ttc ttc ttt gtt ctt cat tgc tca ggt        48
Met Ala Trp Thr Pro Leu Phe Phe Phe Phe Val Leu His Cys Ser Gly
            -15                 -10                  -5 tct ttc tcc cag ctt gtg ctg act caa tcg ccc tct gcc tct gcc tcc        96
Ser Phe Ser Gln Leu Val Leu Thr Gln Ser Pro Ser Ala Ser Ala Ser
         -1   1               5                  10 ctg gga gcc tcg gtc aag ctc acc tgc acc ttg agt agt cag cac agt       144
Leu Gly Ala Ser Val Lys Leu Thr Cys Thr Leu Ser Ser Gln His Ser
```

```
                15                  20                  25
acg tac acc att gaa tgg tat cag cag cag cca gag aag ggc cct aag        192
Thr Tyr Thr Ile Glu Trp Tyr Gln Gln Gln Pro Glu Lys Gly Pro Lys
 30                  35                  40                  45 tac ctg atg gat ctt aag caa gat gga agc cac agc aca ggt gat ggg        240
Tyr Leu Met Asp Leu Lys Gln Asp Gly Ser His Ser Thr Gly Asp Gly
                 50                  55                  60 att cct gat cgc ttc tca ggc tcc agc tct ggg gct gag cgc tac ctc        288
Ile Pro Asp Arg Phe Ser Gly Ser Ser Ser Gly Ala Glu Arg Tyr Leu
                 65                  70                  75 acc atc tcc agc ctc cag tct gag gat gag gct gac tat atc tgt ggt        336
Thr Ile Ser Ser Leu Gln Ser Glu Asp Glu Ala Asp Tyr Ile Cys Gly
                 80                  85                  90 gtg ggt gat aca att aag gaa caa ttt gtg tac gtg ttc ggc gga ggg        384
Val Gly Asp Thr Ile Lys Glu Gln Phe Val Tyr Val Phe Gly Gly Gly
             95                 100                 105 acc aaa ctg acc gtc cta ggc cag ccc                                    411
Thr Lys Leu Thr Val Leu Gly Gln Pro
110                 115

<210> SEQ ID NO 72
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: sig_peptide
<222> LOCATION: (1)..(57)
<220> FEATURE:
<221> NAME/KEY: mat_peptide
<222> LOCATION: (58)..(411)

<400> SEQUENCE: 72 atg gcc tgg act cct ctc ttc ttc ttt gtt ctt cat tgc tca ggt             48
Met Ala Trp Thr Pro Leu Phe Phe Phe Val Leu His Cys Ser Gly
                 -15                 -10                  -5 tct ttc tcc cag ctt gtg ctg act caa tcg ccc tct gcc tct gcc tcc         96
Ser Phe Ser Gln Leu Val Leu Thr Gln Ser Pro Ser Ala Ser Ala Ser
         -1   1                   5                  10 ctg gga gcc tcg gtc aag ctc acc tgc acc ttg agt agt cag cac agt        144
Leu Gly Ala Ser Val Lys Leu Thr Cys Thr Leu Ser Ser Gln His Ser
 15                  20                  25 acg tac acc att gaa tgg tat cag cag cag cca gag aag ggc cct agg        192
Thr Tyr Thr Ile Glu Trp Tyr Gln Gln Gln Pro Glu Lys Gly Pro Arg
 30                  35                  40                  45 tac ctg atg gat ctt aag caa gat gga agc cac agc aca ggt gat ggg        240
Tyr Leu Met Asp Leu Lys Gln Asp Gly Ser His Ser Thr Gly Asp Gly
                 50                  55                  60 att cct gat cgc ttc tca ggc tcc agc tct ggg gct gag cgc tac ctc        288
Ile Pro Asp Arg Phe Ser Gly Ser Ser Ser Gly Ala Glu Arg Tyr Leu
                 65                  70                  75 acc atc tcc agc ctc cag tct gag gat gag gct gac tat atc tgt ggt        336
Thr Ile Ser Ser Leu Gln Ser Glu Asp Glu Ala Asp Tyr Ile Cys Gly
                 80                  85                  90 gtg ggt gat aca att aag gaa caa ttt gtg tac gtg ttc ggc gga ggg        384
Val Gly Asp Thr Ile Lys Glu Gln Phe Val Tyr Val Phe Gly Gly Gly
             95                 100                 105 acc aaa ctg acc gtc cta ggc cag ccc                                    411
Thr Lys Leu Thr Val Leu Gly Gln Pro
110                 115
```

<210> SEQ ID NO 73
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: sig_peptide
<222> LOCATION: (1)..(57)
<220> FEATURE:
<221> NAME/KEY: mat_peptide
<222> LOCATION: (58)..(411)

<400> SEQUENCE: 73

```
atg gcc tgg act cct ctc ttc ttc ttt gtt ctt cat tgc tca ggt         48
Met Ala Trp Thr Pro Leu Phe Phe Phe Val Leu His Cys Ser Gly
            -15                 -10                  -5 tct ttc tcc cag ctt gtg ctg act caa tcg ccc tct gcc tct gcc tcc    96
Ser Phe Ser Gln Leu Val Leu Thr Gln Ser Pro Ser Ala Ser Ala Ser
        -1   1                5                  10 ctg gga gcc tcg gtc aag ctc acc tgc acc ttg agt agt cag cac agt   144
Leu Gly Ala Ser Val Lys Leu Thr Cys Thr Leu Ser Ser Gln His Ser
 15                  20                  25 acg tac acc att gaa tgg tat cag cag cag cca gag aag ggc cct aag   192
Thr Tyr Thr Ile Glu Trp Tyr Gln Gln Gln Pro Glu Lys Gly Pro Lys
 30                  35                  40                  45 tac gtg atg gat ctt aag caa gat gga agc cac agc aca ggt gat ggg   240
Tyr Val Met Asp Leu Lys Gln Asp Gly Ser His Ser Thr Gly Asp Gly
                 50                  55                  60 att cct gat cgc ttc tca ggc tcc agc tct ggg gct gag cgc tac ctc   288
Ile Pro Asp Arg Phe Ser Gly Ser Ser Ser Gly Ala Glu Arg Tyr Leu
                 65                  70                  75 acc atc tcc agc ctc cag tct gag gat gag gct gac tat atc tgt ggt   336
Thr Ile Ser Ser Leu Gln Ser Glu Asp Glu Ala Asp Tyr Ile Cys Gly
             80                  85                  90 gtg ggt gat aca att aag gaa caa ttt gtg tac gtg ttc ggc gga ggg   384
Val Gly Asp Thr Ile Lys Glu Gln Phe Val Tyr Val Phe Gly Gly Gly
 95                 100                 105 acc aaa ctg acc gtc cta ggc cag ccc                               411
Thr Lys Leu Thr Val Leu Gly Gln Pro
110                 115
```

<210> SEQ ID NO 74
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: sig_peptide
<222> LOCATION: (1)..(57)
<220> FEATURE:
<221> NAME/KEY: mat_peptide
<222> LOCATION: (58)..(411)

<400> SEQUENCE: 74

```
atg gcc tgg act cct ctc ttc ttc ttt gtt ctt cat tgc tca ggt         48
Met Ala Trp Thr Pro Leu Phe Phe Phe Val Leu His Cys Ser Gly
            -15                 -10                  -5 tct ttc tcc cag ctt gtg ctg act caa tcg ccc tct gcc tct gcc tcc    96
Ser Phe Ser Gln Leu Val Leu Thr Gln Ser Pro Ser Ala Ser Ala Ser
        -1   1                5                  10 ctg gga gcc tcg gtc aag ctc acc tgc acc ttg agt agt cag cac agt   144
Leu Gly Ala Ser Val Lys Leu Thr Cys Thr Leu Ser Ser Gln His Ser
```

```
Leu Gly Ala Ser Val Lys Leu Thr Cys Thr Leu Ser Ser Gln His Ser
         15                  20                  25 acg tac acc att gaa tgg tat cag cag cag cca gag aag ggc cct agg       192
Thr Tyr Thr Ile Glu Trp Tyr Gln Gln Gln Pro Glu Lys Gly Pro Arg
 30                  35                  40                  45 tac gtg atg gat ctt aag caa gat gga agc cac agc aca ggt gat ggg       240
Tyr Val Met Asp Leu Lys Gln Asp Gly Ser His Ser Thr Gly Asp Gly
             50                  55                  60 att cct gat cgc ttc tca ggc tcc agc tct ggg gct gag cgc tac ctc       288
Ile Pro Asp Arg Phe Ser Gly Ser Ser Ser Gly Ala Glu Arg Tyr Leu
                 65                  70                  75 acc atc tcc agc ctc cag tct gag gat gag gct gac tat atc tgt ggt       336
Thr Ile Ser Ser Leu Gln Ser Glu Asp Glu Ala Asp Tyr Ile Cys Gly
         80                  85                  90 gtg ggt gat aca att aag gaa caa ttt gtg tac gtg ttc ggc gga ggg       384
Val Gly Asp Thr Ile Lys Glu Gln Phe Val Tyr Val Phe Gly Gly Gly
 95                 100                 105 acc aaa ctg acc gtc cta ggc cag ccc                                   411
Thr Lys Leu Thr Val Leu Gly Gln Pro
110                 115
```

<210> SEQ ID NO 75
<211> LENGTH: 34
<212> TYPE: PRT
<213> ORGANISM: Homo sapiens

<400> SEQUENCE: 75

```
Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
             20                  25                  30

Thr Ala
```

<210> SEQ ID NO 76
<211> LENGTH: 137
<212> TYPE: PRT
<213> ORGANISM: Homo sapiens

<400> SEQUENCE: 76

```
Met Asn Phe Gly Leu Ser Leu Ile Phe Leu Ala Leu Ile Leu Lys Gly
                -15                 -10                  -5

Val Gln Cys Glu Val Gln Leu Val Glu Ser Gly Gly Asp Leu Val Lys
         -1   1               5                  10

Pro Gly Gly Ser Leu Lys Leu Ser Cys Ala Ala Ser Gly Phe Thr Phe
 15                  20                  25

Ser Ser Tyr Gly Met Ser Trp Ile Arg Gln Thr Pro Asp Lys Arg Leu
 30                  35                  40                  45

Glu Trp Val Ala Thr Ile Ser Ser Gly Gly Ser Tyr Thr Tyr Tyr Pro
             50                  55                  60

Asp Ser Val Lys Gly Arg Phe Thr Ile Ser Arg Asp Asn Ala Lys Asn
                 65                  70                  75

Thr Leu Tyr Leu Gln Met Ser Ser Leu Lys Ser Glu Asp Thr Ala Met
         80                  85                  90

Phe Tyr Cys Ala Arg Gln Thr Thr Met Thr Tyr Phe Ala Tyr Trp Gly
 95                 100                 105

Gln Gly Thr Leu Val Thr Val Ser Ala
110                 115
```

```
<210> SEQ ID NO 77
<211> LENGTH: 137
<212> TYPE: PRT
<213> ORGANISM: Homo sapiens

<400> SEQUENCE: 77

Met Gly Phe Gly Leu Ser Trp Val Phe Leu Val Ala Leu Leu Arg Gly
                -15                 -10                  -5
Val Gln Cys Gln Val Gln Leu Val Glu Ser Gly Gly Gly Val Val Gln
         -1   1               5                  10
Pro Gly Arg Ser Leu Arg Leu Ser Cys Ala Ala Ser Gly Phe Thr Phe
         15                  20                  25
Ser Ser Tyr Gly Met Ser Trp Val Arg Gln Ala Pro Gly Lys Gly Leu
 30                  35                  40                  45
Glu Trp Val Ala Thr Ile Ser Ser Gly Ser Tyr Thr Tyr Tyr Pro
                 50                  55                  60
Asp Ser Val Lys Gly Arg Phe Thr Ile Ser Arg Asp Asn Ser Lys Asn
                 65                  70                  75
Thr Leu Tyr Leu Gln Met Asn Ser Leu Arg Ala Glu Asp Thr Ala Val
                 80                  85                  90
Tyr Tyr Cys Ala Arg Gln Thr Thr Met Thr Tyr Phe Ala Tyr Trp Gly
             95                 100                 105
Gln Gly Thr Leu Val Thr Val Ser Ser
110                 115

<210> SEQ ID NO 78
<211> LENGTH: 137
<212> TYPE: PRT
<213> ORGANISM: Homo sapiens

<400> SEQUENCE: 78

Met Ala Trp Thr Pro Leu Phe Phe Phe Val Leu His Cys Ser Gly
                -15                 -10                  -5
Ser Phe Ser Gln Leu Val Leu Thr Gln Ser Ser Ser Ala Ser Phe Ser
         -1   1               5                  10
Leu Gly Ala Ser Ala Lys Leu Thr Cys Thr Leu Ser Ser Gln His Ser
         15                  20                  25
Thr Tyr Thr Ile Glu Trp Tyr Gln Gln Gln Pro Leu Lys Pro Pro Lys
 30                  35                  40                  45
Tyr Val Met Asp Leu Lys Gln Asp Gly Ser His Ser Thr Gly Asp Gly
                 50                  55                  60
Ile Pro Asp Arg Phe Ser Gly Ser Ser Ser Gly Ala Asp Arg Tyr Leu
                 65                  70                  75
Ser Ile Ser Asn Ile Gln Pro Glu Asp Glu Ala Met Tyr Ile Cys Gly
                 80                  85                  90
Val Gly Asp Thr Ile Lys Glu Gln Phe Val Tyr Val Phe Gly Gly Gly
             95                 100                 105
Thr Lys Val Thr Val Leu Gly Gln Pro
110                 115

<210> SEQ ID NO 79
<211> LENGTH: 135
<212> TYPE: PRT
<213> ORGANISM: Homo sapiens

<400> SEQUENCE: 79

Met Ala Trp Thr Pro Leu Phe Phe Phe Val Leu His Cys Ser Gly
                -15                 -10                  -5
```

-continued

```
Ser Phe Ser Gln Leu Val Leu Thr Gln Ser Pro Ser Ala Ser Ala Ser
        -1   1               5                  10

Leu Gly Ala Ser Val Lys Leu Thr Cys Thr Leu Ser Ser Gln His Ser
         15                  20                  25

Thr Tyr Thr Ile Glu Trp His Gln Gln Pro Glu Lys Gly Pro Arg
 30              35                  40                  45

Tyr Leu Met Lys Leu Lys Gln Asp Gly Ser His Ser Thr Gly Asp Gly
                 50                  55                  60

Ile Pro Asp Arg Phe Ser Gly Ser Ser Ser Gly Ala Glu Arg Tyr Leu
                 65                  70                  75

Thr Ile Ser Ser Leu Gln Ser Glu Asp Glu Ala Asp Tyr Tyr Cys Gly
             80                  85                  90

Val Gly Asp Thr Ile Lys Glu Gln Phe Val Tyr Val Phe Gly Gly Gly
         95                 100                 105

Thr Lys Leu Thr Val Leu Gly
110                 115

<210> SEQ ID NO 80
<211> LENGTH: 137
<212> TYPE: PRT
<213> ORGANISM: Homo sapiens

<400> SEQUENCE: 80

Met Ala Trp Thr Pro Leu Phe Phe Phe Val Leu His Cys Ser Gly
             -15             -10                  -5

Ser Phe Ser Gln Leu Val Leu Thr Gln Ser Pro Ser Ala Ser Ala Ser
        -1   1               5                  10

Leu Gly Ala Ser Val Lys Leu Thr Cys Thr Leu Ser Ser Gln His Ser
         15                  20                  25

Thr Tyr Thr Ile Glu Trp Tyr Gln Gln Pro Glu Lys Gly Pro Lys
 30              35                  40                  45

Tyr Leu Met Asp Leu Lys Gln Asp Gly Ser His Ser Thr Gly Asp Gly
                 50                  55                  60

Ile Pro Asp Arg Phe Ser Gly Ser Ser Ser Gly Ala Glu Arg Tyr Leu
                 65                  70                  75

Thr Ile Ser Ser Leu Gln Ser Glu Asp Glu Ala Asp Tyr Tyr Cys Gly
             80                  85                  90

Val Gly Asp Thr Ile Lys Glu Gln Phe Val Tyr Val Phe Gly Gly Gly
         95                 100                 105

Thr Lys Leu Thr Val Leu Gly Gln Pro
110                 115

<210> SEQ ID NO 81
<211> LENGTH: 137
<212> TYPE: PRT
<213> ORGANISM: Homo sapiens

<400> SEQUENCE: 81

Met Ala Trp Thr Pro Leu Phe Phe Phe Val Leu His Cys Ser Gly
             -15             -10                  -5

Ser Phe Ser Gln Leu Val Leu Thr Gln Ser Pro Ser Ala Ser Ala Ser
        -1   1               5                  10

Leu Gly Ala Ser Val Lys Leu Thr Cys Thr Leu Ser Ser Gln His Ser
         15                  20                  25

Thr Tyr Thr Ile Glu Trp Tyr Gln Gln Pro Glu Lys Gly Pro Lys
 30              35                  40                  45
```

Tyr Val Met Asp Leu Lys Gln Asp Gly Ser His Ser Thr Gly Asp Gly
                50                  55                  60

Ile Pro Asp Arg Phe Ser Gly Ser Ser Ser Gly Ala Glu Arg Tyr Leu
            65                  70                  75

Thr Ile Ser Ser Leu Gln Ser Glu Asp Glu Ala Asp Tyr Tyr Cys Gly
        80                  85                  90

Val Gly Asp Thr Ile Lys Glu Gln Phe Val Tyr Val Phe Gly Gly Gly
    95                  100                 105

Thr Lys Leu Thr Val Leu Gly Gln Pro
110                 115

<210> SEQ ID NO 82
<211> LENGTH: 137
<212> TYPE: PRT
<213> ORGANISM: Homo sapiens

<400> SEQUENCE: 82

Met Ala Trp Thr Pro Leu Phe Phe Phe Val Leu His Cys Ser Gly
                -15                 -10                 -5

Ser Phe Ser Gln Leu Val Leu Thr Gln Ser Pro Ser Ala Ser Ala Ser
        -1  1                   5                   10

Leu Gly Ala Ser Val Lys Leu Thr Cys Thr Leu Ser Ser Gln His Ser
    15                  20                  25

Thr Tyr Thr Ile Glu Trp Tyr Gln Gln Pro Glu Lys Gly Pro Arg
30                  35                  40                  45

Tyr Leu Met Asp Leu Lys Gln Asp Gly Ser His Ser Thr Gly Asp Gly
                50                  55                  60

Ile Pro Asp Arg Phe Ser Gly Ser Ser Ser Gly Ala Glu Arg Tyr Leu
            65                  70                  75

Thr Ile Ser Ser Leu Gln Ser Glu Asp Glu Ala Asp Tyr Tyr Cys Gly
        80                  85                  90

Val Gly Asp Thr Ile Lys Glu Gln Phe Val Tyr Val Phe Gly Gly Gly
    95                  100                 105

Thr Lys Leu Thr Val Leu Gly Gln Pro
110                 115

<210> SEQ ID NO 83
<211> LENGTH: 137
<212> TYPE: PRT
<213> ORGANISM: Homo sapiens

<400> SEQUENCE: 83

Met Ala Trp Thr Pro Leu Phe Phe Phe Val Leu His Cys Ser Gly
                -15                 -10                 -5

Ser Phe Ser Gln Leu Val Leu Thr Gln Ser Pro Ser Ala Ser Ala Ser
        -1  1                   5                   10

Leu Gly Ala Ser Val Lys Leu Thr Cys Thr Leu Ser Ser Gln His Ser
    15                  20                  25

Thr Tyr Thr Ile Glu Trp Tyr Gln Gln Pro Glu Lys Gly Pro Arg
30                  35                  40                  45

Tyr Val Met Asp Leu Lys Gln Asp Gly Ser His Ser Thr Gly Asp Gly
                50                  55                  60

Ile Pro Asp Arg Phe Ser Gly Ser Ser Ser Gly Ala Glu Arg Tyr Leu
            65                  70                  75

Thr Ile Ser Ser Leu Gln Ser Glu Asp Glu Ala Asp Tyr Tyr Cys Gly
        80                  85                  90

```
Val Gly Asp Thr Ile Lys Glu Gln Phe Val Tyr Val Phe Gly Gly Gly
         95                 100                 105
Thr Lys Leu Thr Val Leu Gly Gln Pro
110                 115

<210> SEQ ID NO 84
<211> LENGTH: 137
<212> TYPE: PRT
<213> ORGANISM: Homo sapiens

<400> SEQUENCE: 84

Met Ala Trp Thr Pro Leu Phe Phe Phe Val Leu His Cys Ser Gly
            -15                 -10                  -5
Ser Phe Ser Gln Leu Val Leu Thr Gln Ser Pro Ser Ala Ser Ala Ser
         -1   1                   5                  10
Leu Gly Ala Ser Val Lys Leu Thr Cys Thr Leu Ser Ser Gln His Ser
         15                  20                  25
Thr Tyr Thr Ile Glu Trp Tyr Gln Gln Pro Glu Lys Gly Pro Lys
 30                  35                  40                  45
Tyr Leu Met Asp Leu Lys Gln Asp Gly Ser His Ser Thr Gly Asp Gly
                 50                  55                  60
Ile Pro Asp Arg Phe Ser Gly Ser Ser Ser Gly Ala Glu Arg Tyr Leu
                 65                  70                  75
Thr Ile Ser Ser Leu Gln Ser Glu Asp Glu Ala Asp Tyr Ile Cys Gly
             80                  85                  90
Val Gly Asp Thr Ile Lys Glu Gln Phe Val Tyr Val Phe Gly Gly Gly
         95                 100                 105
Thr Lys Leu Thr Val Leu Gly Gln Pro
110                 115

<210> SEQ ID NO 85
<211> LENGTH: 137
<212> TYPE: PRT
<213> ORGANISM: Homo sapiens

<400> SEQUENCE: 85

Met Ala Trp Thr Pro Leu Phe Phe Phe Val Leu His Cys Ser Gly
            -15                 -10                  -5
Ser Phe Ser Gln Leu Val Leu Thr Gln Ser Pro Ser Ala Ser Ala Ser
         -1   1                   5                  10
Leu Gly Ala Ser Val Lys Leu Thr Cys Thr Leu Ser Ser Gln His Ser
         15                  20                  25
Thr Tyr Thr Ile Glu Trp Tyr Gln Gln Pro Glu Lys Gly Pro Arg
 30                  35                  40                  45
Tyr Leu Met Asp Leu Lys Gln Asp Gly Ser His Ser Thr Gly Asp Gly
                 50                  55                  60
Ile Pro Asp Arg Phe Ser Gly Ser Ser Ser Gly Ala Glu Arg Tyr Leu
                 65                  70                  75
Thr Ile Ser Ser Leu Gln Ser Glu Asp Glu Ala Asp Tyr Ile Cys Gly
             80                  85                  90
Val Gly Asp Thr Ile Lys Glu Gln Phe Val Tyr Val Phe Gly Gly Gly
         95                 100                 105
Thr Lys Leu Thr Val Leu Gly Gln Pro
110                 115
```

```
<210> SEQ ID NO 86
<211> LENGTH: 137
<212> TYPE: PRT
<213> ORGANISM: Homo sapiens

<400> SEQUENCE: 86

Met Ala Trp Thr Pro Leu Phe Phe Phe Val Leu His Cys Ser Gly
                -15              -10                  -5
Ser Phe Ser Gln Leu Val Leu Thr Gln Ser Pro Ser Ala Ser Ala Ser
          -1   1               5                  10
Leu Gly Ala Ser Val Lys Leu Thr Cys Thr Leu Ser Ser Gln His Ser
         15                  20                  25
Thr Tyr Thr Ile Glu Trp Tyr Gln Gln Pro Glu Lys Gly Pro Lys
 30                  35                  40                  45
Tyr Val Met Asp Leu Lys Gln Asp Gly Ser His Ser Thr Gly Asp Gly
             50                  55                  60
Ile Pro Asp Arg Phe Ser Gly Ser Ser Ser Gly Ala Glu Arg Tyr Leu
             65                  70                  75
Thr Ile Ser Ser Leu Gln Ser Glu Asp Glu Ala Asp Tyr Ile Cys Gly
         80                  85                  90
Val Gly Asp Thr Ile Lys Glu Gln Phe Val Tyr Val Phe Gly Gly Gly
     95                 100                 105
Thr Lys Leu Thr Val Leu Gly Gln Pro
110                 115

<210> SEQ ID NO 87
<211> LENGTH: 137
<212> TYPE: PRT
<213> ORGANISM: Homo sapiens

<400> SEQUENCE: 87

Met Ala Trp Thr Pro Leu Phe Phe Phe Val Leu His Cys Ser Gly
                -15              -10                  -5
Ser Phe Ser Gln Leu Val Leu Thr Gln Ser Pro Ser Ala Ser Ala Ser
          -1   1               5                  10
Leu Gly Ala Ser Val Lys Leu Thr Cys Thr Leu Ser Ser Gln His Ser
         15                  20                  25
Thr Tyr Thr Ile Glu Trp Tyr Gln Gln Pro Glu Lys Gly Pro Arg
 30                  35                  40                  45
Tyr Val Met Asp Leu Lys Gln Asp Gly Ser His Ser Thr Gly Asp Gly
             50                  55                  60
Ile Pro Asp Arg Phe Ser Gly Ser Ser Ser Gly Ala Glu Arg Tyr Leu
             65                  70                  75
Thr Ile Ser Ser Leu Gln Ser Glu Asp Glu Ala Asp Tyr Ile Cys Gly
         80                  85                  90
Val Gly Asp Thr Ile Lys Glu Gln Phe Val Tyr Val Phe Gly Gly Gly
     95                 100                 105
Thr Lys Leu Thr Val Leu Gly Gln Pro
110                 115
```

THERAPEUTIC AGENT FOR CACHEXIA

This is a division of application Ser. No. 09/423,800, filed Nov. 12, 1999, abandoned on Jan. 9, 2003, which is the National Stage of PCT/JP98/02116, filed May 13, 1998, both of which are incorporated herein by reference.

TECHNICAL FIELD

The present invention relates to a therapeutic agent for cachexia comprising a substance capable of inhibiting the binding between parathyroid hormone related protein (PTHrP) and a receptor thereof as an active ingredient.

BACKGROUND ART

Cachexia found in terminal cancer patients is one of the common paraneoplastic syndromes of malignancy, and characterized by systemic disorders with anorexia, weight loss, anemia, electrolyte imbalance and compromised immune function as main symptoms. The development of cachexia in cancer patients leads to fatal and terminal symptoms; impairs the Quality-of-life (QOL) of the patients; and gives strong psychological, physical and social impacts on the patients and their families and surrounding people.

Recently, it has been found that cachectin, which is believed to be a causative agent of cancer cachexia, is identical to tumor necrosis factor (TNF). Thereafter, it has also been found that cytokines (e.g., interleukin (IL)-1, IL-6, LIF, IFN) also have the same actions as cachectin and thus cachexia is induced by composite action of multiple factors.

It has been known that OCC-1 cell line derived from human oral cavity carcinoma produces various types of liquid factors involved in cancer cachexia. A nude mouse implanted with OCC-1 cells comes to develop various syndromes including cachexia (Kajimura N. et al., Cancer Chemother. Pharmacol., 1996, 38 Suppl. pS48-52; Tanaka R. et al., Jpn. J. Clin. Oncology April 1996, 26 (2) p88-94). It has been believed that this is because the OCC-1 cell line implanted into the nude mouse produces various cytokines (e.g., G-CSF, IL-6, LIF, IL-11, PTHrP) with the growth of the cells, and these factors act compositely in the nude mouse to cause such symptoms.

The symptoms found in the OCC-1 cell line-implanted nude mouse appear to be highly similar to those experienced by human terminal cancer patients. However, there has been no report concerning the drugs or therapeutic agents for cachexia.

DISCLOSURE OF INVENTION

The object of the present invention is to provide a therapeutic agent for cachexia comprising, as an active ingredient, a substance capable of inhibiting the binding between parathyroid hormone related protein (PTHrP) and a receptor thereof.

The present inventors have made extensive and intensive studies on discovering such therapeutic agent. As a result, they found that development of a substance that can inhibit the binding between PTHrP and a receptor thereof could achieve such object. This finding leads the accomplishment of the invention.

That is, the present invention relates to a therapeutic agent for cachexia comprising, as an active ingredient, a substance capable of inhibiting the binding between PTHrP and a receptor thereof.

In the present invention, the term "cachexia" encompasses those induced by cancer.

The present invention relates to a therapeutic agent for cachexia comprising, as an active ingredient, a substance capable of inhibiting the binding between parathyroid hormone related protein (hereinafter, referred to as "PTHrP") and a receptor thereof (hereinafter, referred to as "PTHrP receptor").

As used herein, the term "PTHrP receptor" refers to any receptor which binds to PTHrP (such as those as described in Japanese National Phase Laid-open Publication No. 6-506598), regardless of whether the PTHrP receptor is present on a target organ (e.g., bone, kidney) or not.

As used herein, the term "a substance capable of inhibiting the binding between PTHrP and a receptor thereof (a PTHrP receptor)" refers to any substance that can bind to PTHrP to prevent the binding of the PTHrP to a PTHrP receptor, such as an anti-PTHrP antibody; any substance that can bind to a PTHrP receptor to prevent the binding of the PTHrP receptor to PTHrP, such as an antagonist against a PTHrP receptor (a PTHrP antagonist), specifically a peptide having replacement or deletion of at least one amino acid residue in the PTHrP peptide or a partial sequence of the PTHrP peptide; or a combination thereof.

The anti-PTHrP antibody includes those of any known types, such as a humanized antibody, a human antibody (WO 96/33735) or a chimeric antibody (Japanese Patent Application Laid-open No. 4-228089), and the antibody exemplary used in the present invention (#23-57-137-1 antibody). The antibody may be of polyclonal type or monoclonal type, but preferably of monoclonal type. The PTHrP antagonist includes a polypeptide or a low molecular weight substance. The PTHrP antagonist includes a substance that binds to a PTHrP receptor in an antagonistic manner against PTHrP, such as a polypeptide having a PTHrP antagonistic activity as described in Japanese Patent Application Laid-open No. 7-165790; Peptides (UNITED STATES), 1995, 16(6) 1031-1037; Biochemistry (UNITED STATES) April 281992, 31(16) 4026-4033; and Japanese National Phase Laid-open No. 5-509098. These polypeptides may have deletion, replacement, addition or insertion of at least one amino acid residue, as long as they can exhibit an equivalent level of PTHrP antagonistic activity, which are also encompassed in the PTHrP antagonists of the present invention.

Hereinbelow, the present invention will be described in detail exemplary using an anti-PTHrP antibody as the "substance capable of inhibiting the binding between PTHrP and a PTHrP receptor."

1. Anti-PTHrP Antibody

The anti-PTHrP antibody used in the present invention may be any one as long as it can exhibit a therapeutic effect on cachexia, regardless of its source, type (monoclonal or polyclonal) and configuration.

The anti-PTHrP antibody used in the present invention can be produced by any known method as a polyclonal or monoclonal antibody. Preferably, the anti-PTHrP antibody is a monoclonal antibody derived from a mammal. The monoclonal antibody from a mammal includes those produced from a hybridoma and those produced by a genetic engineering technique from a host transformed with a recombinant expression vector carrying a gene for the antibody. The antibody used in the present invention is one that can bind to PTHrP to prevent the binding of the PTHrP to a PTH/PTHrP receptor, thus blocking the signal transduction of the PTHrP and consequently inhibiting the biological activity of PTHrP.

A specific example of such antibody is #23-57-137-1 antibody which can be produced with a hybridoma clone #23-57-137-1.

The hybridoma clone #23-57-137-1 has been designated "mouse-mouse hybrodima #23-57-137-1" and deposited under the terms of the Budapest Treaty on Aug. 15, 1996 at the National Institute of Bioscience and Human-technology, Agency of Industrial Science and Technology, Japan (1-3, Higashi 1-chome, Tsukuba-shi, Ibaraki, Japan) under the accession No. FERM BP-5631.

2. Antibody-Producing Hybridoma

A monoclonal antibody-producing hybridoma can basically be produced by any known technique. That is, PTHrP is used as an antigen for immunization in accordance with a conventional immunization method. The resultant immunocytes are fused to known parent cells by a conventional cell fusion method, and monoclonal antibody-producing cells are screened from the fused cells by a conventional screening method.

More specifically, the monoclonal antibody-producing cell can be prepared as follows.

First, a human PTHrP, which is used as an sensitizing antigen for producing the antibody, is prepared by expressing the PTHrP gene/amino acid sequence disclosed in Suva, L. J. et al., Science (1987) 237, 893. That is, a nucleotide sequence encoding the PTHrP is inserted into any known expression vector, and a suitable host cell is transformed with the expression vector. The PTHrP protein is then isolated and purified from the transformed host cell or from a culture supernatant of the transformed host cell by any known method.

Second, the purified PTHrP protein is used as a sensitizing antigen. Alternatively, a 34-amino acid peptide of the N-terminal region of the PTHrP may be used as a sensitizing antigen, which can be chemically synthesized.

The mammal to be immunized with the sensitizing antigen is not particularly limited. However, the mammal is preferably selected taking into consideration of compatibility with the parent cell used for cell fusion. Generally, a rodent (e.g., mouse, rat, hamster, rabbit) or monkey may be used.

The immunization of the mammal with the sensitizing antigen can be performed in accordance with any known method, for example, by injecting the sensitizing antigen to a mammal intraperitoneally or subcutaneously. More specifically, the sensitizing antigen is diluted with and suspended to phosphate-buffered saline (PBS) or normal saline properly, the resultant suspension is then mixed with an appropriate amount of an adjuvant (e.g., Freund's complete adjuvant) to give an emulsion. The emulsion is injected to a mammal several times at intervals of 4 to 21 days. In the immunization, the sensitizing antigen may be attached to a suitable carrier.

After the immunization, the serum antibody level is checked. When the serum antibody level is confirmed to reach the desired level, immunocytes are isolated from the mammal and then subjected to cell fusion. A preferable immunocyte is a spleen cell.

The parent cell used for the cell fusion (i.e., the counterpart of the cell fusion with the immunocyte) is a myeloma cell derived from a mammal. The myeloma cell is of any known cell line, and, for example, P3 (P3x63Ag8.653) (J. Immunol. (1979) 123, 1548-1550), P3x63Ag8U.1 (Current Topics in Microbiology and Immunology (1978) 81, 1-7), NS-1 (Kohler, G. and Milstein, C. Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S., J. Exp. Med. (1978) 148, 313-323) or R210 (Galfre, G. et al., Nature (1979) 277, 131-133).

Cell fusion of the immunocyte to the myeloma cell is basically performed in accordance with any known method such as the method of Milstein et al. (Kohler, G. and Milstein, C., Methods Enzymol. (1981) 73, 3-46) may be preferably used.

More specifically, the cell fusion is performed, for example, in a conventional nutrient culture medium in the presence of a cell fusion promoter. The cell fusion promoter may be polyethylene glycol (PEG) or a Sendai virus (hemagglutinating virus of Japan; HVJ). If desired, for the purpose of improving the fusion efficiency, an additive such as dimethyl sulfoxide may also be incorporated.

The ratio between the immunocytes and the myeloma cells for the cell fusion may be any one. For example, the immunocytes are used in the amount 1-10 times larger than the myeloma cells. The culture medium used for the cell fusion is, for example, RPMI 1640 medium or MEM medium suitable for the growth of the myeloma cell line, or other medium conventionally used for the culture of such cells. If desired, a serum supplement, such as feral calf serum (FCS), may be added to the culture medium.

The cell fusion is performed by well mixing the immunocytes and the myeloma cells of given amounts in the culture medium, adding PEG solution (e.g., mean molecular weight: about 1000-6000) (which has been previously warmed to about 37° C.) thereto usually to a concentration of 30-60% (w/v), and then mixing the resultant solution, thereby giving fusion cells (hybridomas). Subsequently, an appropriate culture medium is added to the culture solution, and centrifuged to remove the supernatant. This procedure is repeated several times to remove the cell fusion promoter or the like that are undesirable for the growth of the hybridomas from the culture medium.

The obtained hybridomas can be selected by cultivating in a conventional selective medium, such as hypoxanthine-aminopterin-thymidine (HAT) medium. The cultivation of the hybridomas in HAT medium is performed for the time of period enough to cause to death of the cells other than the desired hybridomas (i.e., cells that fail to fuse), usually for several days to several weeks. Subsequently, a conventional limiting dilution method is performed to screen and monoclone the hybridomas that are secreting the desired antibody.

Alternatively, a human antibody having a binding activity against the PTHrP may be prepared by sensitizing a human lymphocyte with PTHrP in vitro, and then subjecting the sensitized lymphocyte to cell fusion to a human-derived myeloma cell capable of infinite growth (Japanese Patent Publication No. 1-59878). Alternatively, a human antibody against PTHrP may be prepared by injecting PTHrP as an antigen to a transgenic animal that has the entire repertories of the human antibody genes to give an anti-PTHrP antibody-producing cell, and immortalizing the cells, thus the human antibody can be produced from the immortalized cell (International Publication Nos. WO 94/25585, WO 93/12227, WO 92/03918 and WO 94/02602).

The monoclonal antibody-producing hybridoma prepared as above can be subcultured in a conventional culture medium and stored under liquid nitrogen for a long time of period.

For the production of a monoclonal antibody from the hybridoma, a method involving cultivating the hybridoma in accordance with a conventional method and collecting the monoclonal antibody from the culture supernatant, or a method involving injecting the hybridoma to a mammal compatible with the hybridoma to grow the hybridoma in the mammal body and collecting the hybridoma from the ascites of the mammal may be employed. The former method is suitable for producing the antibody in high purity, while the latter method is suitable for producing the antibody in a large amount.

3. Recombinant Antibody

In the present invention, a recombinant-type monoclonal antibody may also be used, which can be produced by cloning an antibody gene from the hybridoma, integrating the antibody gene into a suitable vector, introducing the vector into a host, and producing the antibody from the host according to a conventional genetic recombination technique (see, for example, Vandamme, A. M. et al., Eur. J. Biochem. (1990) 192, 767-775)

More specifically, mRNA encoding variable (V) region of an anti-PTHrP antibody is isolated from the anti-PTHrP antibody-producing hybridoma. The isolation of the mRNA is performed by preparing a total RNA by any known method, such as guanidium ultracentrifugation method (Chirgwin, J. M. et al., Biochemistry (1979) 18, 5294-5299) and AGPC method (Chomczynski, P. et al., Anal. Biochem. (1987) 162, 156-159), and then producing the desired mRNA from the total RNA using mRNA Purification Kit (Pharmacia) or the like. Alternatively, the mRNA may also be prepared directly using QuickPrep mRNA Purification Kit (Pharmacia).

Next, cDNA for the antibody V-region is synthesized from the mRNA with a reverse transcriptase. The synthesis of the cDNA is performed using AMV Reverse Transcriptase First-strand cDNA Synthesis Kit (Seikagaku Corporation) or the like. The cDNA may also be synthesized or amplified by 5'-RACE method (Frohman, M. A. et al., Proc. Natl. Acad. Sci. USA (1988) 85, 8998-9002; Belyavsky, A. et al., Nucleic Acids Res. (1989) 17, 2919-2932) using 5'-Ampli FINDER RACE Kit (Clontech) in combination with a PCR method, or the like.

A DNA fragment of interest is isolated and purified from the resultant PCR product and then ligated to a vector DNA to give a recombinant vector. The recombinant vector is introduced into a host such as E. coli, and a colony containing a desired recombinant vector is selected. The nucleotide sequence of the DNA of interest in the recombinant vector is confirmed by, for example, dideoxynucleotide chain termination method.

Once DNA encoding the anti-PTHrP antibody V-region is obtained, the DNA is integrated into an expression vector containing DNA encoding the antibody constant (C) region.

For the production of the anti-PTHrP antibody used in the present invention, the antibody gene is integrated into an expression vector so that the antibody gene can be expressed under the control of expression control regions (e.g., enhancer, promoter). A host cell is transformed with the expression vector to express the antibody.

In the expression of the antibody gene, DNA encoding heavy (H) chain and DNA encoding light (L) chain of the antibody may be integrated into separate expression vectors, and then a host cell is co-transformed with the resultant recombinant expression vectors. Alternatively, both DNA encoding H-chain and DNA encoding L-chain of the antibody may be integrated together into a single expression vector, and then a host cell is transformed with the resultant recombinant expression vector (WO 94/11523).

In the production of the recombinant antibody, besides the above-mentioned host cells, a transgenic animal may also be used as a host. For example, the antibody gene is inserted into a predetermined site of a gene encoding a protein inherently produced in the milk of an animal (e.g., goat β-casein) to give a fusion gene. A DNA fragment containing the antibody gene-introduced fusion gene is injected into an embryo of a goat, and the embryo is then introduced into a female goat. The female goat having the embryo therein bears a transgenic goat. The antibody of interest is secreted in the milk from the transgenic goat or a progeny thereof. For the purpose of increasing the amount of the antibody-containing milk, an appropriate hormone may be administered to the transgenic goat (Ebert, K. M. et al., Bio/Technology (1994) 12, 699-702).

4. Modified Antibody

In the present invention, for the purpose of reducing the heterogenisity against a human body or the like, an artificially modified recombinant antibody may be used, including a chimeric antibody and a humanized antibody. These modified antibodies can be prepared by any known method.

A chimeric antibody usable in the present invention can be prepared by ligating the DNA encoding the antibody V-region prepared as mentioned above to DNA encoding a human antibody C-region, integrating the ligation product into an expression vector, and introducing the resultant recombinant expression vector into a host to produce the chimeric antibody.

A humanized antibody is also referred to as "reshaped human antibody", in which the complementarity determining regions (CDRs) of an antibody of a non-human mammal (e.g., a mouse) are grafted to those of a human antibody. The general genetic recombination procedure for producing such humanized antibody is also known (EP 125023; WO 96/02576).

Specifically, a DNA sequence in which mouse antibody CDRs are ligated through framework regions (FRs) is designed, and synthesized by a PCR method using several oligonucleotides as primers which were designed to have regions overlapping to the terminal regions of the CDRs and the FRs. The resultant DNA is ligated to DNA encoding the human antibody C-region, and the ligation product is integrated into an expression vector. The resultant recombinant expression vector is introduced into a host, thereby producing the humanized antibody (EP 239044, WO 96/02576).

The FRs ligated through the CDRs are selected so that the CDRs can form a satisfactory antigen binding site. If necessary, an amino acid(s) in the FRs of the antibody V-region may be replaced so that the CDRs of the reshaped human antibody can form an appropriate antigen binding site (Sato, K. et al., Cancer Res. (1993) 53, 851-856).

The C-region of the chimeric or humanized antibody may be any human antibody C-region; such as Cγ1, Cγ2, Cγ3 or Cγ4 for the H-chain, and Cκ or Cλ for the L-chain. The human antibody C-region may be modified for the purpose of improving the stability of the antibody or ensuring the stable production of the antibody.

The chimeric antibody is composed of V-regions derived from a non-human mammal antibody and C-regions derived from a human antibody. The humanized antibody is composed of CDRs derived from a non-human mammal antibody and FRs and C-regions derived from a human antibody. The humanized antibody is especially useful as an active ingredient for the therapeutic agent of the present invention, because the antigenicity of the antibody against a human body is reduced.

A specific example of the humanized antibody used in the present invention is humanized #23-57-137-1 antibody; in which the CDRs are derived from mouse-derived #23-57-137-1 antibody; and the L-chain is composed of the CDRs ligated through three FRs (FR1, FR2 and FR3) derived from human antibody HSU 03868 (GEN-BANK, Deftos, M. et al., Scand. J. Immunol., 39, 95-103, 1994) and a FR (FR4)

derived from human antibody S25755 (NBRF-PDB); and the H-chain is composed of the CDRs ligated through FRs derived from human antibody S31679 (NBRF-PDB, Cuisinier, A. M. et al., Eur. J. Immunol. 23, 110-118, 1993) in which a portion of the amino acid residues in the FRs is replaced so that the reshaped humanized antibody can exhibit an antigen-binding activity.

The *E. coli* strains containing the plasmids having DNA encoding the H-chain and the L-chain of the humanized #23-57-137-1 antibody, respectively, are designated *Escherichia coli* JM109 (hMBC1HcDNA/pUC19) (for H-chain) and *Escherichia coli* JM109 (hMBC1Lqλ/pUC19) (for L-chain), respectively. These strains have been deposited under the terms of the Budapest Treaty on Aug. 15, 1996 at the National Institute of Bioscience and Human-technology, Agency of Industrial Science and Technology, Japan (1-3,. Higashi 1-chome, Tsukuba-shi, Ibaraki, Japan), under the accession No. FERM BP-5629 for *Escherichia coli* JM109 (hMBC1HcDNA/pUC19), and under the accession No. FERM BP-5630 for *Escherichia coli* JM109 (hMBC1Lqλ/pUC19).

5. Antibody Variants

The antibody used in the present invention may be any fragment thereof or a modified product of the fragment, as long as it can bind to PTHrP and inhibit the activity of the PTHrP. For example, the fragment of the antibody includes Fab, $F(ab')_2$, Fv, or a single chain Fv (scFv) composed of a H-chain Fv fragment or a L-chain Fv fragment linked together through a suitable linker. Specifically, such antibody fragments can be produced by cleaving the antibody with an enzyme (e.g., papain, pepsin) into antibody fragments, or by constructing a gene encoding the antibody fragment and inserting the gene into an expression vector and introducing the resultant recombinant expression vector into a suitable host cell, thereby expressing the antibody fragment (see, for example, Co, M. S., et al., J. Immunol. (1994), 152, 2968-2976; Better, M. & Horwitz, A. H., Methods in Enzymology (1989), 178, 476-496, Academic Press, Inc.; Plueckthun, A. & Skerra, A., Methods in Enzymology (1989) 178, 476-496, Academic Press, Inc.; Lamoyi, E., Methods in Enzymology (1989) 121, 652-663; Rousseaux, J. et al., Methods in Enzymology (1989) 121, 663-669; and Bird, R. E. et al., TIBTECH (1991) 9, 132-137).

A scFv can be produced by ligating the H-chain V-region to the L-chain V-region through a linker, preferably a peptide linker (Huston, J. S. et al., Proc. Natl. Acad. Sci. USA (1988) 85, 5879-5883). The H-chain V-region and the L-chain V-region in the scFv may be derived from any one of the antibodies described herein. The peptide linker which binds the V-regions may be any single chain peptide, for example, of 12-19 amino acid residues.

The DNA encoding the scFv can be prepared by first amplifying the DNA encoding the H-chain V-region and the DNA encoding the L-chain V-region of the antibody separately using a DNA fragment encoding the entire region of the H-chain or a portion thereof that includes the V-region and a DNA fragment encoding the entire region of the L-chain or a portion thereof that includes the V-region as templates and primer pairs that define the terminal ends of the DNA fragments; and then amplifying the DNA encoding the peptide linker using a DNA fragment encoding the peptide linker as a template and a primer pair that define the terminal ends of the DNA fragment so that each terminal end of the peptide linker is ligated to the H-chain V-region and the L-chain V-region, respectively.

Once the DNA encoding the scFv is prepared, an expression vector carrying the DNA and a host transformed with the expression vector can be prepared by conventional methods. The scFv can be produced from the transformed host in any conventional method.

The antibody fragments used in the present invention may be produced by preparing genes for the fragments and expressing the genes in suitable hosts as described above. These antibody fragments are also encompassed in the "antibody" of the present invention.

As a modified form of the above-mentioned antibodies, for example, anti-PTHrP antibody conjugated to any molecule (e.g., polyethylene glycol) may also be used. Such modified antibodies are also encompassed in the "antibody" of the present invention. The modified antibodies can be prepared by chemical modifications of the antibodies. The chemical modification techniques suitable for this purpose have already been established in the art.

6. Expression and Production of Recombinant Antibody or Modified Antibody

The antibody gene constructed as described above can be produced and expressed by known methods. For the expression in a mammalian cell, a conventional useful promoter, the antibody gene to be expressed and a poly(A) signal (located downstream to the 3' end of the antibody gene) are operably linked. For example, as the useful promoter/enhancer system, a human cytomegalovirus immediate early promoter/enhancer system may be used.

Other promoter/enhancer systems, for example, those derived from viruses (e.g., retrovirus, polyoma virus, adenovirus and simian virus 40 (SV40)) and those derived from mammalian cells (e.g., human elongation factor 1α (HEF1α)), may also be used for the expression of the antibody in the present invention.

When SV40 promoter/enhancer system is used, the gene expression may be performed readily by the method of Mulligan et al. (Nature (1979) 277, 108). When HEF1α promoter/enhancer system is used, the gene expression may be performed readily by the method of Mizushima et al. (Nucleic Acids Res. (1990) 18, 5322).

For the expression in *E. coli*, a conventional useful promoter, a signal sequence for secreting the antibody of interest and the antibody gene may be operably linked. As the promoter, lacZ promoter or araB promoter may be used. When lacZ promoter is used, the gene expression may be performed by the method of Ward et al. (Nature (1098) 341, 544-546; FASBE J. (1992) 6, 2422-2427), while when araB promoter is used, the gene expression may be performed by the method of Better et al. (Better et al., Science (1988) 240, 1041-1043).

With respect to the signal sequence for secretion of the antibody, when the antibody of interest is intended to be secreted in a periplasmic space of the *E. coli*, pelB signal sequence (Lei, S. P. et al., J. Bacteriol. (1987) 169, 4379) may be used. The antibody secreted into the periplasmic space is isolated and then refolded so that the antibody takes an appropriate configuration.

The replication origin derived from viruses (e.g., SV40, polyoma virus, adenovirus, bovine papilloma virus (BPV)) or the like may be used. In order to increase the gene copy number in the host cell system, the expression vector may further contain a selective marker gene, such as an aminoglycoside phosphotranferase (APH) gene, a thymidine kinase (TK) gene, an *E. coli* xanthine-guanine phosphoribosyltransferase (Ecogpt) gene and a dihydrofolate reductase (dhfr) gene.

For the production of the antibody used in the present invention, any expression system including eukaryotic and prokaryotic cell systems may be used. The eukaryotic cell includes established cell lines of animals (e.g., mammals, insects, molds and fungi, yeast). The prokaryotic cell includes bacterial cells such as *E. coli* cells.

It is preferable that the antibody used in the present invention be expressed in a mammalian cell, such as a CHO, COS, myeloma, BHK, Vero and HeLa cell.

Next, the transformed host cell is cultured in vitro or in vivo to produce the antibody of interest. The cultivation of the host cell may be performed by any known method. The culture medium usable herein may be DMEM, MEM, RPMI 1640 or IMDM medium. The culture medium may contain a serum supplement, such as fetal calf serum (FCS).

7. Isolation and Purification of Antibody

The antibody expressed and produced as described above may be isolated from the cells or the host animal body and purified to uniformity. The isolation and purification of the antibody used in the present invention may be performed on an affinity column. Examples of a protein A column include Hyper D, POROS and Sepharose F.F. (Pharmacia). Other methods conventionally used for the isolation and purification of an antibody may be also be used; thus the method is not particularly limited. For example, various chromatographs using columns including the above-mentioned affinity column, filtration, ultrafiltration, salting out and dialysis may be used singly or in combination to isolate and purify the antibody of interest (Antibodies A Laboratory Manual. Ed. Harlow, David Lane, Cold Spring Harbor Laboratory, 1988).

8. Determination of the Activities of the Antibody

The determination of the antigen-binding activity (Antibodies A Laboratory Manual, Ed. Harlow, David Lane, Cold Spring Harbor Laboratory, 1988) or the inhibitory activity against a ligand receptor (Harada, A. et al., International Immunology (1993) 5, 681-690) of the antibody used in the present invention may be performed by any known methods.

As the method for the determination of the antigen-binding activity of the anti-PTHrP antibody used in the present invention, for example, ELISA (enzyme-linked immunosorbent assay), EIA (enzyme immunoassay), RIA (radioimmunoassay) or fluorescent antibody technique may be employed. For example, when enzyme immunoassay is employed, a sample solution containing the anti-PTHrP antibody (e.g., a culture supernatant of anti-PTHrP antibody-producing cells, or the anti-PTHrP antibody per se in a purified form) is added to a plate on which PTHrP (1-34) is previously coated. A secondary antibody labeled with an enzyme (e.g., alkaline phosphatease) is further added to the plate. The plate is incubated and washed. A substrate for the enzyme (e.g., p-nitrophenylphosphoric acid) is added to the plate, and the absorbance of the solution in the plate is measured to evaluate the antigen-binding activity of the antibody.

To confirm the activity of the antibody used in the present invention, a neutralizing activity of the antibody (e.g., anti-PTHrP antibody) is determined.

9. Routes for Administration and Pharmaceutical Preparations

The therapeutic agent of the present invention can be used for treatment or amelioration of cachexia. The cachexia to be treated or ameliorated by the present invention may be of any type, including cancer-induced type. Examples of the cancer-induced cachexia include those as described in J. Urol. (UNITED STATES) March 1995, 153 (3 Pt 1) p.854-857; Langenbecks Arch. Chir. Suppl II Verh Dtsch Ges Chir (GERMANY) 1990, p.261-265; Oncology (SWITZERLAND) 1990, 47 (1) p.87-91; Int. J. Pancreatol. (UNITED STATES) Aug-Nov 1990, 7 (1-3) p.141-150; J. Natl. Cancer Inst. (UNITED STATES) Dec. 19, 1990, 82 (24) p.1922-1926.

Examples of cachexia other than the cancer-induced cachexia include those as described in JPEN J. Parenter. Enteral Nutr. (UNITED STATES) Nov-Dec 1990, 14 (6) p.605-609; Chest (UNITED STATED) Nov 1990, 98 (5) p.1091-1094; Bone Marrow Transplant. (ENGLAND) Jul 1990, 6 (1) p.53-57.

The therapeutic agent comprising the anti-PTHrP antibody as an active ingredient of the present invention may be administered orally or parenterally, but preferably parenterally. The therapeutic agent may take any dosage form, such as a transpulmonary agent (e.g., an agent administered with the help of a device such as a nebulizer), a nasogastric agent, a transdermic agent (e.g., ointment, cream) or an injection. Examples of the injection include an intervenous injection (e.g., drops), an intramuscular injection, an intraperitoneal injection and a subcutaneous injection for systemic or topical administration. The route of administration may be properly selected depending on the age of a patient and the conditions of diseases. An effective single dose may be selected from the range of 0.001 to 1,000 mg per kg of body weight. Alternatively, the dose to a patient may be selected from the range of 0.01 to 100,000 mg/body. However, the dose of the therapeutic agent comprising the anti-PTHrP antibody of the present invention is not particularly limited to the above-mentioned ranges.

The therapeutic agent may be administered to a patient at any stage, including before or after the development of cachexia. Alternatively, the therapeutic agent may be administered at the stage where the development of weight loss is predicted in the patient.

The therapeutic agent comprising the anti-PTHrP antibody as an active ingredient of the present invention may be formulated by any conventional method (Remington's Pharmaceutical Science, latest edition, Mark Publishing Company, Easton, USA). The formulation may further comprise pharmaceutically acceptable carriers and additives.

Examples of such carriers and additives include water, pharmaceutically acceptable organic solvents, collagen, polyvinyl alcohol, polyvinyl pyrrolidone, carboxyvinyl polymer, sodium carboxymethyl cellulose, poly(sodium acrylate), sodium arginate, water soluble dextran, sodium carboxymethyl starch, pectin, methyl cellulose, ethyl cellulose, xanthane gum, gum arabic, casein, agar, polyethylene glycol, diglycerin, glycerin, propylene glycol, vaseline, paraffin, stearyl alcohol, stearic acid, human serum albumin (HSA), mannitol, sorbitol, lactose, and surfactants acceptable as pharmaceutical additives.

In the practical use, the additive is properly selected from the above members either singly or in combination depending on the dosage form employed, but not limited thereto. For example, an injection may be used which is prepared by dissolving the anti-PTHrP antibody in a purified form into a solvent (e.g., normal saline, a buffer, a grape sugar solution) and then further adding an adsorption-preventing agent (e.g., Tween 80, Tween 20, a gelatin, human serum albumin) thereto.

The therapeutic agent of the present invention may also be in a re-constitutive, freeze-dried form, which is dissolved before use. For the preparation of the freeze-dried dosage form, an excipient such as a sugar alcohol (e.g., mannitol, grape sugar) and a sugar may be incorporated.

BEST MODE FOR CARRYING OUT THE INVENTION

Hereinbelow, the present invention will be described in greater detail with reference to the following Reference Examples and Examples, which should not be construed as limiting the technical scope of the invention.

EXAMPLE 1

Pharmacological Test Using Cachexia Model Animal

Using a cachexia model animal (a human tumor-implanted nude mouse), a murine monoclonal antibody against PTHrP was examined for its therapeutic effect on cachexia.

As a cachexia model animal, a nude mouse implanted with human oral cavity carcinoma OCC-1 [purchased from the Central Institute for Experimental Animals] was used. It has been known that a nude mouse implanted with human oral cavity carcinoma OCC-1 exhibits an increased blood calcium level as increasing the tumor volume and develops cachexia symptoms such as weight loss and decrease in movements. In this test, amelioration of such human oral cavity carcinoma OCC-1-induced cachexia symptoms by the murine monoclonal antibody was evaluated with respect to blood calcium level, body weight and effect on prolongation of survival time.

The human oral cavity carcinoma OCC-1 was passaged in vivo using BALB/c-nu/nu nude mice (Japan CLEA Co., Inc.). For the evaluation of pharmacological effect, 6-weeks-old male BALB/c-nu/nu nude mice (Japan CLEA Co., Inc.) were purchased and acclimatized for 1 week to give 7-weeks-old mice, which were provided for use in the evaluation.

The cachexia model mice were prepared and divided into groups in the following manner. The passaged human oral cavity carcinoma OCC-1 was removed from the nude mouse, and then finely cut into 3-mm cube of blocks. The resultant tumor blocks were subcutaneously implanted into each of the mice at the lateral region at one piece per mouse. Ten days after the implantation, when it was confirmed that the tumor volume in each of the mice became sufficiently large, the mice were divided into groups so that blood calcium levels, body weights and tumor volumes of the mice in the individual groups were averaged, which were provided for use as the cachexia model animals.

The examination of therapeutic effect-on cachexia was performed as follows.

(1) Observation of Survival Time

Figure 1:
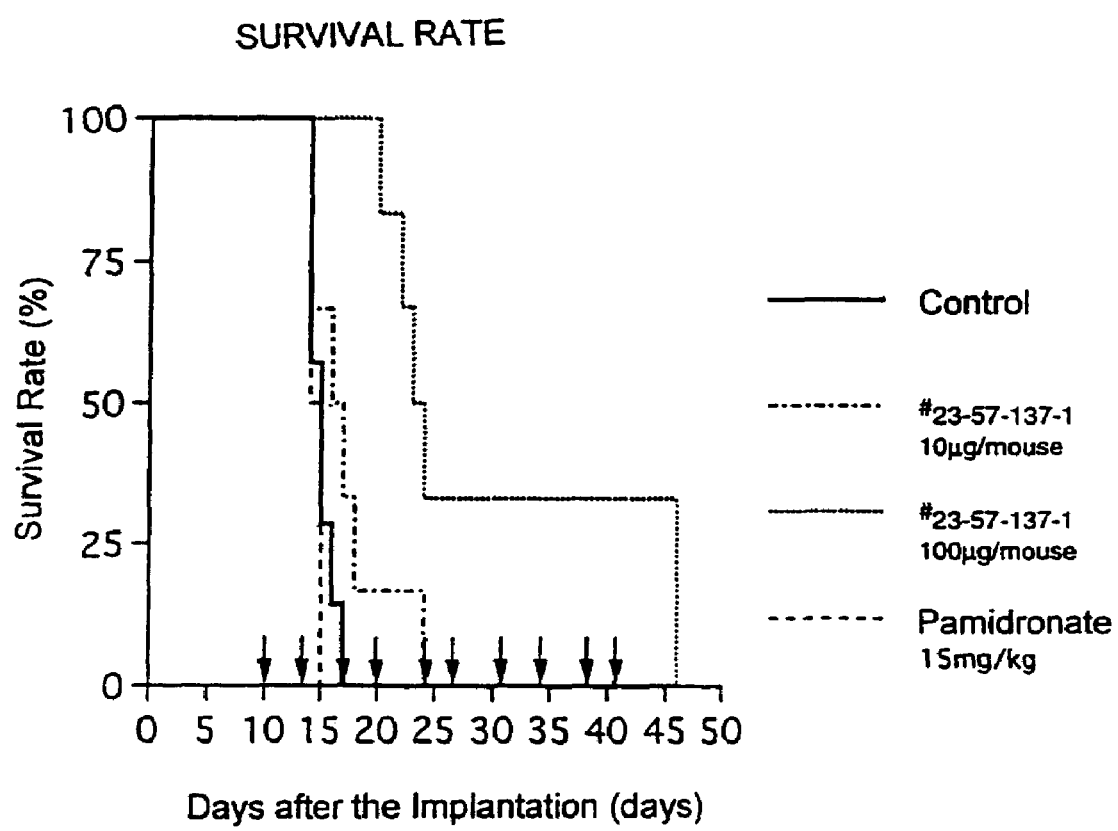
FIG. 1. is a graphical illustration of the therapeutic effect of an anti-PTHrP antibody on cachexia. The graph measures the survival rate as a function of days after implantation of the human oral cavity carcinoma OCC-1. The arrows indicate the days on which the four samples were administered.

In the examination of the effect on prolongation of survival time, a mouse monoclonal antibody was administered to the mice of a test group twice a week, and the survival time of each of the mice was observed. A single dose of an existing hypercalcemia-treating agent, pamidronate (pamidronate disodium; Aredia), was administered to the mice of another test group via tail vein at a dose amount of 15 mg/kg. As a control in this test, phosphate-buffered saline (PBS) was administered to the mice of a control group via tail vein twice a week at a dose amount of 0.2 ml/mouse. The results are shown in FIG. 1.

(2) Observation of Blood Calcium Level

The mouse monoclonal antibody against PTHrP was administered to the cachexia model mice of a test group twice at intervals of two days via tail vein at a dose amount of either 10 μg or 100 μg per mouse for each administration. A single dose of an existing hypercalcemia-treating agent, pamidronate (pamidronate disodium; Aredia), was administered to the mice of another test group via tail vein at a dose amount of 15 mg/kg. As a control in this test, phosphate-buffered saline (PBS) was administered to the mice of a control group via tail vein twice at intervals of two days at a dose amount of 0.2 ml/mouse for each administration.

(3) Determination of Blood Calcium Level

Figure 2:
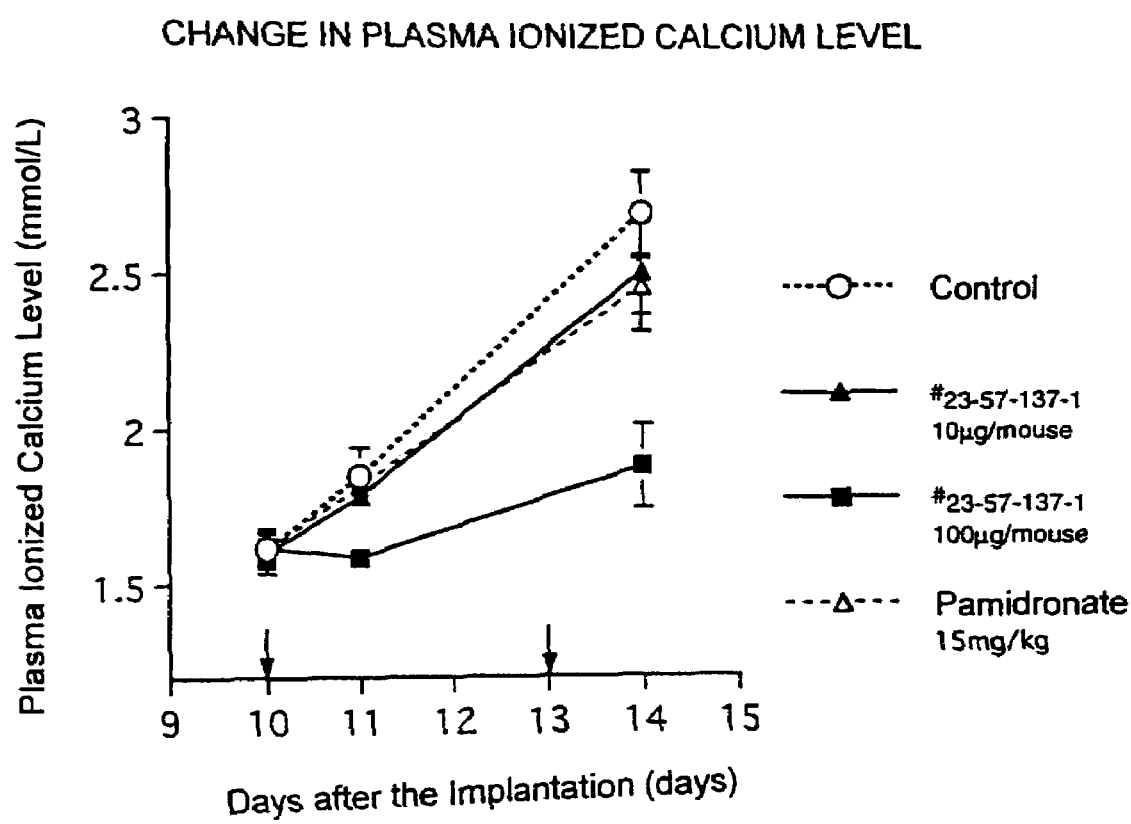
FIG. 2. is a graphical illustration of the therapeutic effect of an anti-PTHrP antibody on cachexia. The graph measures the plasma ionized calcium level as a function of days after implantation of the human oral cavity carcinoma OCC-1. The arrows indicate the days on which the four samples were administered.
Figure 3:
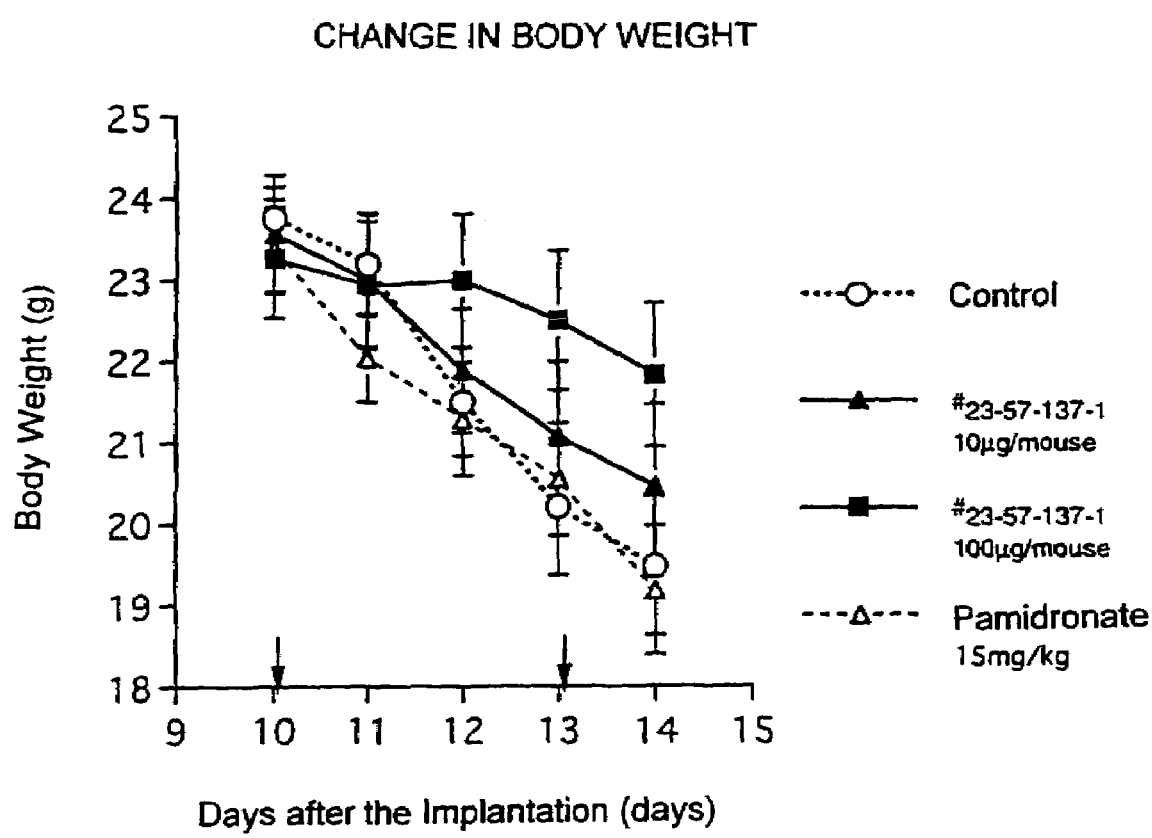
FIG. 3. is a graphical illustration of the therapeutic effect of an anti-PTHrP antibody on cachexia. The graph measures body weight as a function of days after implantation of the human oral cavity carcinoma OCC-1. The arrows indicate the days on which the four samples were administered.

One and four days after the administration of the mouse monoclonal antibody, the blood calcium level of each of the mice was determined to evaluate the pharmacological efficacy of the antibody. The blood calcium level was determined as whole blood ionized calcium level, by drawing blood from each of the mice via the orbit using a hematocrit tube and applying the blood to 643 Automatic Ca/pH Analyzer (CIBA-CORNING). The body weight of each mouse was weighed everyday till four days after the administration of the antibody. The results are shown in FIGS. 2 and 3.

(4) Determination of Tumor Volume

Figure 4:
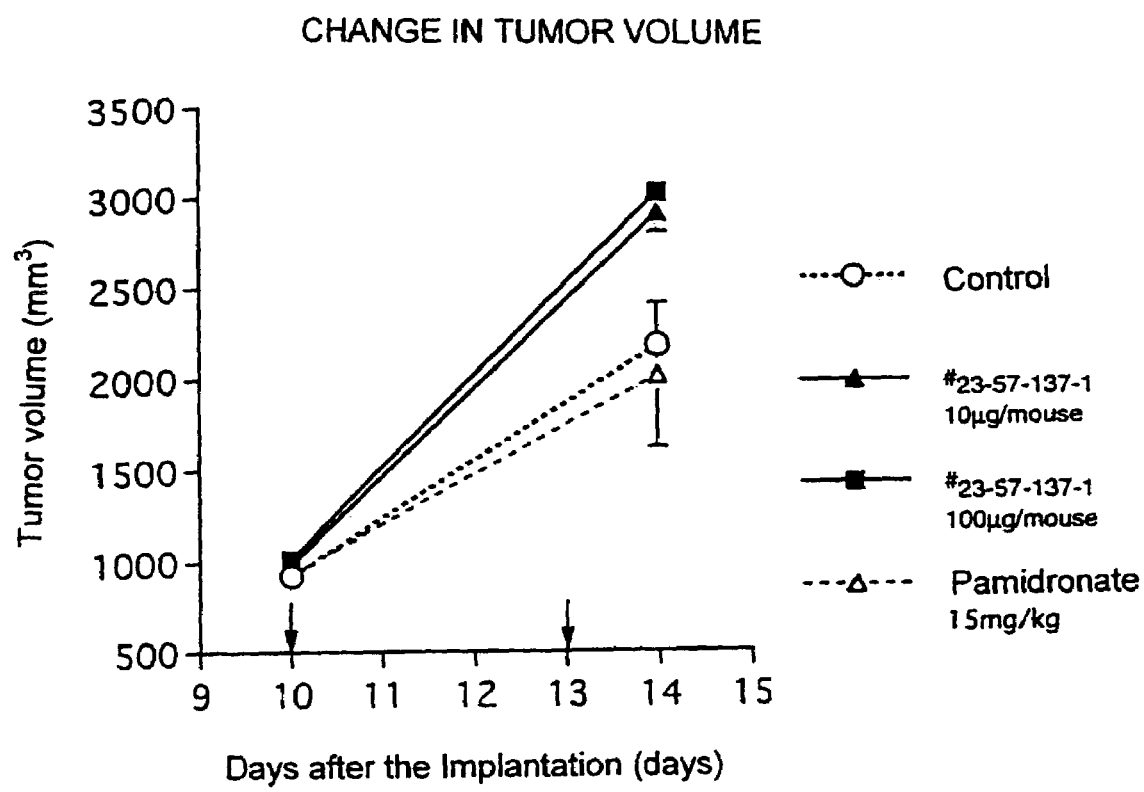
FIG. 4. is a graphical illustration of the therapeutic effect of an anti-PTHrP antibody on cachexia. The graph measures tumor volume as a function of days after implantation of the human oral cavity carcinoma OCC-1. The arrows indicate the days on which the four samples were administered.

The tumor volume was determined four days after the administration of the antibody, by measuring the longest axis (a mm) and the shortest axis (b mm) of the tumor and applying the both measured values to Galant's equation $[ab^2/2]$. The results are shown in FIG. 4.

As apparent from these results, although the mice administered with the antibody at a dose amount of 10 μg showed blood calcium levels equivalent to those of the mice administered with pamidronate, weight loss in antibody-administered mice was observed to be inhibited, as weight loss was not as pronounced as that in pamidronate-administered mice. The mice administered with the antibody at a dose amount of 100 μg prevented the increase in blood calcium level and inhibited weight loss to a higher degree, when compared to pamidronate-administered mice and the control mice. In the mice administered with the anti-PTHrP neutralizing antibody at a dose amount of 100 μg twice a week, a significant degree of prolongation in survival time was observed compared with the pamidronate-administered mice and the control mice (p=0.0003: Log Rank test). As a result, it is found that the neutralizing mouse monoclonal antibody against PTHrP has excellent effects that any existing hypercalcemia-treating agents cannot exhibit, such as prevention of weight loss and prolongation of survival time. These results demonstrate that the antibody used in this test is useful as a therapeutic agent for malignancy-associated cachexia.

EXAMPLE 2

Pharmacological Test Using Hypercalcemia and Cachexia Model Animals

Using a cachexia model animal (a human tumor-implanted nude mouse), a humanized antibody version "q" against PTHrP was examined for its therapeutic effect on cachexia.

As a model animal, a nude mouse implanted with human oral cavity carcinoma OCC-1 [purchased from the Central Institute for Experimental Animals] was used. It has been known that a nude mouse implanted with human oral cavity carcinoma OCC-1 exhibits an increased blood calcium level as increasing the tumor volume and develops cachexia symptoms such as weight loss and decrease in movements. In this test, improvement of such human oral cavity carcinoma OCC-1-induced cachexia symptoms by the humanized antibody version "q" was evaluated with respect to blood calcium level, body weight and effect on prolongation of survival time.

The subculture of the human oral cavity carcinoma OCC-1 was performed in vivo using BALB/c-nu/nu nude mice (Japan CLEA Co., Inc.). For the evaluation of pharmacological effect, 6-weeks-old male BALB/c-nu/nu nude mice (Japan CLEA Co., Inc.) were purchased and acclimatized for 1 week to give 7-weeks-old mice, which were provided for use in the evaluation.

The cachexia model mice were prepared and divided into groups in the following manner. The passaged human oral cavity carcinoma OCC-1 was removed from the nude mouse, and then finely cut into 3-mm cube of blocks. The resultant tumor blocks were subcutaneously implanted into each of the mice at the lateral region at one piece per mouse. Ten days after the implantation, when it was confirmed that the tumor volume in each of the mice became sufficiently large, the mice were divided into groups so that blood calcium levels, body weights and tumor volumes of the mice in the individual groups were averaged, which were provided for use as the cachexia model animals.

The examination of therapeutic effect on cachexia was performed as follows.

(1) Observation of Survival Time

Figure 16:
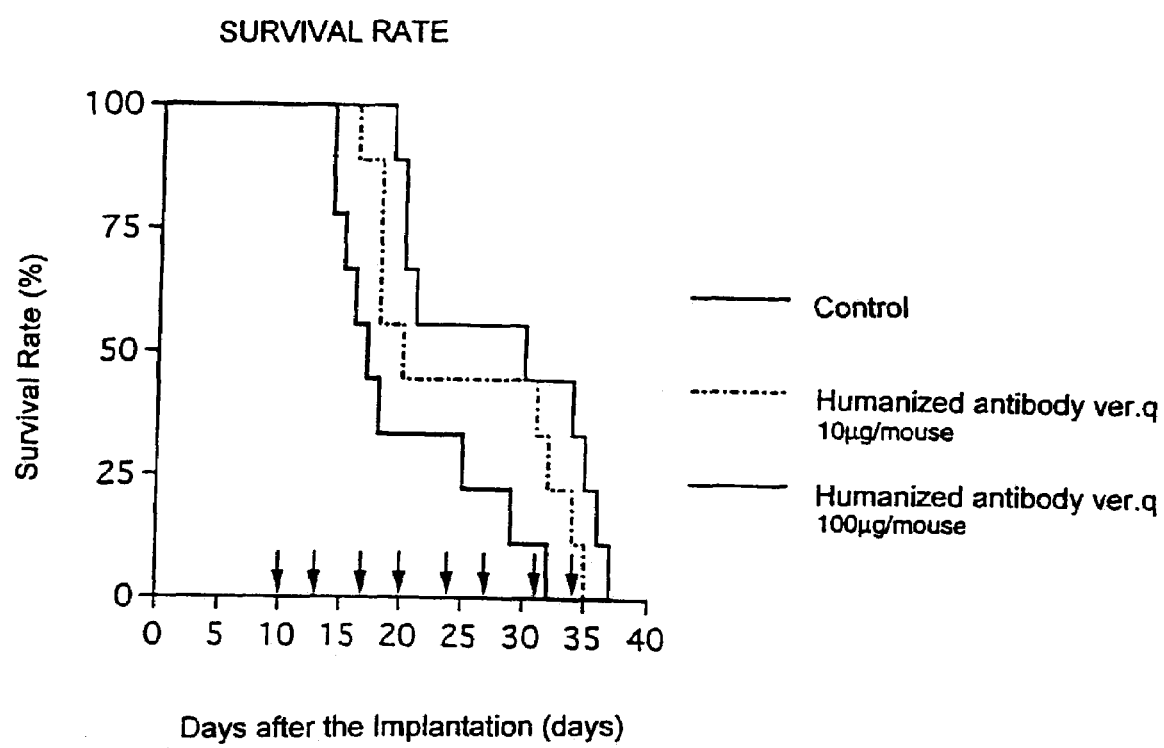
FIG. 16. is a graphical illustration of the therapeutic effect of a humanized antibody on cachexia. The graph measures the survival rate as a function of days after implantation of the human oral cavity carcinoma OCC-1.

In the examination of the effect on prolongation of survival time, a humanized antibody version "q" was administered to the mice of a test group twice a week, and the survival time of each of the mice was observed. As a control of this test, phosphate-buffered saline (PBS) was administered to the mice of a control group via tail vein twice a week at a dose amount of 0.1 ml/mouse. The results are shown in FIG. 16.

(2) Observation of Blood Calcium Level

The humanized antibody version "q" was administered to the cachexia model mice of a test group twice at intervals of two days via tail vein at a dose amount of either 10 µg or 100 µg per mouse for each administration. As a control in this test, phosphate-buffered saline (PBS) was administered to the mice of a control group via tail vein twice at intervals of two days at a dose amount of 0.1 ml/mouse for each administration.

(3) Determination of Blood Calcium Level

Figure 17:
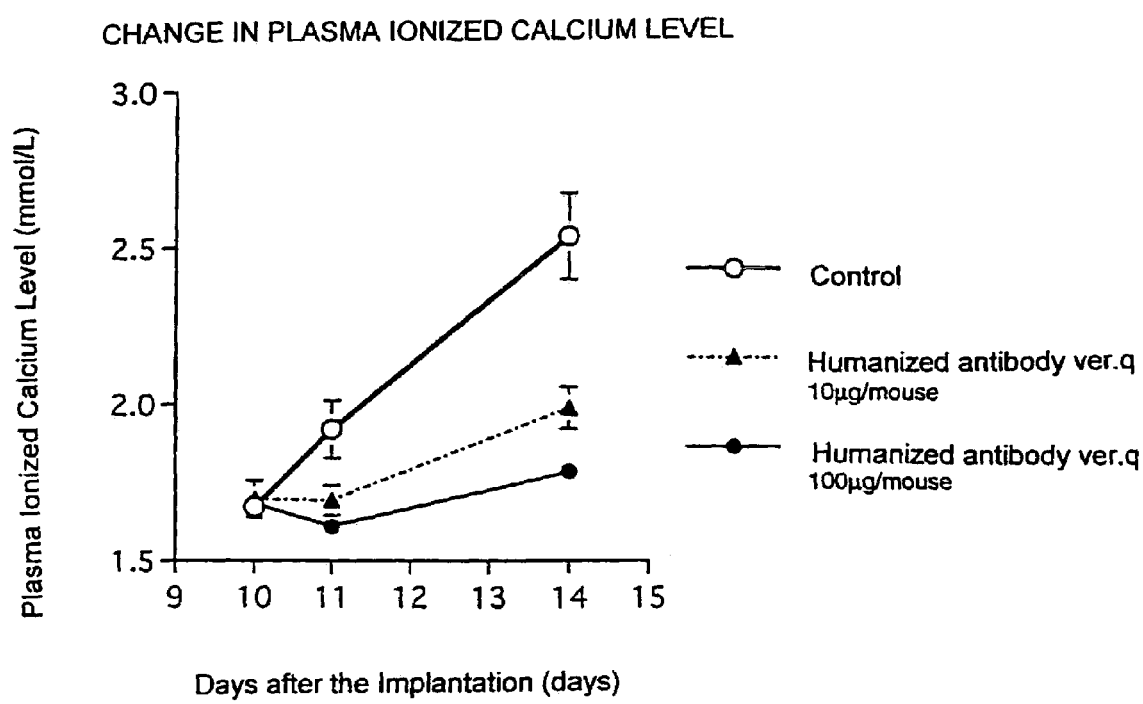
FIG. 17. is a graphical illustration of the therapeutic effect of a humanized antibody on cachexia. The graph measures the plasma ionized calcium level as a function of days after implantation of the human oral cavity carcinoma OCC-1.
Figure 18:
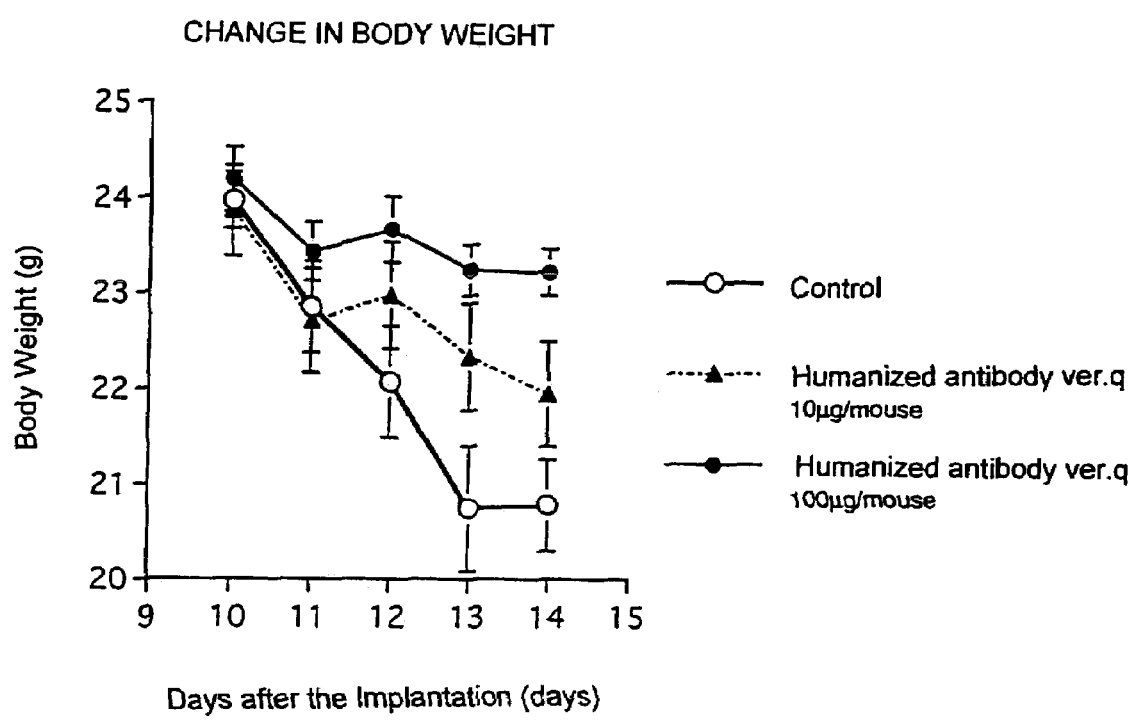
FIG. 18 is a graphical illustration of the therapeutic effect of a humanized antibody on cachexia. The graph measures the body weight as a function of days after implantation of the human oral cavity carcinoma OCC-1.

One and four days after the first administration of the humanized antibody version "q", the blood calcium level of each of the mice was determined to evaluate the pharmacological efficacy of the antibody. The blood calcium level was determined as whole blood ionized calcium level, by drawing blood from each of the mice via the orbit using a hematocrit tube and applying the blood to 643 Automatic Ca/pH Analyzer (CIBA-CORNING). The body weight of each mouse was weighed everyday till four days after the administration of the antibody. The results are shown in FIGS. 17 and 18.

(4) Determination of Tumor Volume

Figure 19:
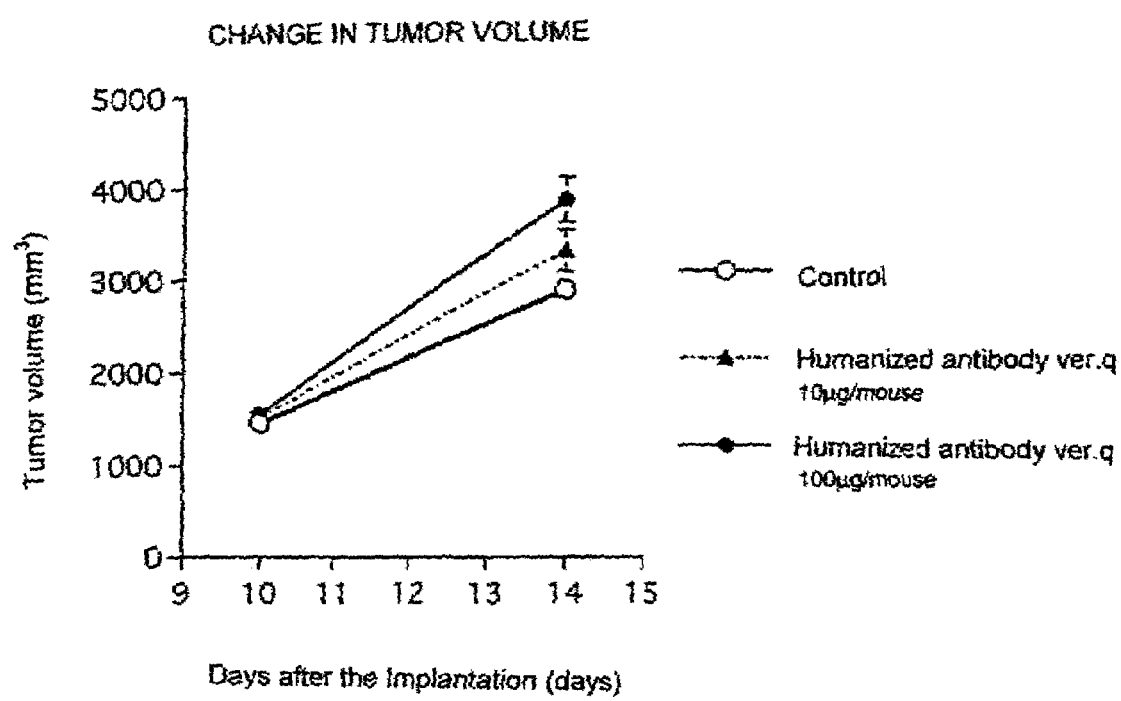
FIG. 19. is a graphical illustration of the therapeutic effect of a humanized antibody on cachexia. The graph measures the tumor volume as a function of days after implantation of the human oral cavity carcinoma OCC-1.

The tumor volume was determined four days after the first administration of the antibody, by measuring the longest axis (a mm) and the shortest axis (b mm) of the tumor and applying the both measured values to Galant's equation [$ab^2/2$]. The results are shown in FIG. 19.

As apparent from these results, the mice administered with the humanized antibody version "q" at a dose amount of either 10 µg or 100 µg prevented the increase in blood calcium level and weight loss in antibody-administered mice was observed to be inhibited, as weight loss was not as pronounced as that in control mice. In the mice administered with the humanized antibody version "q" at a dose amount of 100 µg twice a week, a significant degree of prolongation of survival time was observed compared with the control mice (p=0.0108: Log Rank test). The efficacy of the humanized antibody version "q" on the model animals with malignancy-associated cachexia was similar to that of the above-tested mouse monoclonal antibody. These results demonstrate the antibody used in this test is useful as a therapeutic agent for malignancy-associated cachexia.

REFERENCE EXAMPLE 1

Preparation of Hybridomas Producing anti-PTHrP (1-34) Mouse Monoclonal Antibody

Hybridomas capable of producing a monoclonal antibody against human PTHrP (1-34) (SEQ ID NO: 75), #23-57-154 and #23-57-137-1, were prepared in accordance with the method reported by Kanji Sato et al. (Sato, K. et al., J. Bone Miner. Res. 8, 849-860, 1993).

The immunogen used was PTHrP (1-34) (Peninsula), to which a carrier protein thyroglobulin was conjugated with carbodiimide (Dojinn). The thycloglobulin-conjugated PTHrP (1-34) was dialyzed to obtain a solution having a protein concentration of 2 µg/ml. The resultant solution was mixed with Freund's adjuvant (Difco) at a mixing ratio of 1:1 to give an emulsion. This emulsion was injected to 16 female BALB/C mice 11 times dorsal-subcutaneously or intraperitoneally at a dose amount of 100 µg/mouse for each injection, thereby immunizing the mice. For the priming immunization, Freund's complete adjuvant was used; while for the boosting immunization, Freund's incomplete adjuvant was used.

Each of the immunized mice was determined for its antibody titer in the serum in the following manner. That is, each of the mice was blood-drawn via its tail vein, and the anti-serum is separated from the blood. The anti-serum was diluted with a RIA buffer and mixed with $^{125}$I-labeled PTHrP (1-34) to determine the binding activity. The mice that were confirmed to have a sufficiently increased titer were injected with PTHrP (1-34) without a carrier protein intraperitoneally at a dose amount of 50 µg/mouse for the final immunization.

Three days after the final immunization, the mouse is sacrificed and the spleen was removed therefrom. The spleen cells were subjected to cell fusion with mouse myeloma cell line P3x63Ag8U.1 in accordance with any conventional known method using 50% polyethylene glycol 4000. The fused cells thus prepared were seeded to each well of 85 of 96-well plates at $2 \times 10^4$/well. Hybridomas were screened in HAT medium as follows.

The screening of hybridomas was performed by determining the presence of PTHrP-recognition antibodies in the culture supernatant of the wells in which cell growth had been observed in HAT medium, by a solid phase RIA method. The hybridomas were collected from the wells in which the binding ability to the PTHrP-recognition antibodies had been confirmed. The hybridomas thus obtained was suspended into RPMI-1640 medium containing 15% FCS supplemented with OPI-supplement (Sigma), followed by unification of the hybridomas by a limiting dilution method. Thus, two types of hybridoma clones, #23-57-154 and #23-57-137-1, could be obtained, both which had a strong binding ability to PTHrP (1-34).

Hybridoma clone #23-57-137-1 was designated "mouse-mouse hybridoma #23-57-137-1", and has been deposited under the terms of the Budapest Treaty on Aug. 15, 1996 at the National Institute of Bioscience and Human-technology, Agency of Industrial Science and Technology, Japan (1-3, Higashi 1-chome, Tsukuba-shi, Ibaraki, Japan) under the accession No. FERM BP-5631.

REFERENCE EXAMPLE 2

Cloning of DNA Encoding V-Region of Mouse Monoclonal Antibody Against Human PTHrP (1-34)

Cloning of DNA encoding the V-region of a mouse monoclonal antibody against human PTHrP (1-34) #23-57-137-1 was performed in the following manner.

(1) Preparation of mRNA mRNA from hybridoma #23-57-137-1 was prepared using Quick Prep mRNA Purification Kit (Pharmacia Biotech). That is, cells of hybridoma #23-57-137-1 were fully homogenized with an extraction buffer, and mRNA was isolated and purified therefrom on an oligo(dT)-Cellulose Spun Column in accordance with the instructions included in the column.

The resultant solution was subjected to ethanol precipitation to obtain the mRNA as a precipitate. The mRNA precipitate was dissolved in an elution buffer.

(2) Production and Amplification of cDNA for Gene Encoding Mouse H-Chain V-Region (i) Cloning of cDNA for #23-57-137-1 Antibody H-chain V-Region A gene encoding H-chain V-region of the mouse monoclonal antibody against human PTHrP was cloned by a 5'-RACE method (Frohman, M. A. et al., Proc. Natl. Acad. Sci. USA, 85, 8998-9002, 1988; Belyavsky, A. et al., Nucleic Acids Res. 17, 2919-2932, 1989). The 5'-RACE method was performed using 5'-Ampli FINDER RACE Kit (CLONETECH) in accordance with the instructions included in the kit. In this method, the primer used for synthesis of cDNA was MHC2 primer (SEQ ID NO: 1) which is capable of hybridizing to mouse H-chain C-region. The above-prepared mRNA (about 2 µg), which was a template for the cDNA synthesis, was mixed with MHC2 primer (10 pmoles). The resultant mixture was reacted with a reverse transcriptase at 52° C. for 30 minuets to effect the reverse transcription of the mRNA into cDNA.

The resultant reaction solution was added with 6N NaOH to hydrolyze any RNA remaining therein (at 65° C. for 30 min.) and then subjected to ethanol precipitation to isolate and purify the cDNA as a precipitate. The purified cDNA was ligated to Ampli FINDER Anchor (SEQ ID NO: 42) at the 5' end by reacting with T4 RNA ligase at 37° C. for 6 hours and additionally at room temperature for 16 hours. As the primers for amplification of the cDNA by a PCR method, Anchor primer (SEQ ID NO: 2) and MHC-G1 primer (SEQ ID NO: 3) (S. T. Jones, et al., Biotechnology, 9, 88, 1991) were used.

The PCR solution comprised (per 50 µl) 10 mM Tris-HCl (pH 8.3), 50 mM KCl, 0.25 mM dNTPs (dATP, dGTP, dCTP, dTTP), 1.5 mM $MgCl_2$, 2.5 units of TaKaRa Taq (Takara Shuzo Co., Ltd.), 10 pmoles Anchor primer, and 1 µl of the reaction mixture of the cDNA to which MHC-G1 primer and Ampli FINDER Anchor primer had been ligated, over which mineral oil (50 µl) was layered. The PCR was performed in Thermal Cycler Model 480J (Perkin Elmer) for 30 cycles under the conditions: 94° C. for 45 sec.; 60° C. for 45 sec.; and 72° C. for 2 min.

(ii) Cloning of cDNA for #23-57-137-1 Antibody L-Chain V-Region

A gene encoding L-chain V-region of the mouse monoclonal antibody against human PTHrP was cloned by the 5'-RACE method (Frohman, M. A. et al., Proc. Natl. Acad. Sci. USA, 85, 8998-9002, 1988; Belyavsky, A. et al., Nucleic Acids Res. 17, 2919-2932, 1989). The 5'-RACE method was performed using 5'-Ampli Finder RACE Kit (Clonetech) in accordance with the instructions included in the kit. In this method, oligo-dT primer was used as the primer for synthesizing cDNA. The above-prepared mRNA (about 2 µg), which was a template for the cDNA synthesis, was mixed with oligo-dT primer. The resultant mixture was reacted with a reverse transcriptase at 52° C. for 30 min. to effect the reverse transcription of the mRNA into cDNA. The resultant reaction solution was added with 6N NaOH to hydrolyze any RNA remaining therein (at 65° C. for 30 min.). The resultant solution was subjected to ethanol precipitation to isolate and purified the cDNA as a precipitate. The cDNA thus synthesized was ligated to Ampli FINDER Anchor at the 5' end by reacting with T4 RNA ligase at 37° C. for 6 hours and additionally at room temperature for 16 hours.

A PCR primer MLC (SEQ ID NO: 4) was designed based on the conserved sequence of mouse L-chain λ chain C-region and then synthesized using 394 DNA/RNA Synthesizer (ABI). The PCR solution comprised (per 100 µl) 10 mM Tris-HCl (pH 8.3), 50 mM KCl, 0.25 mM dNTPs (dATP, dGTP, dCTP, dTTP), 1.5 mM $MgCl_2$, 2.5 units of AmpliTaq (PERKIN ELMER), 50 pmoles of Anchor primer (SEQ ID NO: 2), and 1 µl of the reaction mixture of the cDNA to which MLC (SEQ ID NO: 4) and Ampli FINDER Anchor were ligated, over which mineral oil (50 µl) was layered. The PCR reaction was performed in Thermal Cycler Model 480J (Perkin Elmer) for 35 cycles under the conditions: 94° C. for 45 sec.; 60° C. for 45 sec.; and 72° C. for 2 min.

(3) Purification and Fragmentation of PCR Products

Each of the DNA fragments amplified by the PCR methods described above was separated by agarose gel electrophoresis on a 3% Nu Sieve GTG agarose (FMC Bio. Products). For each of the H-chain V-region and the L-chain V-region, an agarose gel segment containing a DNA fragment of about 550 bp was excised from the gel. Each of the gel segments was subjected to purification of the DNA fragment of interest using GENECLEAN II Kit (BIO101) in accordance with the instructions included in the kit. The purified DNA was precipitated with ethanol, and the DNA precipitate was dissolved in 20 µl of a solution containing 10 mM Tris-HCl (pH 7.4) and 1 mM EDTA. A portion (1 µl) of the DNA solution was digested with a restriction enzyme XmaI (New England Biolabs) at 37° C. for 1 hour and further digested with a restriction enzyme EcoRI (Takara Shuzo Co., Ltd.) at 37° C. for 1 hour. The digestion solution was extracted with phenol and chloroform and then precipitated with ethanol to collect the DNA.

In this manner, two DNA fragments containing a gene encoding mouse H-chain V-region and a gene encoding mouse L-chain V-region, respectively, were obtained, both which had an EcoRI recognition sequence on the 5' end and an XmaI recognition sequence on the 3' end.

The EcoRI-XmaI DNA fragments containing a gene encoding mouse H-chain V-region and a gene encoding mouse L-chain V-region, respectively, were separately ligeted to pUC19 vector that had been digested with EcoRI and XmaI at 16° C. for 1 hour using DNA Ligation Kit ver. 2 (Takara Shuzo Co., Ltd.) in accordance with the instructions included in the kit. A portion (10 µl) of the ligation mixture was added to 100 µl of a solution containing competent cells of E. coli, JM 109 (Nippon Gene Co., Ltd.). The cell mixture was allowed to stand on ice for 15 min., at 42° C. for-1 min. and additionally for 1 min. on ice. The resultant cell mixture was added with 300 µl of SOC medium (Molecular Cloning: A Laboratory Manual, Sambrook, et al., Cold Spring Harbor Laboratory Press, 1989) and then incubated at 37° C. for 30 min. The resultant cell solution was plated on LB agar medium or 2xYT agar medium (Molecular Cloning: A Laboratory Manual, Sambrook, et al., Cold Spring Harbor Laboratory Press, 1989) containing either 100 or 50 µg/ml of ampicillin, 0.1 mM of IPTG and 20 µg/ml of X-gal, and then incubated at 37° C. overnight. In this manner, E. coli transformants were prepared.

The transformants were cultured at 37° C. overnight in 2 ml of LB or 2xYT medium containing either 100 or 50 µg/ml of ampicillin. The cell fraction was applied to Plasmid Extracter PI-100Σ (Kurabo Industries, Ltd.) or QIAprep Spin Plasmid Kit (QIAGEN) to give plasmid DNA. The plasmid DNA thus obtained was sequenced.

(4) Sequencing of Gene Encoding Mouse Antibody V-Region

The nucleotide sequence of the cDNA coding region carried on the plasmid was determined in DNA Sequencer 373A (ABI; Perkin-Elmer) using Dye Terminator Cycle Sequencing Kit (Perkin-Elmer). In this sequencing, M13 Primer M4 (Takara Shuzo Co., Ltd.) (SEQ ID NO: 5) and M13 Primer RV (Takara Shuzo Co., Ltd.) (SEQ ID NO: 6) were used, and the nucleotide sequence was confirmed in the both directions.

The plasmid containing a gene encoding mouse H-chain V-region derived from hybridoma #23-57-137-1 was designated "MBC1H04", and plasmid containing a gene encoding mouse L-chain V-region derived from hybridoma #23-57-137-1 was designated "MBC1L24". The nucleotide sequences (including the corresponding amino acids sequences) of the DNA encoding the mouse #23-57-137-1 antibody-derived H-chain V-region in plasmid MBC1H04 and gene encoding the mouse #23-57-137-1 antibody-derived L-chain V-region in plasmid MBC1H24 were shown in SEQ. ID Nos: 57 and 65, respectively. Both of the polypeptides for the H-chain V-region fragment and for the L-chain V-region fragment were starting from the 58th nucleotide (which encoding glutamine) in the DNA sequences shown in SEQ ID Nos: 57 and 65, respectively. The amino acid sequences of the polypeptides for the H-chain V-region and the L-chain V-region were also shown in SEQ. ID NOs: 46 and 45, respectively.

The E. coli strain containing plasmid MBC1H04 and the E. coli strain containing plasmid MBC1L24 were designated "Escherichia coli JM109 (MBC1H04)" and "Escherichia coli JM109 (MBC1L24)", respectively. These E. coli strains have been deposited under the terms of the Budapest Treaty at the National Institute of Bioscience and Human-Technology, Agency of Industrial Science and Technology, Japan (1-3, Higashi 1-chome, Tsukuba-shi, Ibaraki, Japan) on Aug. 15, 1996, under the Accession No. FERM BP-5628 for Escherichia coli JM109 (MBC1H04) and FERM BP-5627 for Escherichia coli JM109 (MBC1L24), respectively.

(5) Determination of CDRs of Mouse Monoclonal Antibody #23-57-137-1 Against Human PTHrP The H-chain V-region and the L-chain V-region have general structures similar to each other, in which there are four framework regions (FRs) linked through three hypervariable regions (i.e., complementarity determining regions; CDRs). The amino acid sequences of the FRs are relatively well conserved, while the amino acid sequence of the CDRs have an extremely high variability (Kabat, E. A. et al., "Sequence of Proteins of Immunological Interest", US Dept. Health and Human Services, 1983). In view of these facts, the homology in amino acid between the V-regions of the mouse monoclonal antibody against human PTHrP was determined with reference to the database of amino acid sequences for antibodies established by Kabat et al. Thus, the CDRs of the V-regions were determined as shown in Table 1.

The amino acid sequences for CDRs 1-3 in the L-chain V-region shown in SEQ ID Nos: 59 to 61, respectively; and the amino acid sequences for CDRs 1-3 in the H-chain V-region are shown in SEQ ID Nos: 62 to 64, respectively.

TABLE 1

| V-region | SEQ ID NO. | CDR1 | CDR2 | CDR3 |
|---|---|---|---|---|
| H-chain V-region | 57 | 31–35 | 50–66 | 99–107 |
| L-chain V-region | 65 | 23–34 | 50–60 | 93–105 |

REFERENCE EXAMPLE 3

Construction of Chimeric Antibody (1) Construction of Chimeric Antibody H-Chain
(i) Construction of H-Chain V-Region To ligate to an expression vector carrying a genomic DNA of human H-chain C-region Cγ1, the cloned DNA encoding mouse H-chain V-region was modified by a PCR method. A backward primer MBC1-S1 (SEQ ID NO: 7) was designed to hybridize to a DNA sequence encoding the 5' region of the leader sequence for the V-region and to have both a Kozak consensus sequence (Kozak, M. et al., J. Mol. Biol., 196, 947-950, 1987) and a HindIII-recognition sequence. A forward primer MBC1-a (SEQ ID NO: 8) was designed to hybridize to a DNA sequence encoding the 3' region of the J region and to have both a donor splice sequence and a BamHI-recognition sequence. The PCR reaction was performed using TaKaRa Ex Taq (Takara Shuzo Co., Ltd.) and a buffer appended thereto. The PCR solution comprised (per 50 μl) 0.07 μg of plasmid MBC1H04 as a template DNA, 50 pmoles of MBC1-a and 50 pmoles of MBC1-S1 as primers, 2.5U of TaKaRa Ex Taq and 0.25 mM dNTPs in the buffer, over which 50 μl of mineral oil was layered. The PCR was run for 30 cycles under the conditions: 94° C. for 1 min.; 55° C. for 1 min.; 72° C. for 2 min. The DNA fragments thus amplified by the PCR method were separated by agarose gel electrophoresis on a 3% Nu Sieve GTG Agarose (FMC Bio. Products).

Then, an agarose gel segment containing a DNA fragment of 437 bp was excised, and the DNA fragment was purified therefrom using GENECLEAN II Kit (BIO101) in accordance with the instructions included in the kit. The purified DNA was collected by ethanol precipitation, and then dissolved in 20 μl of a solution containing 10 mM Tris-HCl (pH 7.4) and 1 mM EDTA. A portion (1 μl) of the resultant DNA solution was digested with restriction enzymes BamHI and HindIII (Takara Shuzo Co., Ltd.) at 37° C. for 1 hour. The digestion solution was extracted with phenol and chloroform and then precipitated with ethanol to collect the DNA of interest.

The obtained HindIII-BamHI DNA fragment, which containing a gene encoding the mouse H-chain V-region, was subcloned into pUC19 vector that had been digested with HindIII and BamHI. The resultant plasmid was sequenced in DNA Sequencer 373A (Perkin-Elmer) using M13 Primer M4 and M13 Primer RV as primers and Dye Terminator Cycle Sequencing Kit (Perkin-Elmer). As a result, a plasmid which carried a gene of correct nucleotide sequence encoding the mouse H-chain V-region derived from hybridoma #23-57-137-1 and had a HindIII-recognition sequence and a Kozak sequence on its 5' region and a BamHI-recognition sequence on its 3' region was obtained, which was designated "MBC1H/pUC19".

(ii) Construction of H-Chain V-Region for cDNA-Type of Mouse-Human Chimeric H-Chain To ligate to cDNA of the human H-chain C-region Cγ1, the DNA encoding the mouse H-chain V-region constructed as described above was modified by a PCR method. A backward primer MBC1HVS2 (SEQ ID NO: 9) for the H-chain V-region was designed to cause the replacement of the second amino acid (asparagine) of the sequence encoding the front portion of the leader sequence for the H-chain V-region by glycine and to have a Kozak consensus sequence (Kozak, M. et al., J. Mol. Biol., 196, 947-950, 1987) and HindIII- and EcoRI-recognition sequences. A forward primer MBC1HVR2 (SEQ ID NO: 10) for the H-chain V-region was designed to hybridize to the DNA sequence encoding the 3' region of the J region, to encoding the 5' region of the C-region and to have ApaI- and SmaI-recognition sequences.

The PCR reaction was performed using TaKaRa Ex Taq (Takara Shuzo Co., Ltd.) and a buffer appended thereto. The PCR solution comprised (per 50 μl) 0.6 μg of plasmid MBC1H/pUC19 as a template DNA, 50 pmoles of MBC1HVS2 and 50 pmoles of MBC1HVR2 as primers, 2.5U of TaKaRa Ex Taq and 0.25 mM of dNTPs in the buffer, over which 50 μl of mineral oil was layered. The PCR reaction was run for 30 cycles under the conditions: 94° C. for 1 min.; 55° C. for 1 min.; 72° C. for 1 min. The DNA fragments amplified by the PCR reaction were separated by agarose gel electrophoresis on a 1% Sea Kem GTG Agarose (FMC Bio. Products). Then, an agarose gel segment containing a DNA fragment of 456 bp was excised and the DNA fragment was purified therefrom using GENECLEAN II Kit (BIO101) in accordance with the instructions included in the kit. The purified DNA was precipitated with ethanol and then dissolved in 20 μl of a solution containing 10 mM Tris-HCl (pH 7.4) and 1 mM EDTA.

The resultant DNA solution (1 μg) was digested with restriction enzymes EcoRI and SmaI (Takara Shuzo Co., Ltd.) at 37° C. for 1 hour. The digestion solution was extracted with phenol and chloroform and then precipitated with ethanol to collect the DNA. The obtained EcoRI-SmaI DNA fragment, which containing a gene encoding the mouse H-chain V-region, was subcloned into pUC19 vector that had been digested with EcoRI and SmaI. The resultant plasmid was sequenced in DNA Sequencer 373A (Perkin-Elmer) using M13 Primer M4 and M13 Primer RV, and Dye Terminator Cycle Sequencing Kit (Perkin-Elmer). As a result, a plasmid which contained a gene encoding mouse H-chain V-region derived from hybridoma #23-57-137-1 of correct nucleotide sequence and had EcoRI- and HindIII-recognition sequences and a Kozak sequence on its 5' region and ApaI- and SmaI-recognition sequences on its 3' region was obtained, which was designated "MBC1Hv/pUC19".

(iii) Construction of Expression Vector for Chimeric Antibody H-Chain cDNA containing the DNA for human antibody H-chain C-region Cγ1 was prepared as follows. mRNA was prepared from a CHO cell into which both an expression vector DHFR-ΔE-RVh-PM-1-f (see WO 92/19759) encoding the genomic DNAs of humanized PM1 antibody H-chain V-region and human antibody H-chain C-region IgG1 (N. Takahashi et al., Cell 29, 671-679, 1982) and an expression vector RV1-PM1a (see WO 92/19759) encoding the genomic DNAs of humanized PM1 antibody L-chain V-region and human antibody L-chain κ chain C-region had been introduced. Using the mRNA, cDNA containing the humanized PM1 antibody H-chain V-region and the human antibody C-region Cγ1 was cloned by a RT-PCR method, and then subcloned into plasmid pUC19 on the HindIII-BamHI site. After sequencing, a plasmid which had the correct nucleotide sequence was obtained, which was designated "pRVh-PM1f-cDNA".

An expression vector DHFR-ΔE-RVh-PM-1-f in which both a HindIII site between SV40 promoter and a DHFR gene and an EcoRI site between EF-1α promoter and a humanized PM1 antibody H-chain V-region gene had been deleted, was prepared for the construction of an expression vector for cDNA containing the humanized PM1 antibody H-chain V-region gene and the human antibody C-region Cγ1 gene.

The plasmid obtained (pRVh-PM1f-cDNA) was digested with BamHI, blunt-ended with Klenow fragment, and further digested with HindIII, thereby obtaining a blunt-ended HindIII-BamHI fragment. The blunt-ended HindIII-BamHI fragment was ligated to the above-mentioned HindIII site- and EcoRI site-deleted expression vector DHFR-ΔE-RVh-PM1-f that had been digested with HindIII and BamHI. Thus, an expression vector RVh-PM1f-cDNA was constructed which contained cDNA encoding the humanized PM1 antibody H-chain V-region and the human antibody C-region Cγ1.

The expression vector RVh-PM1f-cDNA containing the cDNA encoding the humanized PM1 antibody H-chain V-region and the human antibody C-region Cγ1 was digested with ApaI and BamHI, and a DNA fragment containing the H-chain C-region was collected therefrom. The resultant DNA fragment was introduced into the above-mentioned plasmid MBC1Hv/pUC19 that had been digested with ApaI and BamHI. The plasmid thus prepared was designated "MBC1HcDNA/pUC19". This plasmid contained cDNA encoding the mouse antibody H-chain V-region and the human antibody C-region Cγ1, and had EcoRI- and HindIII-recognition sequences on its 5' region and a BamHI-recognition sequence on its 3' region.

The plasmid MBC1HcDNA/pUC19 was digested with EcoRI and BamHI to give a DNA fragment comprising a nucleotide sequence encoding the chimeric antibody H-chain. The resultant DNA fragment was introduced into an expression vector pCOS1 that had been digested with EcoRI and BamHI, thereby giving an expression vector for the chimeric antibody, which was designated "MBC1HcDNA/pCOS1". Here, the expression vector pCOS1 was constructed using HEF-PMh-gγ1 (see WO 92/19759) by deleting therefrom an antibody genes by digestion with EcoRI and SmaI, and then ligating it to EcoRI-NotI-BamHI Adaptor (Takara Shuzo Co., Ltd.).

For, preparing a plasmid for the expression in a CHO cell, the plasmid MBC1HcDNA/pUC19 was digested with EcoRI and BamHI to obtain a DNA fragment containing a gene for the chimeric antibody H-chain. The DNA fragment was then introduced into an expression plasmid pCHO1 that had been digested with EcoRI and BamHI to give an expression plasmid for the chimeric antibody, which was designated "MBC1HcDNA/pCHO1". Here, the expression vector pCHO1 was constructed using DHFR-ΔE-rvH-PM1-f (see WO 92/19759) by deleting therefrom an antibody gene by digestion with EcoRI and SmaI, and then ligating it to EcoRI-NotI-BamHI Adaptor (Takara Shuzo Co., Ltd.).

(2) Construction of Human L-Chain C-Region
(i) Preparation of Cloning Vector

To construct pUC19 vector containing a gene for human L-chain C-region, a HindIII site-deleted pUC19 vector was prepared. pUC19 vector (2 μg) was digested in 20 μl of a reaction solution containing 20 mM Tris-HCl (pH 8.5), 10 mM MgCl$_2$, 1 mM DTT, 100 mM KCl, 8 U of HindIII (Takara Shuzo Co., Ltd.) at 37° C. for 1 hour. The resultant digestion solution was extracted with phenol and chloroform, and then subjected to ethanol precipitation to collect the DNA of interest.

The DNA collected was reacted in 50 μl of a reaction solution containing 50 mM Tris-HCl (pH 7.5), 10 mM MgCl$_2$, 1 mM DTT, 100 mM NaCl, 0.5 mM dNTPs and 6U of Klenow fragment (GIBCO BRL) at room temperature for 20 min., thereby rendering the terminal ends of the DNA blunt. This reaction mixture was extracted with phenol and chloroform and then subjected to ethanol precipitation to collect the vector DNA.

The vector DNA thus collected was reacted in 10 μl of a reaction solution containing 50 mM Tris-HCl (pH 7.6), 10 mM MgCl$_2$, 1 mM ATP, 1 mM DTT, 5% (v/v) polyethylene glycol-8000 and 0.5 U of T4 DNA ligase (GIBCO BRL) at 16° C. for 2 hours, to cause self-legation of the vector DNA. The reaction solution (5 μl) was added to 100 μl of a solution containing competent cells of E. coli, JM109 (Nippon Gene Co., Ltd.), and the resultant solution was allowed to stand on ice for 30 min., at 42° C. for 1 min., and further on ice for 1 min. SOC culture medium (500 μl) was added to the reaction solution and then incubated at 37° C. for 1 hour. The resultant solution was plated on 2xYT agar medium (containing 50 μg/ml of ampicillin) which had been applied with X-gal and IPTG on its surface (Molecular Cloning: A Laboratory Manual, Sambrook, et al., Cold Spring Harbor Laboratory Press, 1989), and then cultured at 37° C. overnight, thereby obtaining a transformant.

The transformant was cultured in 2xYT medium (20 ml) containing ampicillin (50 µg/ml) at 37° C. overnight. From the cell fraction of the culture medium, a plasmid DNA was isolated and purified using Plasmid Mini Kit (QIAGEN) in accordance with the instructions included in the kit. The purified plasmid was digested with HindIII. The plasmid that was confirmed to have a HindIII site-deletion was designated "pUC19 ΔHindIII".

(ii) Construction of DNA Encoding Human L-Chain λ Chain C-Region

Human antibody L-chain λ chain C-region has been known to have at least four isotypes including $Mcg^+Ke^+Oz^-$, $Mcg^-Ke^-Oz^-$, $Mcg^-Ke^-Oz^+$ and $Mcg^-Ke^+Oz^-$ (P. Dariavach, et al., Proc. Natl. Acad. Sci. USA, 84, 9074-9078, 1987). A search was made for a human antibody L-chain λ chain C-region homologous to the #23-57-137-1 mouse L-chain λ chain C-region from the EMBL database. As a result, it was found that the isotype $Mcg^+Ke^+Oz^-$ of the human antibody L-chain λ chain (Accession No. X57819) (P. Dariavach, et al., Proc. Natl. Acad. Sci. USA, 84, 9074-9078, 1987) showed the highest degree of homology to the #23-57-137-1 mouse L-chain λ chain C-region, with a 64.4% homology in terms of amino acid sequence and a 73.4% homology in terms of nucleotide sequence.

Then, a gene encoding human antibody L-chain λ chain C-region was constructed by a PCR method. The primer for the PCR was synthesized using 394 DNA/RNA Synthesizer (ABI). The synthesized primers were as follows: HLAMB1 (SEQ ID NO: 11) and HLAMB3 (SEQ ID NO: 13), both having a sense DNA sequence; and HLAMB2 (SEQ ID NO: 12) and HLAMB4 (SEQ ID NO: 14), both having an antisense DNA sequence; each primer containing a complementary sequence of 20-23 bp on the both terminal ends.

External primers HLAMBS (SEQ ID NO: 15) and HLAMBR (SEQ ID NO: 16) had sequences homologous to the primers HLAMB1 and HLAMB4, respectively. HLAMBS contained EcoRI-, HindIII- and B1nI-recognition sequences, and HLAMBR contained an EcoRI-recognition sequence. In the first PCR reaction, the reactions between HLAMB1 and HLAMB2 and between HLAMB3 and HLAMB4 were performed. After the reactions were completed, both of the resultant PCR products were mixed in equivalent quantities, and then assembled in the subsequent second PCR reaction. The reaction solution was added with the external primers HLAMBS and HLAMBR. This reaction mixture was subjected to the third PCR reaction to amplify the full length DNA.

Each PCR reaction was performed using TaKaRa Ex Taq (Takara Shuzo Co., Ltd.) in accordance with the instructions included in the kit. In the first PCR reaction, 100 µl of either a reaction solution containing 5 pmoles of HLAMB1, 0.5 pmole of HLAMB2 and 5U of TaKaRa Ex Taq (Takara Shuzo Co., Ltd.) or a reaction solution containing 0.5 pmole of HLAMB3, 5 pmoles of HLAMB4 and 5U of TaKaRa Ex Taq (Takara Shuzo Co., Ltd.) was used, over which 50 µl of mineral oil was layered. The PCR reaction was run for 5 cycles under the conditions: 94° C. for 1 min., 60° C. for 1 min. and 72° C. for 1 min.

In the second PCR reaction, a mixture of both the reaction solutions (50 µl each) was used, over which 50 µl of mineral oil was layered. The PCR reaction was run for 3 cycles under the conditions: 94° C. for 1 min., 60° C. for 1 min. and 72° C. for 1 min.

In the third PCR reaction, the reaction solution to which the external primers HLAMBS and HLAMBR (50 pmoles each) were added was used. The PCR reaction was run for 30 cycles under the conditions: 94° C. for 1 min., 60° C. for 1 min. and 72° C. for 1 min.

The DNA fragment obtained by the third PCR reaction was subjected to electrophoresis on a 3% low-melting agarose gel (NuSieve GTG Agarose, FMC), and separated and purified from the gel using GENECLEAN II Kit (BIO101) in accordance with the instructions included in the kit.

The DNA fragment obtained was digested in a reaction solution (20 µl) containing 50 mM Tris-HCl (pH 7.5), 10 mM $MgCl_2$, 1 mM DTT, 100 mM NaCl and 8U of EcoRI (Takara Shuzo Co., Ltd.) at 37° C. for 1 hour. The digestion solution was extracted with phenol and chloroform, and the DNA was collected therefrom by the ethanol precipitation. The DNA was dissolved in a solution (8 µl) containing 10 mM Tris-HCl (pH 7.4) and 1 mM EDTA.

The above-prepared plasmid pUC19 ΔHindIII (0.8 µg) was digested with EcoRI in the same manner as mentioned above. The digestion solution was subjected to phenol/chloroform extraction and then ethanol precipitation, thereby giving a digested plasmid pUC19 ΔHindIII. The digested plasmid was reacted in a reaction solution (50 µl) containing 50 mM Tris-HCl (pH 9.0), 1 mM $MgCl_2$ and alkaline phosphatase (E. coli C75; Takara Shuzo Co., Ltd.) at 37° C. for 30 min. to dephosphorylate (i.e., BAP-treat) the plasmid. The reaction solution was subjected to phenol/chloroform extraction, and the DNA was collected therefrom by ethanol precipitation. The DNA thus obtained was dissolved in a solution (10 µl) containing 10 mM Tris-HCl (pH 7.4) and 1 mM EDTA.

The BAP-treated plasmid pUC19 ΔHindIII (1 µl) was ligated to the above-obtained PCR product (4 µl) using DNA Ligation Kit Ver.2 (Takara Shuzo Co., Ltd.). The resultant plasmid was introduced into a competent cell of E. coli, JM109, to give a transformant. The transformant was cultured overnight in 2xYT medium (2 ml) containing 50 µg/ml of ampicillin. From the cell fraction, the plasmid was isolated using QIAprep Spin Plasmid Kit (QIAGEN).

The plasmid obtained was sequenced for the cloned DNA portion. The sequencing was performed in 373A DNA Sequencer (ABI) using M13 Primer M4 and M13 Primer RV (Takara Shuzo Co., Ltd.). As a result, it was found that the cloned DNA had a 12-bp deletion therein. The plasmid was designated "CλΔ/pUC19". Then, for making up for the deleted portion, primers HCLMS (SEQ ID NO: 17) and HCLMR (SEQ ID NO: 18) were newly synthesized, and correct DNA was reconstructed using these primers by a PCR method.

In the first PCR reaction, the plasmid CλΔ/pUC19 having the DNA deletion therein was used as a template, and the reaction was performed with each of the primer sets of HLAMBS and HCLMS and HCLMS and HLAMB4. The PCR products were purified separately. In the second PCR reaction, the PCR products were assembled together. In the third PCR reaction, the reaction product of the second PCR reaction was added with external primers HLAMBS and HLAMB4 and amplified to give the full length DNA.

In the first PCR reaction, a reaction solution (100 µl) containing 0.1 µg of CλΔ/pUC19 as a template, either 50 pmoles of each of the primers HLAMBS and HCLMR or 50 pmoles of each of the primers HCLMS and HLAMB4, and 5U of TaKaRa Ex Taq (Takara Shuzo Co., Ltd.) was used, over which 50 µl of mineral oil was layered. The PCR reaction was run for 30 cycles under the conditions: 94° C. for 1 min., 60° C. for 1 min. and 72° C. for 1 min.

The PCR products of the first PCR reaction, HLAMBS-HCLMR (236 bp) and HCLMS-HLAMB3 (147 bp), were subjected to electrophoresis separately on a 3% low-melting agarose gel to isolate the DNA fragments. The DNA fragments were collected and purified from the gels using GENECLEAN II Kit (BIO101). In the second PCR reaction, 20 μl of a reaction solution containing 40 ng of each of the purified DNA fragments and 1U of TaKaRa Ex Taq (Takara Shuzo Co., Ltd.) was used, over which 25 μl of mineral oil was layered. The PCR reaction was run for 5 cycles under the conditions: 94° C. for 1 min., 60° C. for 1 min. and 72° C. for 1 min.

In the third PCR reaction, 100 μl of a reaction solution containing 2 μl of the reaction solution obtained by the second PCR reaction, 50 pmoles of each of external primers HLAMBS and HLAMB4 and 5U of TaKaRa Ex Taq (Takara Shuzo Co., Ltd.) was used, over which 50 μl of mineral oil was layered. The PCR reaction was run for 30 cycles under the conditions: 94° C. for 1 min., 60° C. for 1 min. and 72° C. for 1 min., thereby obtaining a DNA fragment of 357 bp (the third PCR product). The DNA fragment was subjected to electrophoresis on a 3% low-melting agarose gel to isolate the DNA fragment. The resultant DNA fragment was collected and purified using GENECLEAN Kit (BIO101).

A portion (0.1 μg) of the DNA fragment thus obtained was digested with EcoRI, and then subcloned into plasmid pUC19 ΔHindIII that had been BAP-treated. The resultant plasmid was introduced into a competent cell of *E. coli*, JM109, to form a transformant. The transformant was cultured overnight in 2 ml of 2xYT medium containing 50 μg/ml of ampicillin. From the cell fraction, the plasmid was isolated and purified using QIAprep Spin Plasmid Kit (QIAGEN).

The purified plasmid was sequenced in 373A DNA Sequencer (ABI) using M13 Primer M4 and M13 Primer RV (Takara Shuzo Co., Ltd.). The plasmid that was confirmed to have the correct nucleotide sequence without any deletion was designated "Cλ/pUC19".

(iii) Construction of Gene Encoding Human L-Chain κ Chain C-Region

A DNA fragment encoding the L-chain κ chain C-region was cloned from plasmid HEF-PM1k-gk (WO 92/19759) by a PCR method. A forward primer HKAPS (SEQ ID NO: 19) was designed to contain EcoRI-, HindIII and BlnI-recognition sequences, and a backward primer HKAPA (SEQ ID NO: 20) was designed to contain an EcoRI-recognition sequence. These primers were synthesized in 394 DNA/RNA Synthesizer (ABI).

A PCR reaction was performed using 100 μl of a reaction solution containing 0.1 μg of plasmid HEF-PM1k-gk as a template, 50 pmoles of each of primers HKAPS and HKAPA and 5U of TaKaRa Ex Taq (Takara Shuzo Co., Ltd.), over which 50 μl of mineral oil was layered. The PCR reaction was run for 30 cycles under the conditions: 94° C. for 1 min., 60° C. for 1 min. and 72° C. for 1 min., thereby giving a PCR product of 360 bp. The DNA fragment was isolated and purified by electrophoresis on a 3% low-melting agarose, and then collected and purified using GENECLEAN II Kit (BIO101).

The DNA fragment thus obtained was digested with EcoRI, and then cloned into plasmid pUC19 ΔHindIII that had been BAP-treated. The resultant plasmid was introduced into a competent cell of *E. coli*, JM109, to form a transformant. The transformant was cultured overnight in 2 ml of 2xYT medium containing 50 μg/ml of ampicillin. From the cell fraction, the plasmid was purified using QIAprep Spin Plasmid Kit (QIAGEN).

The purified plasmid was sequenced in 373A DNA Sequencer (ABI) using M13 Primer M4 and M13 Primer RV (Takara Shuzo Co., Ltd.). The plasmid that was confirmed to have the correct nucleotide sequence was designated "Cκ/pUC19".

(3) Construction of Chimeric Antibody L-Chain Expression Vector

An expression vector for the chimeric #23-57-137-1 antibody L-chain was constructed. A gene encoding #23-57-137-1 L-chain V-region was ligated to the HindIII-BlnI site (located just in front of the human antibody C-region) of each of the plasmids Cλ/pUC19 and Cκ/pUC19, thereby obtaining pUC19 vectors containing the DNA encoding the chimeric #23-57-137-1 antibody L-chain V-region and either of the L-chain λ chain C-region or the L-chain κ region C-region, respectively. Each of the resultant vectors was then digested with EcoRI to separate the gene for the chimeric antibody L-chain. The gene was subcloned into HEF expression vector.

That is, a DNA fragment encoding #23-57-137-1 antibody L-chain V-region was cloned from plasmid MBC1L24 by a PCR method. Primers used in the PCR method were separately synthesized using 394 DNA/RNA Synthesizer (ABI). A backward primer MBCCHL1 (SEQ ID NO: 21) was designed to contain a HindIII-recognition sequence and a Kozak sequence (Kozak, M. et al., J. Mol. Biol. 196, 947-950, 1987), and a forward primer MBCCHL3 (SEQ ID NO: 22) was designed to contain BglII- and RcoRI-recognition sequences.

The PCR reaction was performed using 100 μl of a reaction solution containing 10 mM Tris-HCl (pH 8.3), 50 mM KCl, 1.5 mM MgCl$_2$, 0.2 mM dNTPs, 0.1 μg MBC1L24, 50 pmoles of each of primers MBCCHL1 and MBCCHL3 and 1 μl of AmpliTaq (PERKIN ELMER), over which 50 μl of mineral oil was layered. The PCR reaction was run for 30 cycles under the conditions: 94° C. for 45 sec., 60° C. for 45 sec. and 72° C. for 2 min.

A PCR product of 444 bp was electrophoresed on a 3% low-melting agarose gel, and collected and purified using GENECLEAN II Kit (BIO101). The purified PCR product was dissolved in 20 μl of a solution containing 10 mM Tris-HCl (pH 7.4) and 1 mM EDTA. The PCR product (1 μl) was digested in 20 μl of a reaction solution containing 10 mM Tris-HCl (pH 7.5), 10 mM MgCl$_2$, 1 mM DTT, 50 mM NaCl, 8U of HindIII (Takara Shuzo Co., Ltd.) and 8U of EcoRI (Takara Shuzo Co., Ltd.) at 37° C. for 1 hour. The digestion solution was subjected to phenol/chloroform extraction, and the DNA of interest was collected therefrom by ethanol precipitation. The DNA was dissolved in 8 μl of a solution containing 10 mM Tris-HCl (pH 7.4) and 1 mM EDTA.

In the same manner, plasmid pUC19 (1 μg) was digested with HindIII and EcoRI, and subjected to phenol/chloroform extraction and then ethanol precipitation. The obtained digested plasmid was BAP-treated with alkaline phosphatase (*E. coli* C75; Takara Shuzo Co., Ltd.). The resultant reaction solution was extracted with phenol and chloroform, and the DNA was collected therefrom by ethanol precipitation. The DNA was dissolved in 10 μl of a solution containing 10 mM Tris-HCl (pH 7.4) and 1 mM EDTA.

The BAP-treated plasmid pUC19 (1 μl) was ligated to the above-obtained PCR product (4 μl) using DNA Ligation Kit Ver. 2 (Takara Shuzo Co., Ltd.). The resultant plasmid was introduced into a competent cell of *E. coli*, JM109 (Nippon Gene Co., Ltd.), in the same manner as mentioned above, to form a transformant. The transformant was plated on 2xYT agar medium containing 50 μg/ml of ampicillin and cultured at 37° C. overnight. The resultant transformant was then cultured at 37° C. overnight in 2 ml of 2xYT medium containing 50 µg/ml of ampicillin. From the cell fraction, the plasmid was purified using QIAprep Spin Plasmid Kit (QIAGEN). After determining the nucleotide sequence, the plasmid that was confirmed to have the correct nucleotide sequence was designated "CHL/pUC19".

Each of plasmids Cλ/pUC19 and Cκ/pUC19 (1 µg each) was digested in 20 µl of a reaction solution containing 20 mM Tris-HCl (pH 8.5), 10 mM MgCl$_2$, 1 mM DTT, 100 mM KCl, 8U of HindIII (Takara Shuzo Co., Ltd.) and 2U of BlnI (Takara Shuzo Co., Ltd.) at 37° C. for 1 hour. The digestion solution was extracted with phenol and chloroform, and the DNA was collected therefrom by ethanol precipitation. The DNA was BAP-treated at 37° C. for 30 min. The reaction solution was extracted with phenol and chloroform, and the DNA was collected therefrom by ethanol precipitation. The DNA was dissolved in 10 µl of a solution containing 10 mM Tris-HCl (pH 7.4) and 1 mM EDTA.

The plasmid CHL/pUC19 that contained DNA encoding #23-57-137-1 L-chain V-region (8 µg) was digested with HindIII and BlnI in the same manner as mentioned above to give a DNA fragment of 409 bp. The DNA fragment was electrophoresed on a 3% low-melting agarose gel, and then collected and purified using GENECLEAN II Kit (BIO101) from the gel. The DNA was dissolved in 10 µl of a solution containing 10 mM Tris-HCl (pH 7.4) and 1 mM EDTA.

The DNA for L-chain V-region DNA (4 µl) was subcloned into 1 µl of each of the BAP-treated plasmids Cλ/pUC19 and CK/pUC19, and then introduced into a competent cell of *E. coli*, JM109, to form a transformant. The transformant was cultured overnight in 3 ml of 2xYT medium containing 50 µg/ml of ampicillin. From the cell fraction, the plasmid was isolated and purified using QIAprep Spin Plasmid Kit (QIAGEN). The two plasmids thus prepared were designated "MBC1L(λ)/pUC19" and "MBC1L(κ)/pUC19", respectively.

Each of plasmids MBC1L(λ)/pUC19 and MBC1L(κ)/pUC19 was digested with EcoRI and then subjected to electrophoresis on a 3% low-melting agarose gel. A DNA fragment of 743 bp was isolated and purified from the gel using GENECLEANII Kit (BIO101), and then dissolved in 10 µl of a solution containing 10 mM Tris-HCl (pH 7.4) and 1 mM EDTA.

An expression vector (plasmid HEF-PM1k-gk) (2.7 µg) was digested with EcoRI and then extracted with phenol and chloroform, and the DNA was collected therefrom by ethanol precipitation. The DNA fragment was BAP-treated, and then subjected to electrophoresis on a 1% low-melting agarose gel. From the gel, a DNA fragment of 6561 bp was isolated and purified therefrom using GENECLEANII Kit (BIO101). The purified DNA fragment was dissolved in 10 µl of a solution containing 10 mM Tris-HCl (pH 7.4) and 1 mM EDTA.

BAP-treated HEF vector (2 µl) was ligated to an EcoRI fragment (3 µl) of each of plasmid MBC1L(λ)/pUC19 and MBC1L(κ)/pUC19. The ligation product was introduced into a competent cell of *E. coli*, JM109, to form a transformant. The transformant was cultured in 2 ml of 2xYT medium containing 50 µg/ml of ampicillin. From the cell fraction, the plasmid was purified using QIAprep Spin Plasmid Kit (QIAGEN).

The purified plasmid was digested in 20 µl of a reaction solution containing 20 mM Tris-HCl (pH 8.5), 10 mM MgCl$_2$, 1 mM DTT, 100 mM KCl, 8U of HindIII (Takara Shuzo Co., Ltd.) and 2 U of PvuI (Takara Shuzo Co., Ltd.) at 37° C. for 1 hour. This reaction gave digestion fragments of 5104/2195 bp if the fragment was inserted in the correct orientation, or gave digestion fragments of 4378/2926 bp if the fragment was inserted in the reverse orientation. The plasmid that was confirmed to have the fragment in the correct orientation was designated "MBC1L(λ)/neo" for plasmid MBC1L(λ)/pUC19 or "MBC1L(κ)/neo" for plasmid MBC1L(κ)/pUC19.

(4) Transfection of COS-7 Cell

To evaluate the antigen-binding activity and the neutralizing activity of the chimeric antibodies, the expression plasmids prepared above were separately expressed transiently in a COS-7 cell.

The transient expression of the chimeric antibodies was performed using each of the combinations of plasmids MBC1HcDNA/pCOS1 and MBC1L (λ)/neo and plasmids MBC1HcDNA/pCOS1 and MBC1L(κ)/neo, by co-tansfecting a COS-7 cell with the plasmids by electroporation using Gene Pulser (Bio Rad). That is, the plasmids (10 µg each) were added to a COS-7 cell suspension (0.8 ml; 1×10$^7$ cells/ml) in PBS(–). The resultant solution was applied with pulses at an electrostatic capacity of 1,500V and 2 µF to cause electroporation. After 10 min. of recovery period at room temperature, the electroporated cells were suspended in DMEM medium (GIBCO) containing 2% Ultra Low IgG fetal calf serum (GIBCO), and then cultured using a 10-cm culture dish in a CO$_2$ incubator. After cultivating for 72 hours, a culture supernatant was collected and centrifuged to remove cell debris and was provided for use as a sample for the subsequent ELISA. In this procedure, the purification of the chimeric antibody from the COS-7 cell culture supernatant was performed using AffiGel Protein A MAPSII Kit (Bio Rad) in accordance with the instructions included in the kit.

(5) ELISA (i) Determination of Antibody Concentration

An ELISA plate for determining antibody concentration was prepared as follows. Each well of a 96-well ELISA plate (Maxisorp, NUNC) was coated with 100 µl of a coating buffer (0.1 M NaHCO$_3$, 0.02% NaN$_3$) supplemented with 1 µg/ml of goat anti-human IgG antibody (TAGO), and then blocked with 200 µl of a dilution buffer [50 mM Tris-HCl, 1 mM MgCl$_2$, 0.1 M NaCl, 0.05% Tween 20, 0.02% NaN$_3$, 1% bovine serum albumin (BSA); pH 7.2]. Each well of the plate was added with each of the serial dilutions of the COS-7 cell culture supernatant in which each of the chimeric antibodies had been expressed, or added with each of the serial dilutions of each of the chimeric antibodies per se in a purified form. The plate was incubated at room temperature for 1 hour and washed with PBS-Tween 20. Each well of the plate was then added with 100 µl of a solution of alkaline phosphatase-conjugated goat anti-human IgG antibodies (TAGO). After the plate was incubated at room temperature for 1 hour and washed with PBS-Tween 20, each well was added with 1 mg/ml of a substrate solution ("Sigma 104", p-nitrophenylphosphoric acid, SIGMA). The solution was measured on its absorbance at 405 nm using Microplate Reader (Bio Rad) to determine the antibody concentration. In this determination, Hu IgG1λ Purified (The Binding Site) was used as the standard.

(ii) Determination of Antigen-Binding Ability

An ELISA plate for the determination of antigen-binding ability was prepared as follows. Each well of a 96-well ELISA plate was coated with 100 µl of a coating buffer supplemented with 1 µg/ml of human PTHrP (1-34) (Peptide Research Institute), and then blocked with 200 µl of a dilution buffer. Each well was added with each of the serial dilutions of the COS-7 cell culture supernatant in which each of the chimeric antibodies had been expressed, or added with each of the serial dilutions of each of the chimeric antibodies per se in a purified form. After the plate was incubated at room temperature and washed with PBS-Tween 20, each well of the plate was added with 100 μl of a solution of alkaline phosphatase-conjugated goat anti-human IgG antibodies (TAGO). After the plate was incubated at room temperature and washed with PBS-Tween 20, each well of the plate was added with 1 mg/ml of a substrate solution ("Sigma 104", p-nitrophenylphosphoric acid, SIGMA). The solution was measured on its absorbance at 405 nm using Microplate Reader (Bio Rad).

Figure 5:
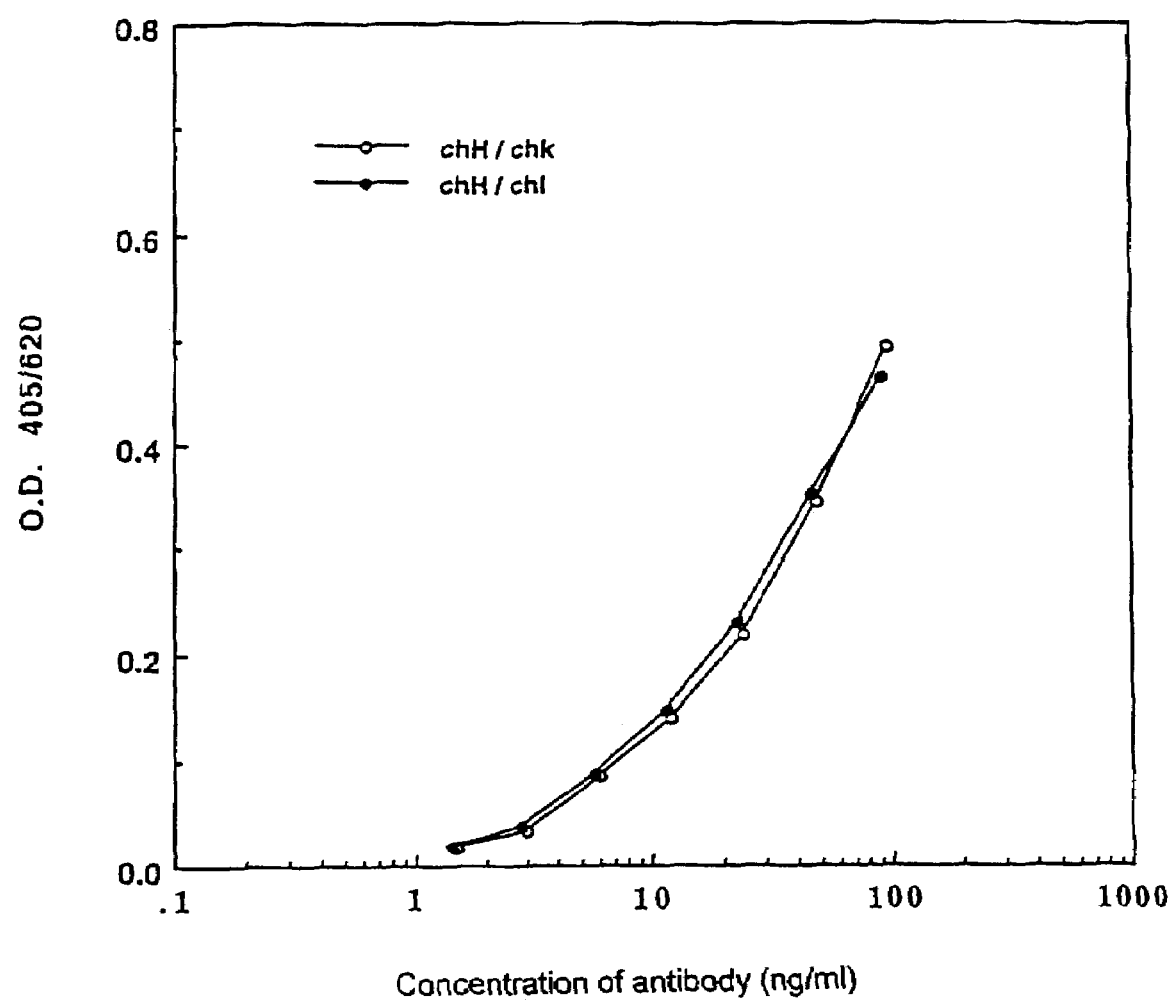
FIG. 5. is a graphical illustration of the measurement results of the antigen-binding activity. "chH/chk" refers to the chimeric antibody with L-chain k chain C-region, while "chH/chk" refers to the chimeric antibody with L-chain λ chain C-region.

As a result, it was found that the chimeric antibodies had an ability to bind to human PTHrP (1-34) and the cloned mouse antibody V-regions had the correct structures (FIG. 5). It was also found that there was no difference in the ability to bind to PTHrP (1-34) between the chimeric antibody with L-chain λ chain C-region and the chimeric antibody with L-chain κ chain C-region. Therefore, the L-chain C-region of the humanized antibody was constructed using the humanized antibody L-chain λ chain.

(6) Establishment of CHO Cell Line Capable of Stable Production of Chimeric Antibodies To establish a cell line capable of producing the chimeric antibodies stably, the above-prepared expression plasmids were introduced into CHO cells (DXB11).

For the establishment of a cell line capable of producing the chimeric antibodies stably, either of the following combinations of the expression plasmids for CHO cell was used: MBC1HcDNA/pCHO1 and MBC1L(λ)/neo; and MBC1HcDNA/pCHO1 and MBC1L(κ)/neo. A CHO cell was co-transfected with the plasmids by electroporation using Gene Pulser (Bio Rad) as follows. The expression vectors were separately cleaved with a restriction enzyme PvuI to give linear DNAs. The resultant DNAs were extracted with phenol and chloroform and collected by precipitation with ethanol. The plasmid DNAs thus prepared were subjected to electroporation. That is, each of the plasmid DNAs (10 μg each) was added to 0.8 ml of a cell suspension of CHO cells in PBS(-) ($1\times10^7$ cells/ml). The resultant solution was applied with pulses at an electrostatic capacity of 1,500V and 25 μF. After 10 min. of recovery period at room temperature, the electroporated cells were suspended in MEM-α medium (GIBCO) containing 10% fetal calf serum (GIBCO). The resultant suspension was cultured using three 96-well plates (Falcon) in a $CO_2$ incubator. On the day after starting the cultivation, the medium was replaced by a selective medium [ribonucleoside- or deoxyribonucleoside-free MEM-medium (GIBCO) containing 10% fetal calf serum (GIBCO) and 500 mg/ml of GENETICIN (G418Sulfate; GIBCO)]. From the culture medium, cells into which the antibody gene was introduced were selected. The selective medium is replaced by a fresh one. About two weeks after the medium replacement, the cells were observed under a microscope. When a favorable cell growth was observed, the cells were determined on the amount of the produced antibodies by ELISA as mentioned above. Among the cells, those which produced a larger amount of antibodies were screened.

Then, the cultivation of the established cell line capable of stable production of the antibodies was scaled up in a roller bottle using ribonucleoside- or deoxyribonucleoside-free MEM medium containing 2% Ultra Low IgG fetal calf serum. On day 3 and day 4 of the cultivation, the culture supernatant was collected and then filtered using a 0.2-μm filter (Millipore) to remove cell debris therefrom.

Purification of the chimeric antibodies from the CHO cell culture supernatant was performed using POROS Protein A Column (PerSeptive Biosystems) on ConSep LC100 (Millipore) in accordance with the instructions included in the kit. The purified chimeric antibodies were provided for use as samples for the determination of neutralizing activity and for the examination of therapeutic efficacy on hypercalcemic model animals. The concentration and the antigen-binding activity of the purified chimeric antibodies were determined using the same ELISA system as mentioned above.

REFERENCE EXAMPLE 4

Construction of Humanized Antibody (1) Construction of Humanized Antibody H-Chain
(i) Construction of Humanized H-Chain V-Region A humanized #23-57-137-1 antibody H-chain was produced by CDR-grafting technique by means of a PCR method. For the production of a humanized #23-57-137-1 antibody H-chain (version "a") having FRs derived from human antibody S31679 (NBRF-PDB; Cuisinier, A. M. et al., Eur. J. Immunol., 23, 110-118, 1993), the following six PCR primers were used: CDR-grafting primers: MBC1HGP1 (SEQ ID NO: 23) and MBC1HGP3 (SEQ ID NO: 24) (both containing a sense DNA sequence) and MBC1HGP2 (SEQ ID NO: 25) and MBC1HGP4 (SEQ ID NO: 26) (both containing an antisense DNA sequence), all of which containing a 15-21 bp complementary sequence on both terminal ends thereof; and external primers: MBC1HVS1 (SEQ ID NO: 27) and MBC1HVR1 (SEQ ID NO: 28) having a homology to the CDR-grafting primers MBC1HGP1 and MBC1HGP4, respectively.

The CDR-grafting primers MBC1HGP1, MBC1HGP2, MBC1HGP3 and MBC1HGP4 were separated on an urea-denatured polyacrylamide gel (Molecular Cloning: A Laboratory Manual, Sambrook, et al., Cold Spring Harbor Laboratory Press, 1989), and extracted therefrom by a crush-and-soak method (Molecular Cloning: A Laboratory Manual, Sambrook, et al., Cold Spring Harbor Laboratory Press, 1989) in the following manner.

Each of the CDR-grafting primers (1 nmole) was separated on a 6% denatured polyacrylamide gel to give DNA fragments. From the resultant DNA fragments, one having a desired length was identified on a silica gel thin plate by irradiation of UV ray and then collected therefrom by a crush-and-soak method. The resultant DNA was dissolved in 20 μl of a solution containing 10 mM Tris-HCl (pH 7.4) and 1 mM EDTA. The PCR reaction was performed using TaKaRa Ex Taq (Takara Shuzo Co., Ltd.). The PCR reaction solution (100 μl) comprised 1 μl of each of the above-mentioned CDR-grafting primers MBC1HGP1, MBC1HGP2, MBC1HGP3 and MBC1HGP4, 0.25 mM dNTPs and 2.5U of TaKaRa Ex Taq in the buffer. The PCR reaction was run for 5 cycles under the conditions: 94° C. for 1 min., 55° C. for 1 min. and 72° C. for 1 min. The resultant reaction solution was added with the external primers MBC1HVS1 and MBC1HVR1 (50 pmoles each). Using this reaction mixture, the PCR reaction was further run for additional 30 cycles under the same conditions. The DNA fragment thus amplified was separated by agarose gel electrophoresis on a 4% Nu Sieve GTG agarose (FMC Bio. Products).

An agarose segment containing a DNA fragment of 421 bp was excised, and the DNA fragment was purified therefrom using GENECLEANII Kit (BIO101) in accordance with the instructions included in the kit. The DNA fragment thus purified was precipitated with ethanol and then dissolved in 20 μl of a solution containing 10 mM Tris-HCl (pH 7.4) and 1 mM EDTA. The resultant PCR reaction mixture was used for subcloning of the DNA fragment into plasmid pUC19 that had been digested with BamHI and HindIII, and subsequently the nucleotide sequence of the resultant plasmid was determined. A plasmid having the correct nucleotide sequence was designated "hMBCHv/pUC19".

(ii) Construction of H-Chain V-Region for Humanized H-Chain cDNA

To ligate to cDNA for humanized H-chain C-region Cγ1, the DNA for the humanized H-chain V-region constructed in the above step was modified by a PCR method. For the PCR method, a backward primer MBC1HVS2 was designed to hybridize to the sequence encoding the 5' region of the leader sequence for the V-region and to have a Kozak consensus sequence (Kozak et al., J. Mol. Biol. 196, 947-950, 1987) and HindIII- and EcoRI-recognition sequences; and a forward primer MBC1HVR2 was designed to hybridize to both the DNA sequence encoding the 3' region of the J region and the DNA sequence encoding the 5' region of the C-region and to have ApaI- and SmaI-recognition sequences.

The PCR reaction was performed using TaKaRa Ex Taq (Takara Shuzo Co., Ltd.) and a buffer appended thereto. The PCR reaction solution comprised 0.4 μg of hMBCHv/pUC19 as a DNA template, 50 pmoles of each of MBC1HVS2 and MBC1HVR2 as primers, 2.5U of TaKaRa Ex Taq and 0.25 mM dNTPs in the buffer. The PCR reaction was run for 30 cycles under the conditions: 94° C. for 1 min., 55° C. for 1 min. and 72° C. for 1 min. The DNA fragment thus amplified was separated by agarose gel electrophoresis on a 3% Nu Sieve GTG agarose (FMC Bio. Products).

A gel segment containing a DNA fragment of 456 bp was excised, and the DNA fragment was purified therefrom using GENECLEANII Kit (BIO101) in accordance with the instructions included in the kit. The DNA fragment thus purified was precipitated with ethanol and then dissolved in 20 μl of a solution containing 10 mM Tris-HCl (pH 7.4) and 1 mM EDTA. The PCR reaction solution thus obtained was used for subcloning of the DNA fragment into plasmid pUC19 that had been digested with EcoRI and SmaI, and then the resultant plasmid was sequenced. As a result, a plasmid was obtained which contained DNA encoding mouse H-chain V-region derived from hybridoma #23-57-137-1 and also contained EcoRI- and HindIII-recognition sequences and a Kozak sequence on the 5' region and ApaI- and SmaI-recognition sequences on the 3' region, which was designated "hMBC1Hv/pUC19".

(2) Construction of Expression Vector for Humanized Antibody H-Chain

Plasmid RVh-PM1f-cDNA carrying a cDNA sequence for hPM1 antibody H-chain was digested with ApaI and BamHI to give a DNA fragment containing a DNA fragment containing DNA encoding the H-chain C-region. The DNA fragment was introduced into plasmid hMBC1Hv/pUC19 that had been digested with ApaI and BamHI. The obtained plasmid was designated "hMBC1HcDNA/pUC19". This plasmid contained both DNA encoding the humanized #23-57-137-1 antibody H-chain V-region and DNA encoding the human H-chain C-region Cγ1 and had EcoRI- and HindIII-recognition sequences on the 5' region and a BamHI-recognition sequence on the 3' region. The nucleotide sequence and the corresponding amino acid sequence for the humanized H-chain version "a" carried on the plasmid hMBC1HcDNA/pUC19 are shown in SEQ ID NO: 58 and SEQ ID NO: 56, respectively.

The plasmid hMBC1HcDNA/pUC19 was digested with EcoRI and BamHI to give a DNA fragment containing DNA encoding the H-chain. The DNA fragment was introduced into expression plasmid pCOS1 that had been digested with EcoRI and BamHI. As a result, an expression plasmid for a humanized antibody was obtained, which was designated "hMBC1HcDNA/pCOS1".

To produce a plasmid used for expression in a CHO cell, plasmid hMBC1HcDNA/pUC19 was digested with EcoRI and BamHI to give a DNA fragment containing DNA encoding the H-chain. The DNA fragment was introduced into expression vector pCHO1 that had been digested with EcoRI and BamHI. As a result, an expression plasmid for the humanized antibody was obtained, which was designated "hMBC1HcDNA/pCHO1".

(3) Construction of L-Chain Hybrid V-Region
(i) Preparation of FR1, 2/FR3, 4 Hybrid Antibody A gene for the FR hybrid L-chain having both FRs from a humanized antibody and FRs from a mouse (chimeric) antibody was constructed, and evaluated each region for humanization. In this step, a hybrid antibody having FR1 and FR2 both derived from a human antibody and FR3 and FR4 both derived from a mouse antibody was prepared by utilizing the AflII restriction site located on CDR2.

Plasmids MBC1L(λ)/neo and hMBC1L(λ)/neo (10 μg each) were separately digested in 100 μl of a reaction solution containing 10 mM Tris-HCl (pH 7.5), 10 mM MgCl$_2$, 1 mM DTT, 50 mM NaCl, 0.01% (w/v) of BSA and 10 U of AflII (Takara Shuzo Co., Ltd.) at 37° C. for 1 hour. The reaction solutions were subjected to electrophoresis on a 2% low-melting agarose gel, thereby giving DNA fragments of 6282 bp (referred to as "c1") and 1022 bp (referred to as "c2") from the plasmid MBC1L(λ)/neo or DNA fragments of 6282 bp (referred to as "h1") and 1022 bp (referred to as "h2") from the plasmid hMBC1L(λ)/neo. These DNA fragments were collected and purified from the gels using GENECLEANII Kit (BIO101).

Each of the c1 and h1 fragments (1 μg) was BAP-treated. The DNA fragment was extracted with phenol and chloroform, collected by ethanol precipitation, and dissolved in 10 μl of a solution containing 10 mM Tris-HCl (pH 7.4) and 1 mM EDTA.

The BAP-treated c1 and h1 DNA fragments (1 μl each) were ligated to the h2 and c2 DNA fragments (4 μl each), respectively, (at 4° C. overnight). Each of the ligation products was introduced into a competent cell of E. coli, JM109, to form a transformant. The transformant was cultured in 2 ml of 2xYT medium containing 50 μg/ml of ampicillin. From the cell fraction, the plasmid was purified using QIAprep Spin Plasmid Kit (QIAGEN).

The purified plasmid was digested in 20 μl of a reaction solution containing 10 mM Tris-HCl (pH 7.5), 10 mM MgCl$_2$, 1 mM DTT, and either 2U of ApaLI (Takara Shuzo Co., Ltd.) or 8U of BamHI (Takara Shuzo Co., Ltd.) and HindIII (Takara Shuzo Co., Ltd.) at 37° C. for 1 hour. If the c1-h2 was ligated correctly, this digestion reaction gave fragments of 5560/1246/498 bp (by the ApaLI digestion) or fragments of 7134/269 bp (by the BamHI/HindIII digestion). Based on this assumption, the desired plasmids were identified.

The expression vector encoding the human FR1, 2/mouse FR3, 4 hybrid antibody L-chain was designated "h/mMBC1L (λ)/neo". On the other hand, a clone for the h1-c1 could not be obtained. Therefore, recombination on a pUC vector was performed, and then the resultant recombinant product was cloned into a HEF vector. In this procedure, plasmid hMBC1Laλ/pUC19, which contained DNA encoding a humanized antibody L-chain V-region without any amino acid replacements, and plasmid hMBC1Ldλ/pUC19, which contained DNA encoding a humanized antibody L-chain V-region with an amino acid replacement at the 91-position amino acid tyrosine in FR3 (i.e., the 87th amino acid in accordance with The Kabat's prescription) by isoleucine, were used as templates.

Plasmids MBC1L(λ)/pUC19, hMBC1Laλ/pUC19 and hMBC1Ldλ/pUC19 (10 µl each) were separately digested in 30 µl of a reaction solution containing 10 mM Tris-HCl (pH 7.5), 10 mM MgCl$_2$, 1 mM DTT, 50 mM NaCl, 0.01% (w/v) of BSA, 16U of HindIII and 4U of AflII at 37° C. for 1 hour. The reaction solutions were separately subjected to electrophoresis on a 2% low-melting agarose gel, thereby giving a DNA fragment 215 bp from plasmid MBC1L(λ)/pUC19 (referred to as "c2'") and a DNA fragment of 3218 bp from each of plasmids hMBC1Laλ/pUC19 and hMBC1Ldλ/pUC19 (referred to as "ha1'" and "hd1'", respectively). These DNA fragments were collected and purified using GENECLEANII Kit (BIO101).

Each of the ha1' and hd1' fragments was ligated to the c2' fragment and then introduced into a competent cell of *E. coli*, JM109, to form a transformant. The transformant was cultured in 2 ml of 2xYT medium containing 50 µg/ml of ampicillin. From the cell fraction, the plasmid was purified using QIAprep Spin Plasmid Kit (QIAGEN). The plasmids thus prepared were designated "m/hMBC1Laλ/pUC19" for the ha1' fragment-containing plasmid and "m/hMBC1Ldλ/pUC19" for the hd1' fragment-containing plasmid.

Each of the plasmids m/hMBC1Laλ/pUC19 and m/hMBC1Ldλ/pUC19 was digested with EcoRI. The DNA fragment of 743 bp was electrophoresed on a 2% low-melting agarose gel, and then collected and purified therefrom using GENECLEANII Kit (BIO101). The resultant DNA-fragment was dissolved in 20 µl of a solution containing 10 mM Tris-HCl (pH 7.4) and 1 mM EDTA.

Each of the DNA fragments (4 µl each) was ligated to the above-obtained BAP-treated HEF vector (1 µl). The ligation product was introduced into a competent cell of *E. coli*, JM109, to form a transformant. The transformant was cultured in 2 ml of 2xYT medium containing 50 µg/ml of ampicillin. From the cell fraction, the plasmid was purified using QIAprep Spin Plasmid Kit (QIAGEN).

Each of the purified plasmids was digested in 20 µl of a reaction solution containing 20 mM Tris-HCl (pH 8.5), 10 mM MgCl$_2$, 1 mM DTT, 100 mM KCl, 8U of HindIII (Takara Shuzo Co., Ltd.) and 2U of PvuI (Takara Shuzo Co., Ltd.) at 37° C. for 1 hour. The plasmid DNA was identified based on the expectation that if the DNA fragment was inserted in the plasmid in a correct orientation, this digestion would give a digestion fragment of 5104/2195 bp, whereas if the DNA fragment is inserted in the plasmid in the reverse orientation, this digestion would give a digestion fragment of 4378/2926 bp. The plasmids thus obtained were expression vectors coding for mouse FR1, 2/human FR3, 4 hybrid antibody L-chain, which were designated expression vectors "m/hMBC1Laλ/neo" and "m/hMBC1Ldλ/neo", respectively.

(ii) Preparation of FR1/FR2 Hybrid Antibody

An FR1/FR2 hybrid antibody was prepared in the same manner as mentioned above utilizing a SnaBI restriction site located on CDR1.

Plasmids MBC1L(λ)/neo and h/mMBC1L(λ)/neo (10 µg each) were separately digested in 20 µl of a reaction solution containing 10 mM Tris-HCl (pH 7.9), 10 mM MgCl$_2$, 1 mM DTT, 50 mM NaCl, 0.01% (w/v) of BSA and 6U of SnaBI (Takara Shuzo Co., Ltd.) at 37° C. for 1 hour. The resultant reaction solutions were further digested in 50 µl of a reaction solution containing 20 mM Tris-HCl (pH 8.5), 10 mM MgCl$_2$, 1 mM DTT, 100 mM KCl, 0.01% (w/v) of BSA and 6U of PvuI at 37° C. for 1 hour.

The resultant reaction solutions were separately subjected to electrophoresis on a 1.5% low-melting agarose gel, thereby giving DNA fragments of 4955 bp (m1) and 2349 bp (m2) from the plasmid MBC1L(λ)/neo and DNA fragments of 4955 bp (hm1) and 2349 bp (hm2) from the plasmid h/mMBC1L(λ)/neo. These DNA fragments were collected and purified from the gels using GENECLEANII Kit (BIO101). Each of the DNA fragments obtained was dissolved in 40 µl of a solution containing 10 mM Tris-HCl (pH 7.4) and 1 mM EDTA.

The m1 and hm1 fragments (1 µl each) were ligated to the hm2 and m2 fragments (4 µl each), respectively. Each of the resultant ligation products was introduced into a competent cell of *E. coli*, JM109, to form a transformant. The transformant obtained was cultured in 2 ml of 2xYT medium containing 50 µg/ml of ampicillin. From the cell fraction, the plasmid was purified using QIAprep Spin Plasmid Kit QIAGEN).

Each of the purified plasmids was digested in 20 µl of a reaction solution containing 10 mM Tris-HCl (pH 7.5), 10 mM MgCl$_2$, 1 mM DTT and either 8U of ApaI (Takara Shuzo Co., Ltd.) or 2U of ApaLI (Takara Shuzo Co., Ltd.) at 37° C. for 1 hour.

If the fragments were ligated correctly, the digestion reaction gave a fragment of 7304 bp (by the ApaI digestion) or fragments of 5560/1246/498 bp (by the ApaLI digestion) for m1-hm2, and gave fragments of 6538/766 bp (by the ApaI digestion) or fragments of 3535/2025/1246/498 bp (by the ApaLI digestion) for hm1-m2. Based on this assumption, the plasmids were identified. As a result, an expression vector encoding a human FR1/mouse FR2, 3, 4 hybrid antibody L-chain (designated "hmmMBC1L(λ)/neo") and an expression vector encoding a mouse FR1/human FR2/mouse FR3, 4 hybrid antibody L-chain (designated "mhmMBC1L(λ)/neo") were obtained.

(4) Construction of Humanized Antibody L-Chain

A humanized #23-57-137-1 antibody L-chain was prepared by CDR-grafting technique by means of PCR method. For the preparation of a humanized #23-57-137-1 antibody L-chain (version "a") that contained FR1, FR2 and FR3 derived from human antibody HSU03868 (GEN-BANK, Deftos M. et al., Scand. J. Immunol., 39, 95-103, 1994) and FR4 derived from human antibody S25755 (NBRF-PDB), six PCR primers were used.

The six primers were as follows: CDR-grafting primers MBC1LGP1 (SEQ ID NO: 29) and MBC1LGP3 (SEQ ID NO: 30), both having a sense DNA sequence, CDR-grafting primers MBC1LGP2 (SEQ ID NO: 31) and MBC1LGP4 (SEQ ID NO: 32), both having an antisense DNA sequence, all of which had a 15-21 bp complementary sequence on the both terminal ends; and external primers MBC1LVS1 (SEQ ID NO: 33) and MBC1LVR1 (SEQ ID NO: 34) having a homology to the CDR-grafting primers MBC1LGP1 and MBC1LGP4, respectively.

The CDR-grafting primers MBC1LGP1, MBC1LGP2, MBC1LGP3 and MBC1LGP4 were separated on a urea-denatured polyacrylamide gel (Molecular Cloning: A Laboratory Manual, Sambrook et al., Cold Spring Harbor Laboratory Press, 1989) and extracted therefrom segment by a crush-and-soak method (Molecular Cloning: A Laboratory Manual, Sambrook et al., Cold Spring Harbor Laboratory Press, 1989).

Each of the CDR-grafting primers (1 nmole) was separated with 6% denatured polyacrylamide gel. The identification of the DNA fragment of a desired length was performed on a silica gel thin plate by irradiation of UV ray. The desired DNA fragment was collected from the gel by a crush-and-soak method. The collected DNA fragment was dissolved in 20 µl of a solution containing 10 mM Tris-HCl (pH 7.4) and 1 mM EDTA.

The PCR reaction was performed using TaKaRa Ex Taq (Takara Shuzo Co., Ltd.) and a buffer appended thereto. The PCR reaction solution comprised (per 100 μl) 1 μl of each of the CDR-grafting primers MBC1LGP1, MBC1LGP2, MBC1LGP3 and MBC1LGP4, 0.25 mM dNTPs, 2.5U of TaKaRa Ex Taq in the buffer. The PCR reaction was run for 5 cycles under the conditions: 94° C. for 1 min., 55° C. for 1 min. and 72° C. for 1 min. The resultant reaction mixture was added with 50 pmoles of each of the external primers MBC1LVS1 and MBC1LVR1. Using this reaction mixture, the PCR reaction was run for additional 30 cycles under the same conditions. The DNA fragment thus amplified was separated by agarose gel electrophoresis on a 3% Nu Sieve GTG agarose (FMC Bio. Products).

An agarose segment containing a DNA fragment of 421 bp was excised, and the DNA fragment was purified therefrom using GENECLEANII Kit (BIO101) in accordance with the instructions included in the kit. The PCR reaction mixture thus obtained was used for subcloning of the DNA fragment into plasmid pUC19 that had been digested with BamHI and HindIII. The resultant plasmid was sequenced. The plasmid thus prepared was designated "hMBCL/pUC19". In this plasmid, however, the 104-position amino acid (corresponding to the 96th amino acid in accordance with the Kabat's prescription) of CDR4 was replaced by arginine. For the correction of this amino acid to tyrosine, a correction primer MBC1LGP10R (SEQ ID NO: 35) was designed and synthesized. The PCR reaction was performed using TaKaRa Ex Taq (Takara Shuzo Co., Ltd.) and a buffer appended thereto. The PCR reaction solution comprised (per 100 μl) 0.6 μg of the plasmid hMBCL/pUC19 as a template DNA, 50 pmoles of each of the primers MBC1LVS1 and MBC1LGP10R, 2.5U of TaKaRa Ex Taq (Takara Shuzo Co., Ltd.) and 0.25 mM dNTPs in the buffer, over which mineral oil (50 μl) was layered. The PCR reaction was run for 30 cycles under the conditions: 94° C. for 1 min., 55° C. for 1 min. and 72° C. for 1 min. The DNA fragment thus amplified was separated by agarose gel electrophoresis on a 3% Nu Sieve GTG agarose (FMC Bio. Products).

A gel segment containing a DNA fragment of 421 bp was excised, and the DNA fragment was purified therefrom using GENECLEANII Kit (BIO101) in accordance with the instructions included in the kit. The PCR reaction mixture thus prepared was used for subcloning of the DNA fragment into plasmid pUC19 that had been digested with BamHI and HindIII.

The plasmid was sequenced using M13 Primer M4 and M13 Primer RV. As a result, it was confirmed that the plasmid had the correct sequence. The plasmid was then digested with HindIII and BlnI, and a DNA fragment of 416 bp was separated by electrophoresis on a 1% agarose gel. The DNA fragment was purified using GENECLEANII Kit (BIO101) in accordance with the instructions included in the kit, and then introduced into plasmid Cλ/pUC19 that had been digested with HindIII and BlnI. The resultant plasmid was designated "hMBC1Laλ/pUC19". This plasmid was digested with EcoRI to give a DNA fragment encoding humanized L-chain. The DNA fragment was introduced into plasmid pCOS1 so that the initiation codon for the humanized L-chain was located downstream to the EF1α promoter. The plasmid thus obtained was designated "hMBC1Laλ/pCOS1". The DNA sequence (including the corresponding amino acid sequence) of the humanized L-chain version "a" is shown in SEQ ID NO: 66. The amino acid sequence of the version "a" is also shown in SEQ ID NO: 47.

A humanized L-chain version "b" was prepared using a mutagenesis technique by a PCR method. The version "b" was designed such that the 43-position amino acid glycine (corresponding to the 43th amino acid in accordance with the Kabat's prescription) was replaced by proline and the 49-position amino acid lysine (corresponding to the 49th amino acid accordance with the Kabat's prescription) by aspartic acid in the version "a". The PCR reaction was performed using plasmid hMBC1Laλ/pUC19 as a template with a mutagenic primer MBC1LGP5R (SEQ ID NO: 36) and a primer MBC1LVS1. The DNA fragment obtained was digested with BamHI and HindIII, and the digestion fragment was subcloned into the BamHI-HindIII site of pUC19. After sequencing, the plasmid was digested with HindIII and AflII, and the resultant digestion fragment was ligated to plasmid hMBC1Laλ/pUC19 that had been digested with HindIII and AflII.

The plasmid thus obtained was designated "hMBC1Lbλ/pUC19". This plasmid was digested with EcoRI to give a DNA fragment containing DNA encoding the humanized L-chain. The DNA fragment was introduced into plasmid pCOS1 such that the initiation codon for the humanized L-chain was located downstream to the EF1α promoter. The plasmid thus obtained was designated "hMBC1Lbλ/pCOS1".

A humanized L-chain version "c" was prepared using a mutagenesis technique by a PCR method. The version "c" was designed such that the 84-position amino acid serine (corresponding to the 80th amino acid in accordance with the Kabat's prescription) was replaced by proline. The PCR reaction was performed using plasmid hMBC1Laλ/pUC19 as a template with a mutagenic primer MBC1LGP6S (SEQ ID NO: 37) and a primer M13 Primer RV. The DNA fragment obtained was digested with BamHI and HindIII and then subcloned into pUC19 that had been digested with BamHI and HindIII.

After sequencing, the plasmid was digested with BstPI and Aor51HI, and the resultant DNA fragment was ligated to plasmid hMBC1Laλ/pUC19 that had been digested with BstPI and Aor51HI. The plasmid thus obtained was designated "hMBC1Lcλ/pUC19". This plasmid was digested with EcoRI to give a DNA fragment containing DNA encoding the humanized L-chain. The fragment was introduced into the EcoRI site of plasmid pCOS1 such that the initiation codon for the humanized L-chain was located downstream to the EF1α promoter. The plasmid thus obtained was designated "hMBC1Lcλ/pCOS1".

Humanized L-chain versions "d", "e" and "f" were also prepared using a mutagenesis technique by a PCR method. The versions "d", "e" and "f" were designed such that the 91-position amino acid tyrosine (corresponding to the 87th amino acid in accordance with the Kabat's prescription) was replaced by isoleucine in the versions "a", "b" and "c", respectively. For each of the versions "d", "e" and "f", a PCR reaction was performed using each of plasmid hMBC1Laλ/pCOS1 (for version "d"), hMBC1Lbλ/pCOS1 (for version "e") and hMBC1Lcλ/pCOS1 (for version "f"), respectively, as a template, a mutagenic primer MBC1LGP11R (SEQ ID NO: 38) and a primer M-S1 (SEQ ID NO: 44). The DNA fragment thus obtained was digested with BamHI and HindIII and then subcloned into pUC19 that had been digested with BamHI and HindIII. After sequencing, the plasmid was digested with HindIII and BlnI, and the resultant digestion fragment was ligated to plasmid Cλ/pUC19 that had been digested with HindIII and BlnI.

The plasmids thus obtained were respectively designated "hMBC1Ldλ/pUC19" (for version "d"), "hMBC1Leλ/pUC19" (for version "e") and "hMBC1Lfλ/pUC19" (for version "f"). Each of these plasmids was digested with EcoRI to give a DNA fragment containing DNA encoding the humanized L-chain. The DNA fragment was introduced into the EcoRI site of plasmid pCOS1 such that the initiation codon for the humanized L-chain was located downstream to the EF1α promoter of the plasmid. The plasmids thus obtained were respectively designated "hMBC1Ldλ/pCOS1" (for version "e"), "hMBC1Leλ/pCOS1" (for version "e") and "hMBC1Lfλ/pCOS1" (for version "f").

Humanized L-chain versions "g" and "h" were also prepared using a mutagenesis technique by a PCR method. The versions "g" and "h" were designed such that the 36-position amino acid histidine (corresponding to the 36th amino acid in accordance with the Kabat's prescription) was replaced by tyrosine in the versions "a" and "d", respectively. The PCR reaction was performed using a mutagenic primer MBC1LGP9R (SEQ ID NO: 39), M13 Primer RV and plasmid hMBC1Laλ/pUC19 as a template. An additional PCR was performed using the PCR product thus obtained and M13 Primer M4 as a primer and plasmid hMBC1Laλ/pUC19 as a template. The DNA fragment obtained was digested with HindIII and BlnI and then subcloned into plasmid Cλ/pUC19 that had been digested with HindIII and BlnI. Using this plasmid as a template, a PCR reaction was performed with primers MBC1LGP13R (SEQ ID NO: 40) and MBC1LVS1. The PCR fragment obtained was digested with ApaI and HindIII and then introduced into either of plasmids hMBC1Laλ/pUC19 and hMBC1Ldλ/pUC19 that had been digested with ApaI and HindIII. The plasmids obtained were sequenced. Plasmids that were confirmed to contain the correct sequence were designated "hMBC1Lgλ/pUC19" (for version "g") and "hMBC1Lhλ/pUC19" (for version "h"). Each of these plasmids was digested with EcoRI to give a DNA fragment containing DNA encoding the humanized L-chain. The DNA fragment was introduced into the EcoRI site of plasmid pCOS1 such that the initiation codon for the humanized L-chain was located downstream to the EF1α promoter. The plasmids thus obtained were respectively designated "hMBC1Lgλ/pCOS1" (for version "g") and "hMBC1Lhλ/pCOS1" (for version "h") Humanized L-chain versions "i", "j", "k", "l", "m", "n" and "o" were also prepared using a mutagenesis technique by a PCR method. The PCR reaction was performed using plasmid hMBC1Laλ/pUC19 as a template with a mutagenic primer MBC1LGP14S (SEQ ID NO: 41) and a primer V1RV (λ) (SEQ ID NO: 43). The resultant DNA fragment was digested with ApaI and BlnI and then subcloned into plasmid hMBC1Lgλ/pUC19 that had been digested with ApaI and BlnI. The plasmid obtained was sequenced, and the clone into which the mutation for each version was introduced was selected. The plasmid thus obtained was designated "hMBC1Lxλ/pUC19 (x=i, j, k, l, m, n or o)". This plasmid was digested with EcoRI to give a DNA fragment containing DNA encoding the humanized L-chain. The DNA fragment was introduced into the EcoRI site of plasmid pCOS1 such that the initiation codon for the humanized L-chain was located downstream to the EF1α promoter. The plasmid thus obtained was designated "hMBC1Lxλ/pCOS1" (x=i, j, k, l, m, n or o). The DNA sequences (including the corresponding amino acid sequences) of the versions "j", "l", "m" and "o" are shown in SEQ ID NOs: 67, 68, 69 and 70, respectively. The amino acid sequences of these versions are also shown in SEQ ID Nos: 48, 49, 50 and 51, respectively.

Humanized L-chain versions "p", "q", "r", "s" and "t" were designed such that the 87-position amino acid (tyrosine) was replaced by isoleucine in the versions "i", "j", "m", "l" and "o", respectively. These versions were prepared utilizing the Aor51MI restriction site of FR3 and replacing that site of each of the versions "i", "j", "m", "l" or "o" by that site of the version "h". That is, an Aor51HI restriction fragment (514 bp) containing CDR3, a portion of FR3 and the entire FR4 were removed from an expression plasmid hMBC1Lxλ/pCOS1 (x=i, j, m, l or o). To the removed site, an Aor51HI restriction fragment (514 bp) in the expression plasmid hMBC1Lhλ/pCOS, which containing CDR3 and a portion of FR3 and the entire FR4, was ligated, so that the 91-position amino acid tyrosine (corresponding to the 87th amino acid in accordance with the Kabat's prescription) was replaced by isoleucine. The resultant plasmid was sequenced. A clone of each of the versions "i", "j", "m" "l" and "o" in which 91-position amino acid tyrosine (corresponding to the 87th amino acid in accordance with the Kabat's prescription) was replaced by isoleucine was selected. These modified versions respectively corresponding to the versions "i", "j", "m" "l" and "o" were designated versions "p", "q", "s", "r" and "t", respectively. The obtained plasmid was designated "hMBC1Lxλ/pCOS1 (x=p, q, s, r or t). The DNA sequences (including the corresponding amino acids) of the versions "q", "r", "s" and "t" are shown in SEQ ID Nos: 71, 72, 73 and 74, respectively. The amino acid sequences of these versions are also shown in SEQ ID Nos: 52, 53, 54 and 55, respectively.

Plasmid hMBC1Lqλ/pCOS1 was digested with HindIII and EcoRI and then subcloned into plasmid pUC19 that had been digested with HindIII and EcoRI. The plasmid thus obtained was designated "hMBC1Lqλ/pUC19.

The positions of the replaced amino acids in the individual versions of the humanized L-chain are shown in Table 2 below.

TABLE 2

Positions of replaced amino acid in sequence listings (amino acid numbering in accordance with the Kabat's prescription)

| Versions | 36 | 43 | 45 | 47 | 49 | 80 | 87 |
|---|---|---|---|---|---|---|---|
| a |   |   |   |   |   |   |   |
| b |   | P |   |   | D |   |   |
| c |   |   |   |   |   | P |   |
| d |   |   |   |   |   |   | I |
| e |   | P |   |   | D |   | I |
| f |   |   |   |   |   | P | I |
| g | Y |   |   |   |   |   |   |
| h | Y |   |   |   |   |   | I |
| i | Y |   | K |   |   |   |   |
| j | Y |   | K |   | D |   |   |
| k | Y |   | K | V |   |   |   |
| l | Y |   | K | V | D |   |   |
| m | Y |   |   |   | D |   |   |
| n | Y |   |   | V |   |   |   |
| o | Y |   |   | V | D |   |   |
| p | Y |   | K |   |   |   | I |
| q | Y |   | K |   | D |   | I |
| r | Y |   |   |   | D |   | I |
| s | Y |   | K | V | D |   | I |
| t | Y |   |   | V | D |   | I |

In Table 2, capital letters represent the following amino acids: Y: tyrosine; P: proline; K: lysine, V: valine; D: aspartic acid; and I: isoleucine.

*E. coli* strains each containing plasmids hMBC1HcDNA/pUC19 and hMBC1Lqλ/pUC19 were designated "*Escherichia coli* JM109 (hMBC1HcDNA/pUC19)" and "*Escherichia coli* JM109 (hMBC1Lqλ/pUC19)", respectively, which have been deposited under the terms of Budapest Treaty at the National Institute of Bioscience and Human-Technology, Agency of Industrial Science and Technology, Japan, (1-3, Higashi 1-chome, Tsukuba-shi, Ibaraki, Japan) on Aug. 15, 1996, under the accession No. FERM BP-5629 for *Escherichia coli* JM109 (hMBC1HcDNA/pUC19), and FERM BP-5630 for *Escherichia coli* JM109 (hMBC1Lqλ/pUC19).

(5) Transfection into COS-7 Cell

For the evaluation of the antigen-binding activity and the neutralizing activity of the hybrid antibodies and the humanized #23-57-137-1 antibodies, the above-prepared expression plasmids were expressed transiently in COS-7 cells. For the transient expression of the L-chain hybrid antibodies, each of the following combinations of plasmids were co-transfected into a COS-7 cell by electroporation using Gene Pulser (Bio Rad): hMBC1HcDNA/pCOS1 and h/mMBC1L(λ)/neo; hMBC1HcDNA/pCOS1 and m/hMBC1Laλ/neo; hMBC1HcDNA/pCOS1 and m/hMBC1Ldλ/neo; hMBC1HcDNA/pCOS1 and hmmMBC1L(λ)/neo; and hMBC1HcDNA/pCOS1 and mhmMBC1L(λ)/neo. That is, a cell suspension (0.8 ml) of COS-7 cells in PBS(−) ($1\times10^7$ cells/ml) was added with each combination of the plasmid DNAs (10 μg each). The resultant solution was applied with pulses at an electrostatic capacity of 1,500V and 25 μF. After 10 min. of recovery period at room temperature, the electroporated cells were suspended in DMEM medium containing 2% Ultra Low IgG fetal calf serum (GIBCO), and then cultured using a 10-cm culture dish in a $CO_2$ incubator. After cultivating for 72 hours, a culture supernatant was collected and centrifuged to remove cell debris. The solutions thus prepared were provided for use in the ELISA below.

For the transient expression of the humanized #23-57-137-1 antibodies, the combination of plasmids of hMBC1HcDNA/pCOS1 and hMBC1Lxλ/pCOS1 (x=a–t) were co-transfected into a COS-7 cell using Gene Pulser (Bio Rad) in the same manner as described for the hybrid antibodies above. The culture supernatants were prepared and provided for use in the ELISA below.

The purification of the hybrid antibodies and the humanized antibodies from the COS-7 cell culture supernatants was performed using AffiGel Protein A MAPSII Kit (Bio Rad) in accordance with the instructions included in the kit.

(6) ELISA (i) Determination of Antibody Concentration

An ELISA plate for determining antibody concentration was prepared as follows. Each well of a 96-well ELISA plate (Maxisorp, NUNC) was coated with 100 μl of a coating buffer (0.1 M $NaHCO_3$, 0.02% $NaN_3$) containing 1 μg/ml of goat anti-human IgG antibody (TAGO) and then blocked with 200 μl of a dilution buffer [50 mM Tris-HCl, 1 mM $MgCl_2$, 0.1 M NaCl, 0.05% Tween 20, 0.02% $NaN_3$, 1% bovine serum albumin (BSA); pH 7.2]. Each of the wells was added with each of the serial dilutions of the COS cell culture supernatant in which each of the hybrid antibodies and the humanized antibodies was expressed, or added with each of the serial dilutions of each of the hybrid antibodies and humanized antibodies in a purified form. The plate was incubated at room temperature for 1 hour and washed with PBS-Tween 20. Subsequently, each of the wells was added with 100 μl of alkaline phosphatase-conjugated goat anti-human IgG antibody (TAGO). The plate was incubated at room temperature for 1 hour and washed with PBS-Tween 20. Subsequently, each of the wells was added with 1 mg/ml of a substrate solution ("Sigma 104", p-nitrophenylphosphoric acid, SIGMA). The solution in each well was measured on its absorbance at 405 nm using Microplate Reader (Bio Rad) to determine the antibody concentration. In this determination, Hu IgG1λ Purified (The Binding Site) was used as the standard.

(ii) Determination of Antigen-Binding Ability

An ELISA plate for determining antigen-binding ability was prepared as follows. Each well of a 96-well ELISA plate (Maxisorp, NUNC) was coated with 100 μl of a coating buffer containing 1 μg/ml of human PTHrP (1-34) and then blocked with 200 μl of a dilution buffer. Subsequently, each well was added with each of the serial dilutions of the COS-7 cell culture supernatant in which each of the hybrid antibodies and humanized antibodies was expressed, or added with each of the serial dilutions of each of the hybrid antibodies and humanized antibodies in a purified form. The plate was incubated at room temperature and washed with PBS-Tween 20. Subsequently, each well was added with 100 μl of alkaline phosphatase-conjugated goat anti-human IgG antibody (TAGO). The plate was incubated at room temperature and washed with PBS-Tween 20. Subsequently, each well was added with 1 mg/ml of a substrate solution ("Sigma 104", p-nitrophenylphosphoric acid, SIGMA). The solution was measured on its absorbance at 405 nm using Microplate Reader (Bio Rad).

(7) Confirmation of Activities (i) Evaluation of Humanized H-Chain

Figure 6:
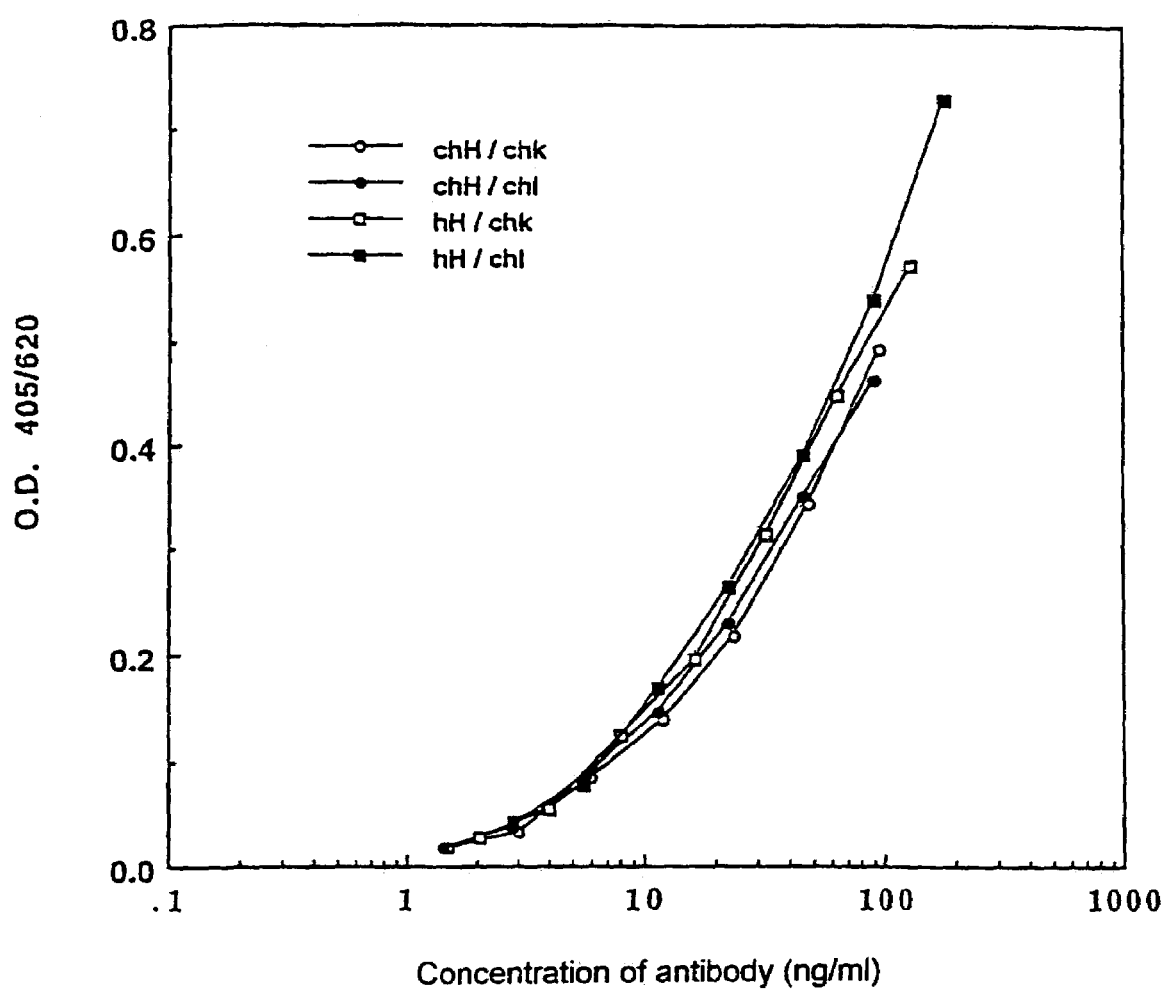
FIG. 6. is a graphical illustration of the measurement results of the antigen-binding activity. "chH/chk" refers to the chimeric antibody with L-chain k chain C-region, while "chH/chl" refers to the chimeric antibody with L-chain λ chain C-region. "hH/chk" and "hH/chl" both have a humanized H-chain version "a".

It was found that an antibody having a humanized H-chain version "a" and a chimeric L-chain exhibited the same level of PTHrP-binding activity as that of a chimeric antibody (see FIG. 6). This result suggests that the version "a" achieves the humanization of the H-chain V-region in the degree enough to evaluate the humanization. Therefore, the humanized H-chain version "a" was provided for use as a humanized antibody H-chain in the following experiments.

(ii) Activity of Hybrid Antibodies (ii-a) FR1, 2/FR3, 4 Hybrid Antibody

Figure 7:
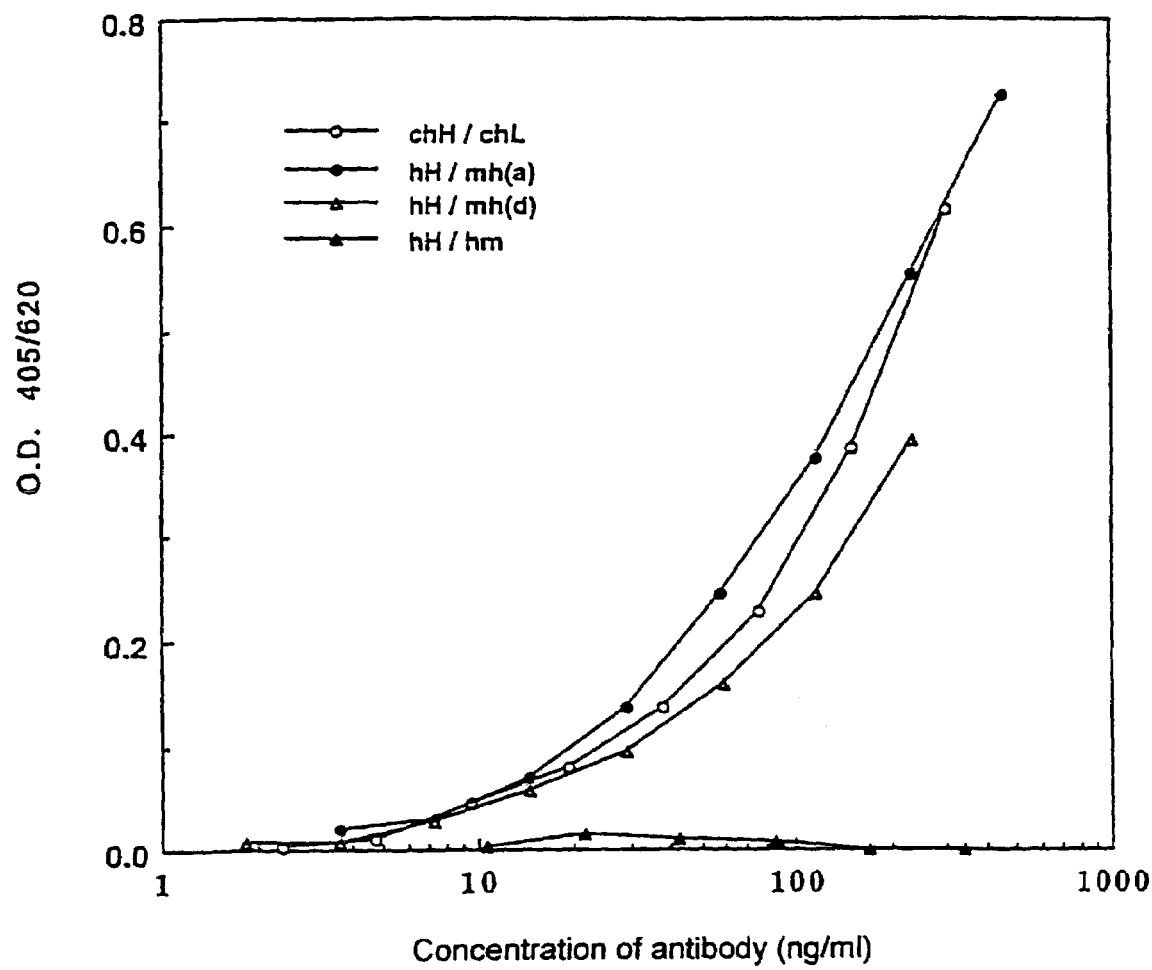
FIG. 7. is a graphical illustration of the measurement results of the antigen-binding activity. "chH/chl" refers to the chimeric antibody with L-chain λ chain C-region. "hHlmh (a)" refers to a hybrid antibody with the L chain being m/hMBC1 Laλ, while "hH/mh(d) refers to a hybrid antibody with the L chain being m/hMBC1 Ldλ. "hH/hM" refers to a hybrid antibody with the L chain being h/mMBC1L(λ).

When the L-chain was h/mMBC1L(λ), no antigen-binding activity was observed. In contrast, when the L-chain was either m/hMBC1Laλ or m/hMBC1Ldλ, the same level of antigen-binding activity as that of the chimeric #23-57-137-1 antibody was observed (FIG. 7). These results suggest that there is no problem with respect to FR3 and FR4 but there exist amino acid residue(s) that need to be replaced in FR1 and FR2 for the preparation of a humanized antibody.

(ii-b) FR1/FR2 Hybrid Antibody

Figure 8:
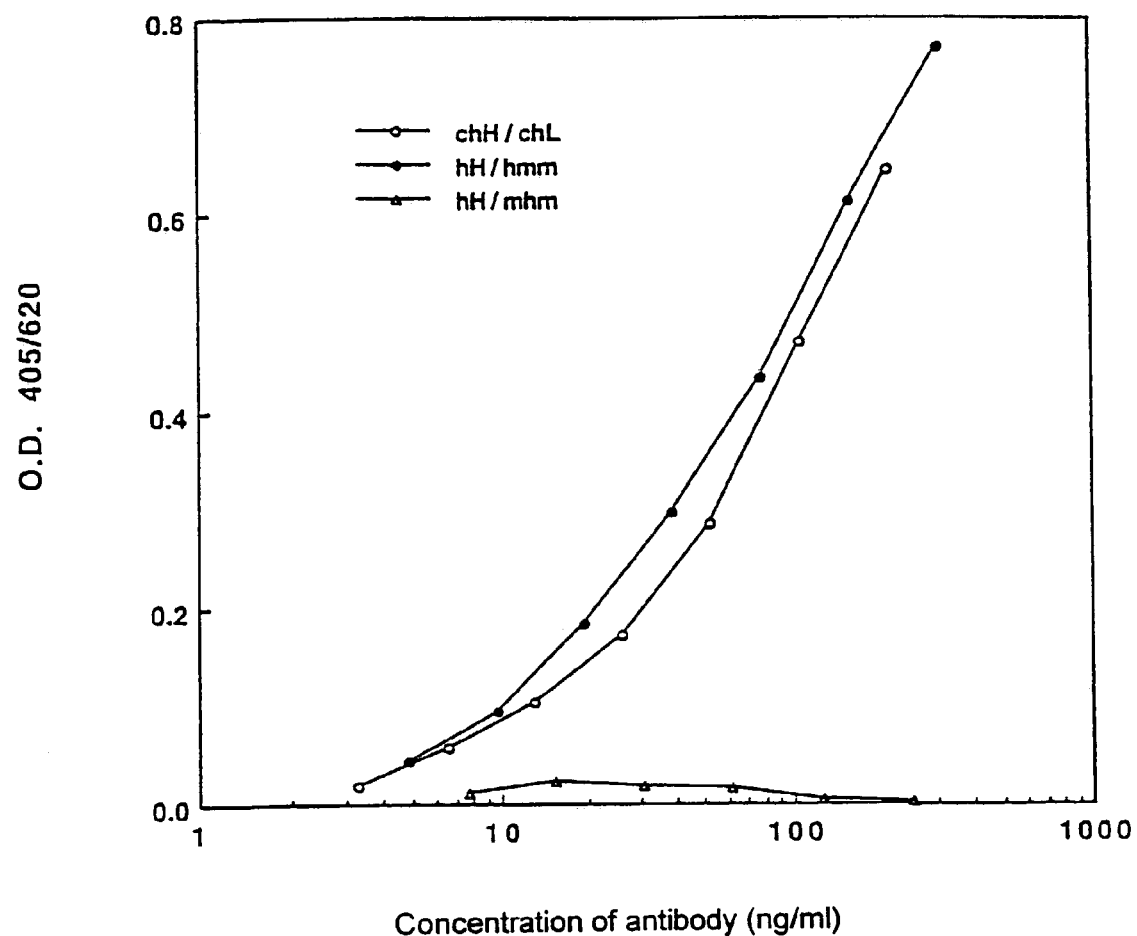
FIG. 8. is a graphical illustration of the measurement results of the antigen-binding activity. "chH/chL" refers to the chimeric antibody with L-chain λ chain C-region. "hH/hmm" refers to a hybrid antibody with the L chain being hmmMBC1L(λ). while "hH/mhm" refers to a hybrid antibody with the L chain being mhmMBC1L(λ).
Figure 9:
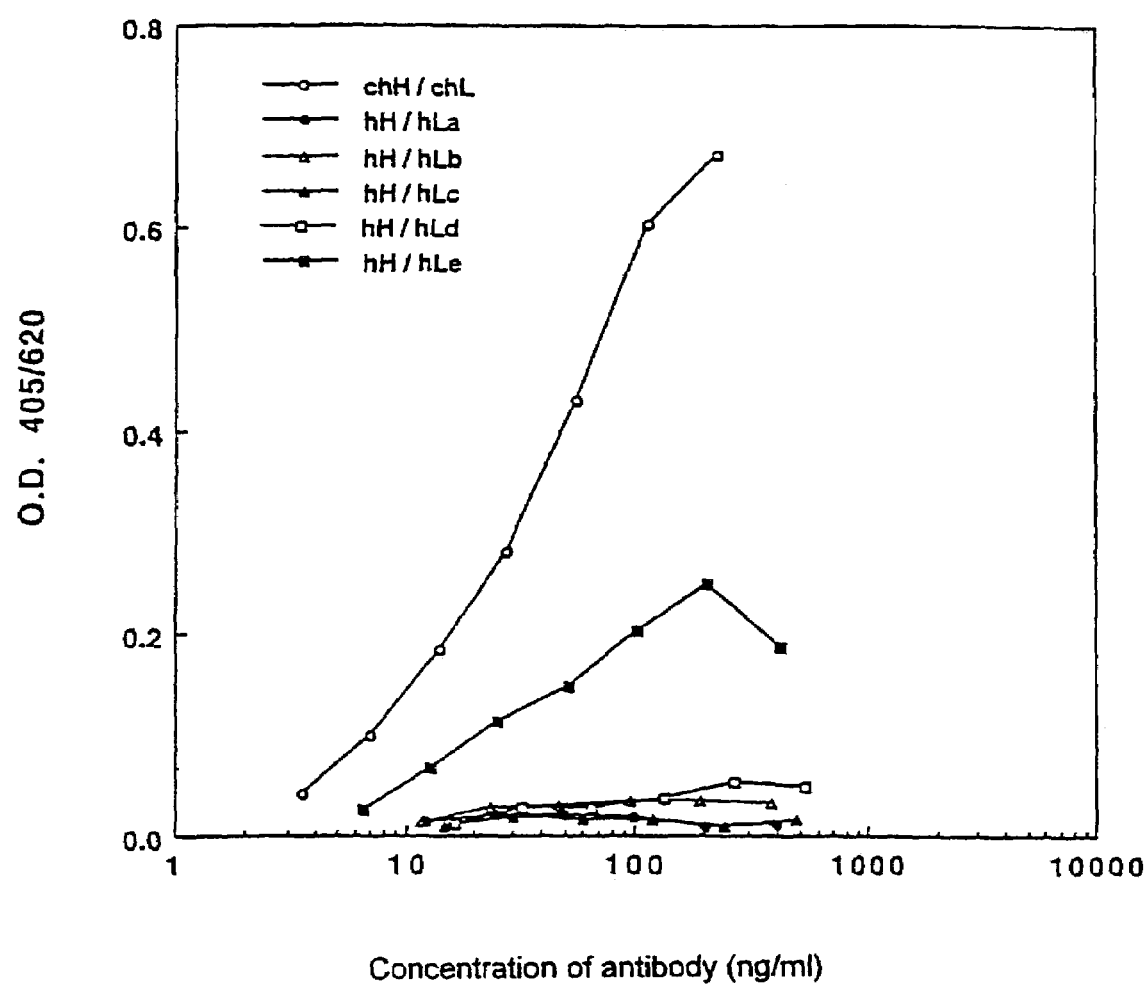
FIG. 9. is a graphical illustration of the measurement results of the antigen-binding activity. "chH/chL" refers to the chimeric antibody with L-chain λ chain C-region. "hH/hLa" refers to a hybrid antibody with the L chain version "a." "hH/hLb" refers to a hybrid antibody with the L chain version "b." "hH/hLc" refers to a hybrid antibody with the L chain version "c." "hH/hLd" refers to a hybrid antibody with the L chain version "d." "hH/hLe" refers to a hybrid antibody with the L chain version "e."
Figure 10:
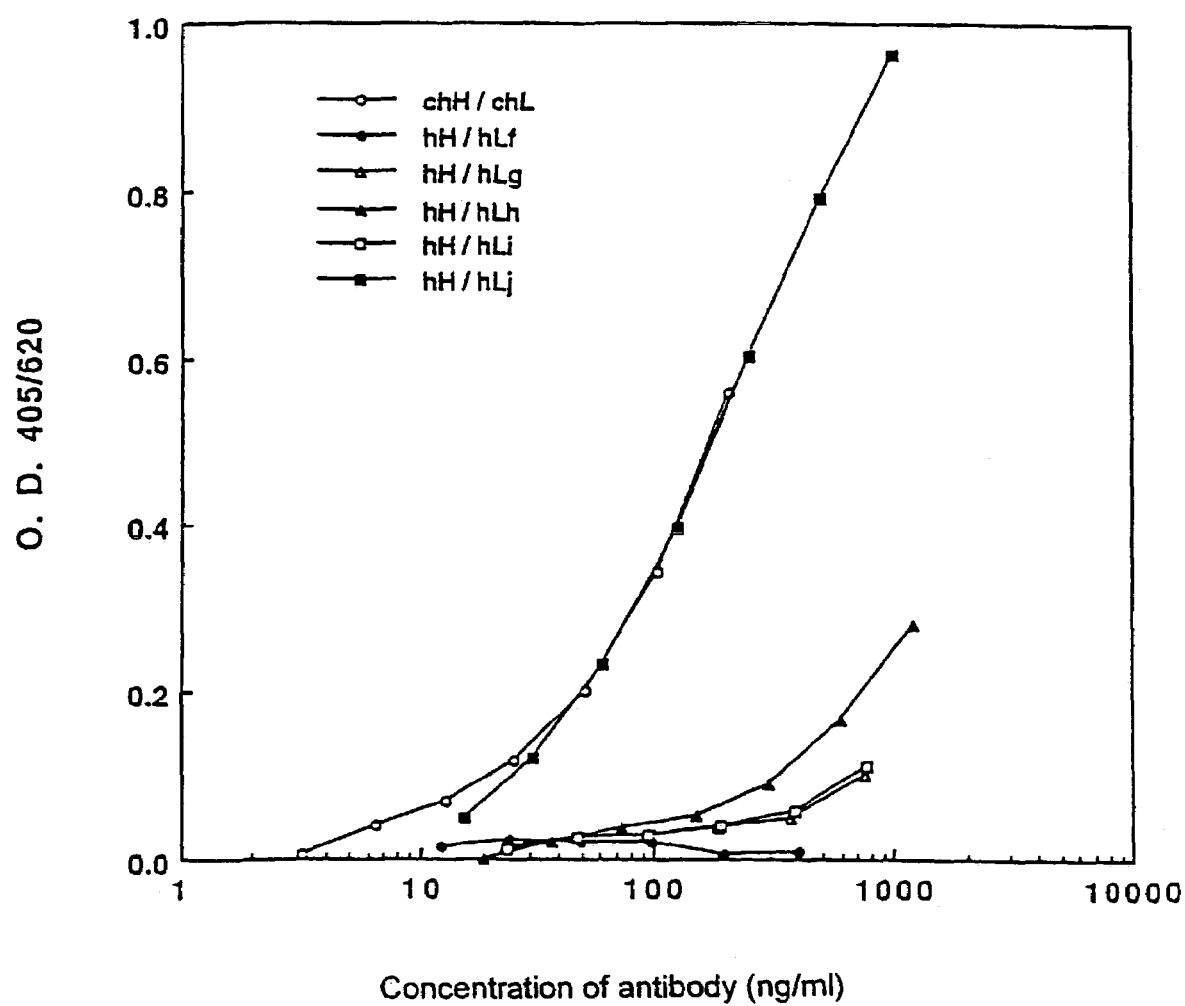
FIG. 10. is a graphical illustration of the measurement results of the antigen-binding activity. "chH/chL" refers to the chimeric antibody with L-chain λ chain C-region. "hH/hLf" refers to a hybrid antibody with the L chain version "f." "hH/hLg" refers to a hybrid antibody with the L chain version "g." "hH/hLh" refers to a hybrid antibody with the L chain version "h." "hH/hLi" refers to a hybrid antibody with the L chain version "i." "hH/hLi" refers to a hybrid antibody with the L chain version "i."
Figure 11:
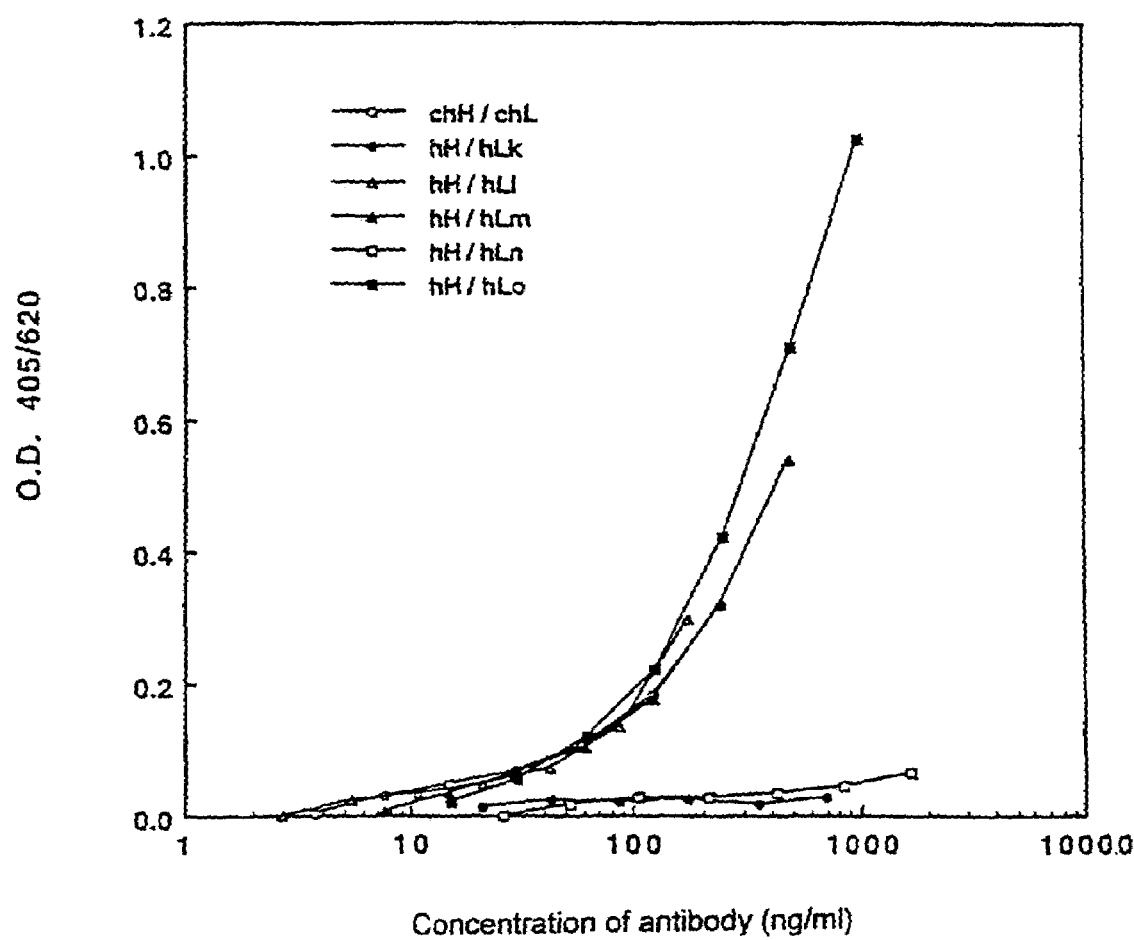
FIG. 11. is a graphical illustration of the measurement results of the antigen- binding activity. "chH/chL" refers to the chimeric antibody with L-chain λ chain C-region. "hH/hLk" refers to a hybrid antibody with the L chain version "k." "hH/hLl" refers to a hybrid antibody with the L chain version "l." "hH/hLm" refers to a hybrid antibody with the L chain version "m." "hH/hLn" refers to a hybrid antibody with the L chain version "n." "hH/hLo" refers to a hybrid antibody with the L chain version "o."
Figure 12:
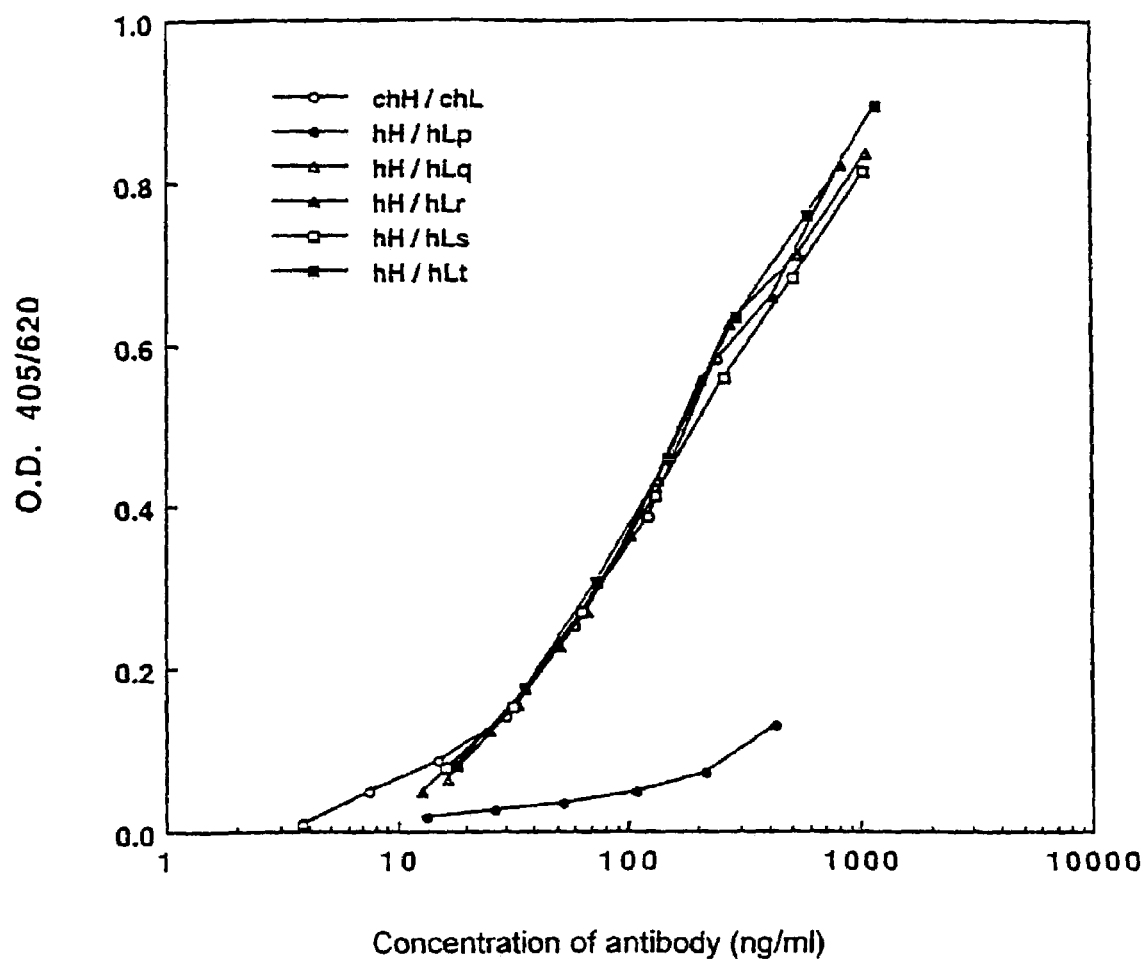
FIG. 12. is a graphical illustration of the measurement results of the antigen- binding activity. "chH/chL" refers to the chimeric antibody with L-chain λ chain C-region. "hH/hLp" refers to a hybrid antibody with the L chain version "p. " "hH/hLg" refers to a hybrid antibody with the L chain version "q. " "hH/hLr" refers to a hybrid antibody with the L chain version "r." "hH/hLs" refers to a hybrid antibody with the L chain version "s."  "hH/hLt" refers to a hybrid antibody with the L chain version "t."

When the L-chain was mhmMBC1L (λ), no antigen-binding activity was observed. In contrast, when the L-chain was hmmMBC1L(λ), the same level of antigen-binding activity as that of the chimeric #23-57-137-1 antibody was observed (FIG. 8). These results suggest that there is no problem with respect to FR1 but there exist amino acid residue(s) that need to be replaced in FR2 for the preparation of a humanized antibody.

(iii) Activity of Humanized Antibodies

Humanized antibodies each having the L-chain versions "a" to "t", were determined on the antigen-binding activity. As a result, it was found that the humanized antibodies having the L-chain versions "j", "l" "m", "o", "q", "r", "s" and "t" exhibited the same level of PTHrP-binding activity as that of the chimeric antibody (FIGS. 9 to 12).

(8) Establishment of CHO Cell Line Capable of Stable Production of Antibody

For establishing a cell line capable of stable production of humanized antibodies, each of the above-prepared expression plasmids was introduced into a CHO cell (DXB11).

That is, the establishment of a cell line capable of stable production of a humanized antibody was performed using each of the following combinations of plasmids as expression vectors for a CHO cell: hMBC1HcDNA/pCHO1 and hMBC1Lmλ/pCOS1; hMBC1HcDNA/pCHO1 and hMBC1Lqλ/pCOS1; and hMBC1HcDNA/pCHO1 and hMBC1Lrλ/pCOS1. The plasmids were co-transfected into a CHO cell by electroporation using Gene Pulser (Bio Rad). Subsequently, the expression vectors were separately cleaved with restriction enzyme PvuI to give linear DNA fragments. The resultant DNA fragments were extracted with phenol and chloroform and then precipitated with ethanol. The DNA fragments thus prepared were used in the subsequent electroporation. That is, the plasmid DNA fragments (10 µg each) were added to 0.8 ml of a cell suspension of CHO cells in PBS(-) (1×10$^7$ cells/ml). The resultant solution was applied with pulses at an electrostatic capacity of 1,500V and 25 µF. After 10 min. of recovery period at room temperature, the cells thus treated were suspended in MEM-α medium (GIBCO) containing 10% fetal calf serum (GIBCO), and then cultured in a $CO_2$ incubator using 96-well plates (Falcon). On the day following the cultivation being started, the medium was replaced by ribonucleoside- or deoxyribonucleoside-free MEM-α selective medium containing 10% fetal calf serum (GIBCO) and 500 mg/ml of GENETICIN (G418Sulfate; GIBCO). From the culture medium, cells into which the antibody gene was introduced were selected. The culture medium was replaced by a fresh-one. About two weeks after the medium replacement, the cells were observed microscopically. When a favorable cell growth was observed, the cells were determined on the amount of the produced antibodies by conventional ELISA for determination of antibody concentration as mentioned above. Among the cells, those which produced a larger amount of antibodies were screened.

The cultivation of the established cell line capable of stable production of antibodies was scaled up in a roller bottle using a ribonucleoside- or deoxyribonucleoside-free MEM-α medium containing 2% Ultra Low IgG fetal calf serum. On each of day 3 and day 4 of the cultivation, the culture supernatant was collected and filtered using a 0.2-µm filter (Millipore) to remove cell debris therefrom. The purification of the humanized antibodies from the culture supernatant of the CHO cells was performed using POROS Protein A Column (PerSeptive Biosystems) on ConSep LC100 (Millipore) in accordance with the appended instructions. The humanized antibodies were provided for use in the determination of neutralizing activity and examination of pharmacological efficacy on hypercalcemic model animals. The concentration and the antigen-binding activity of the purified humanized antibodies were determined by the ELISA system as mentioned above.

REFERENCE EXAMPLE 5

Determination of Neutralizing Activity

The determination of neutralizing activity of the mouse antibodies, the chimeric antibodies and the humanized antibodies was performed using rat myeloma cell line ROS17/2.8-5 cells. The ROS17/2.8-5 cells were cultured in Ham'S F-12 medium (GIBCO) containing 10% fetal calf serum (GIBCO) in a $CO_2$ incubator. The ROS17/2.8-5 cells were seeded in each well of a 96-well plate at 10$^4$ cells/100 µl/well and cultured for one day. After the cultivation was completed, the culture medium was replaced by Ham'S F-12 medium (GIBCO) containing 4 mM Hydrocortisone and 10% fetal calf serum. After cultivating for three to four days, the cultured cells were washed with 260 µl of Ham'S F-12 medium (GIBCO), and then added with 80 µl of Ham's F-12 medium containing 1 mM isobutyl-1-methyl xanthine (IBMX, SIGMA), 10% fetal calf serum and 10 mM HEPES. The resultant mixture was incubated at 37° C. for 30 min.

Figure 13:
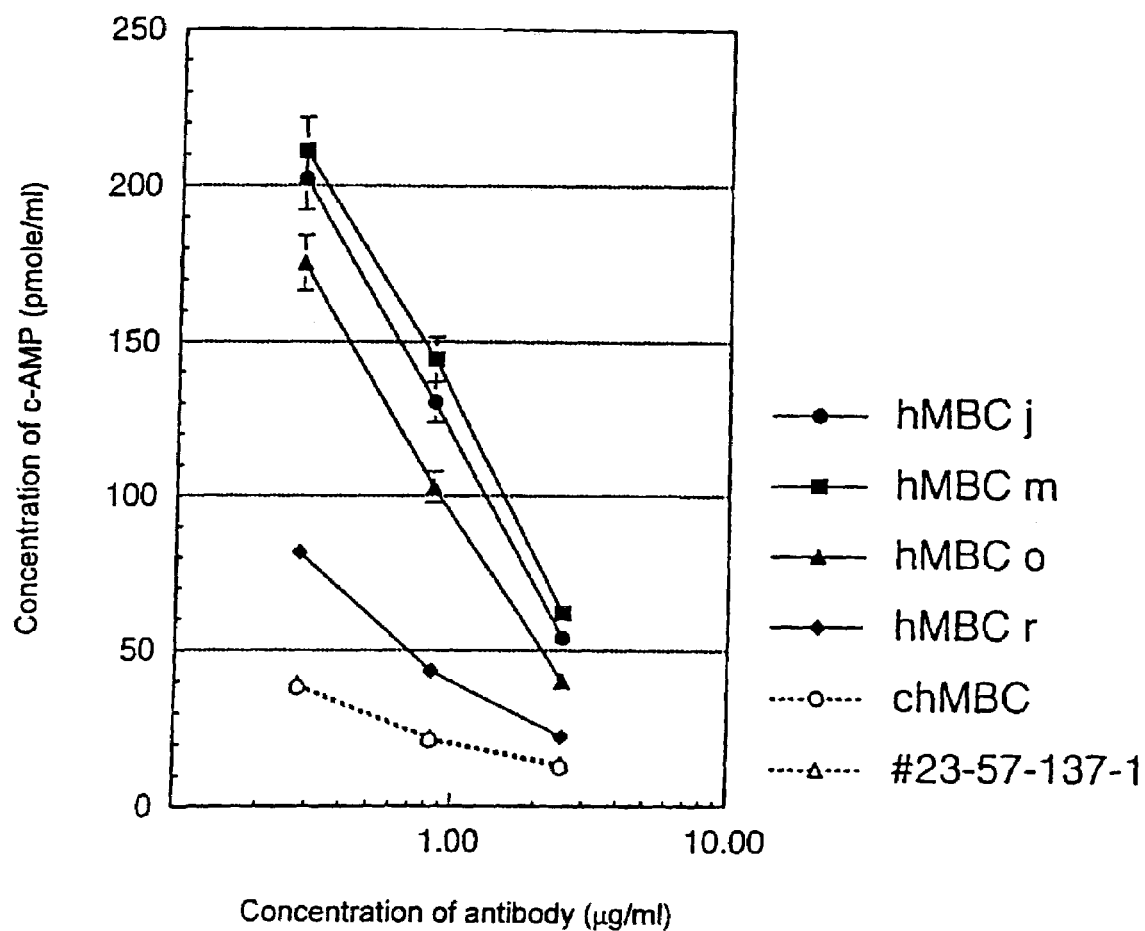
FIG. 13. is a graphical illustration of the neutralizing activity of a humanized antibody. "hMBC i" refers to a humanized antibody with the L chain version "i." "hMBC m" refers to a humanized antibody with the L chain version "m." "hMBC o" refers to a humanized antibody with the L chain version "o." "hMBC r" refers to a humanized antibody with the L chain version "r." "chMBC" refers to a chimeric antibody with the wild type L chain.
Figure 14:
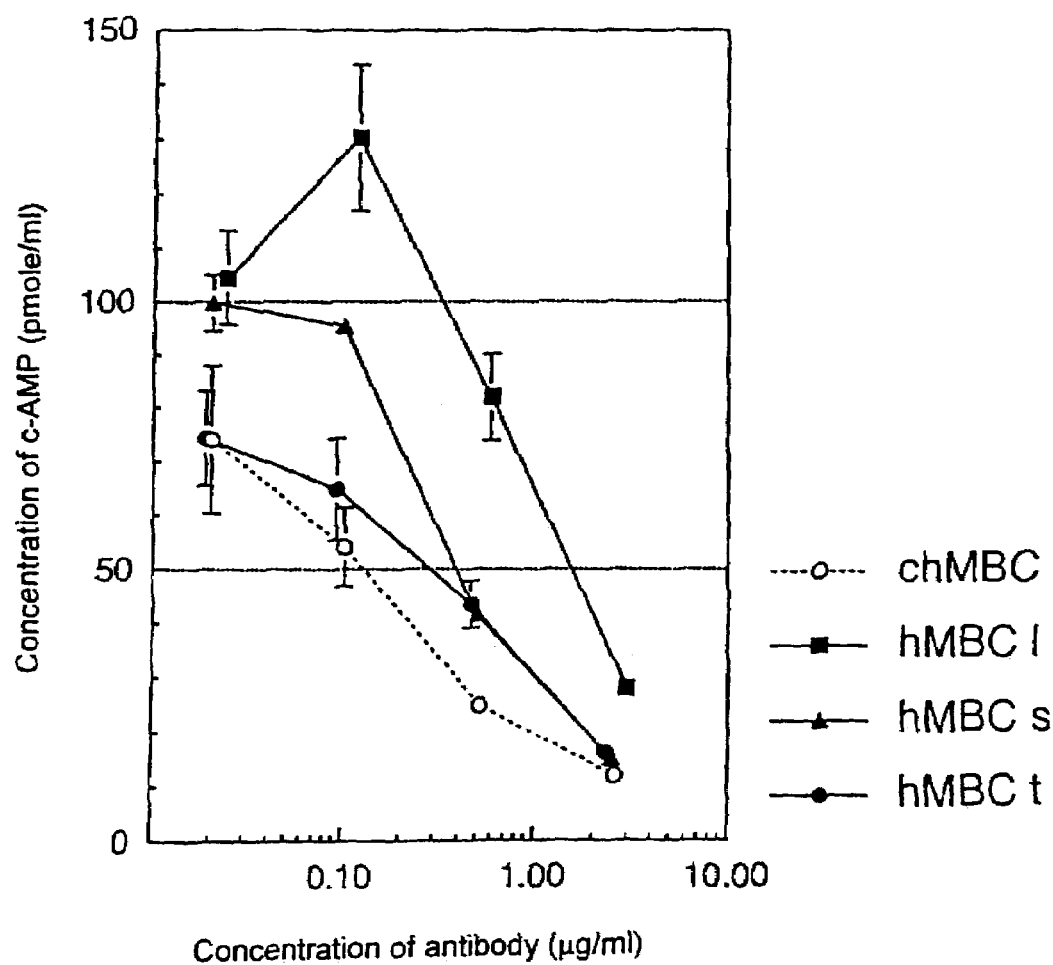
FIG. 14. is a graphical illustration of the neutralizing activity of a humanized antibody. "hMBC l" refers to a humanized antibody with the L chain version "l. " "hMBC s" refers to a humanized antibody with the L chain version "s. " "hMBC t" refers to a humanized antibody with the L chain version "t. " "chMBC" refers to a chiineric antibody with the wild type L chain.
Figure 15:
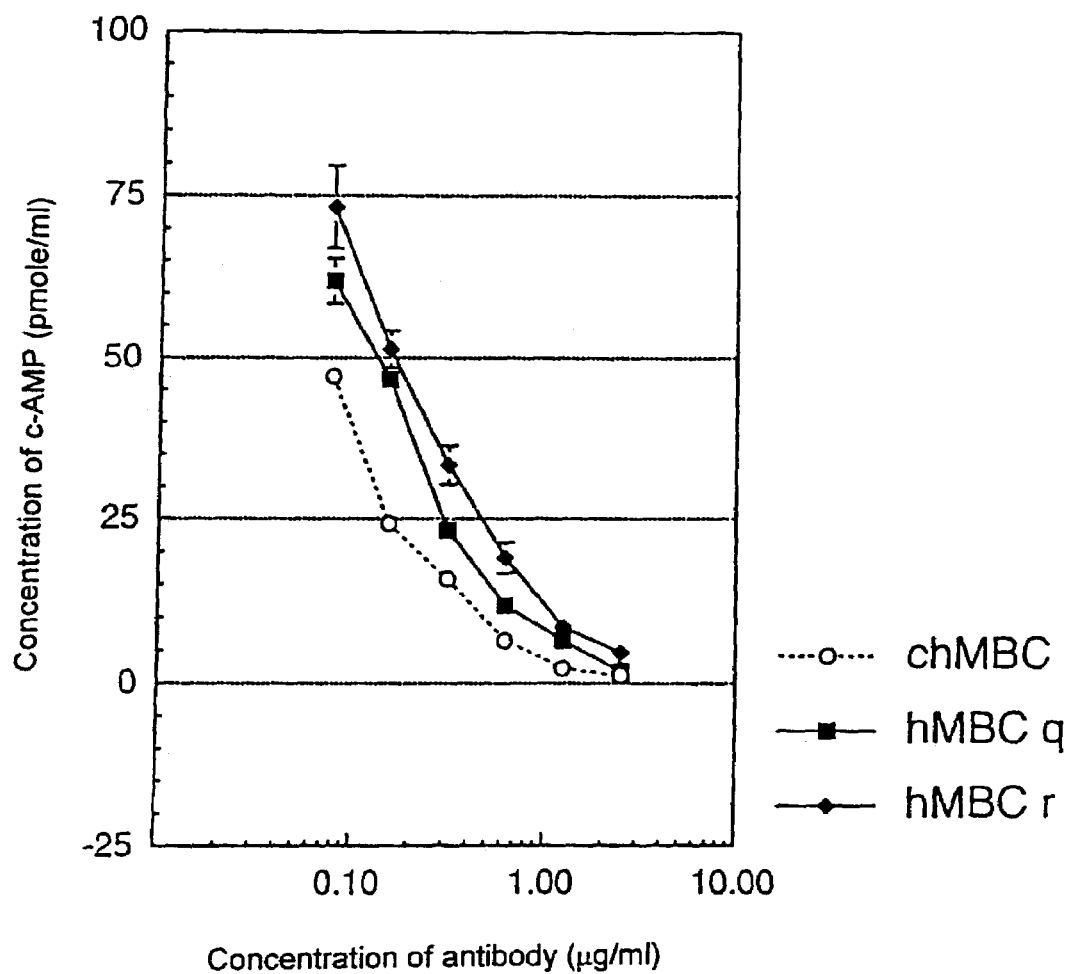
FIG. 15. is a graphical illustration of the neutralizing activity of a humanized antibody. "hMBC q" refers to a humanized antibody with the L chain version "q." "l,MBC r" refers to a humanized antibody with the L chain version "r." "chMBC" refers to a chimeric antibody with the wild type L chain.

The culture mediums of the mouse antibodies, the chimeric antibodies and the humanized antibodies to be tested for neutralizing activity were previously diluted serially in the following groups: [10 µg/ml, 3.3 µg/ml, 1.1 µg/ml and 0.37 µg/ml], [10 µg/ml, 2 µg/ml, 0.5 µg/ml and 0.01 µg/ml] and [10 µg/ml, 5 µg/ml, 1.25 µg/ml, 0.63 µg/ml and 0.31 µg/ml]. Each of the diluted antibody sample solutions was mixed with an equivalent amount of 4 ng/ml of PTHrP (1-34). The resultant mixed solution (80 µl) was added to each well. In each well, the final concentration of each antibody became a quarter of the above-mentioned concentration of the antibody, and accordingly the concentration of PTHrP (1-34) became 1 ng/ml. After the treatment at room temperature for 10 min., the culture supernatant was removed and the residue was washed with PBS three times. Subsequently, cAMP in the cells was extracted with 100 µl of a 0.3% HCl-95% ethanol and then evaporated using a water jet aspirator to remove the HCl-ethanol. The residue was dissolved in 120 µl of ETA buffer appended to cAMP EIA Kit (CAYMAN CHEMICAL'S) to extract the cAMP therefrom. The cAMP was determined using cAMP EIA Kit (CAYMAN CHEMICAL'S) in accordance with the instructions included in the kit. As a result, it was found that, among the humanized antibodies having the same level of antigen-binding activity as that of the chimeric antibody, those having L-chain versions "q", "r", "s" and "t" (in which the 91-position tyrosine was replaced by isoleucine) exhibited the closest neutralizing activity to that of the chimeric antibody, and those having a L-chain version "q" exhibited the strongest neutralizing activity (FIGS. 13 to 15).

INDUSTRIAL APPLICABILITY

As described above, the present invention provides a therapeutic agent for cachexia comprising, as an active ingredient, a substance capable of inhibiting the binding between PTHrP and a receptor thereof.

In the pharmacological efficacy tests using cachexia model animals, such substance can prevent weight loss and prolong the survival time compared with a control. Therefore, the substance is useful for treating cachexia.

The invention claimed is:

1. A method for preventing or treating at least one symptom of cachexia, comprising administering to a patient suffering from cachexia at least one humanized anti-PTHrP antibody or binding fragment thereof, wherein said humanized anti-PTHrP antibody or binding fragment thereof:

a) is humanized FERM BP-5631;

b) comprises a heavy chain variable region comprising amino acids 31-35, 50-66, and 99-107 of SEQ ID NO:46 and a light chain variable region comprising amino acids 23-34, 50-60, and 93-105 of SEQ ID NO:45; or c) comprises a deletion, replacement, addition, or insertion of from 1-5 amino acid residues of humanized FERM BP-5631;

and wherein said humanized anti-PTHrP antibody or binding fragment thereof binds PTHrP.

2. The method according to claim 1, wherein the cachexia is cancer-induced.

3. The method according to claim 1, wherein said at least one symptom is chosen from at least one of anorexia, loss of appetite, weakness, anemia, compromised immune function, and electrolyte imbalance.

4. The method according to claim 1, wherein said at least one humanized anti-PTHrP antibody or binding fragment thereof is an antagonist of a PTHrP receptor.

5. The method according to claim 1, wherein said at least one humanized anti-PTHrP antibody binding fragment is Fab, scFv, F(ab')2, or Fv.

6. The method according to claim 1, wherein said humanized antibody is humanized FERM BP-5631.

7. The method according to claim 1, wherein said cachexia is mediated by at least one cytokine.

8. The method according to claim 7, wherein the cytokine is at least one of TNF, IL-6, IFN, IL-1 or LIF.

9. The method according to claim 7, wherein the cytokine is an inflammatory cytokine.

10. The method according to claim 1, wherein the humanized anti-PTHrP antibody or binding fragment thereof comprises a heavy chain variable region comprising amino acids 31-35, 50-66, and 99-107 of SEQ ID NO:46 and a light chain variable region comprising amino acids 23-34, 50-60, and 93-105 of SEQ ID NO:45.

* * * * *